Figure 1A:
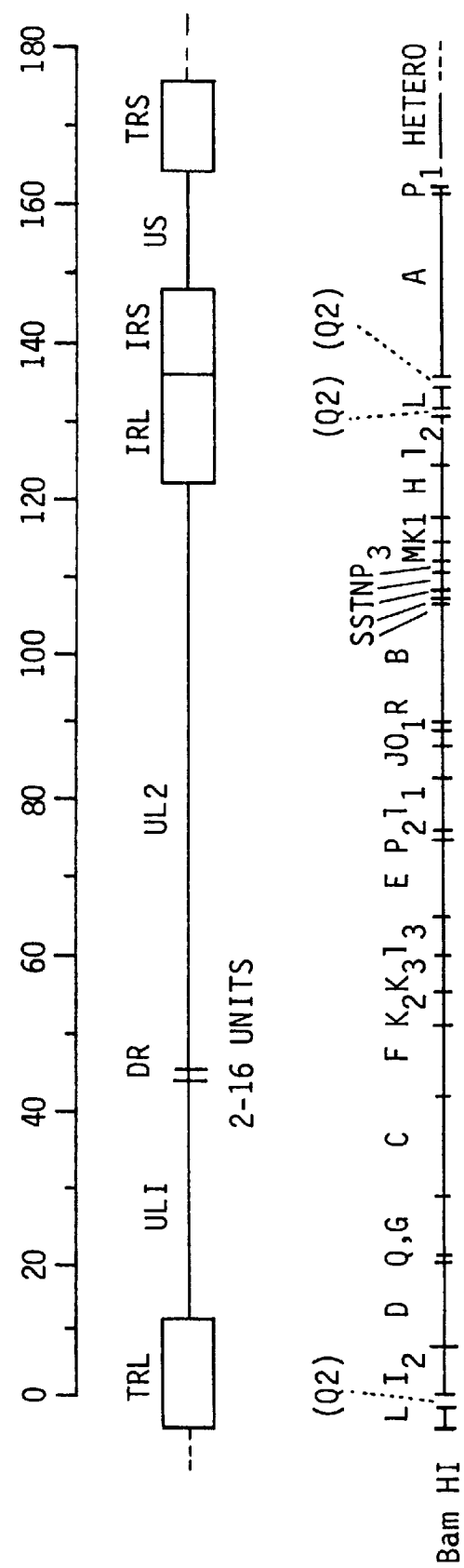

United States Patent [19]
Velicer et al.

[11] Patent Number: 6,087,127
[45] Date of Patent: Jul. 11, 2000

[54] MAREK'S DISEASE HERPESVIRUS DNA SEGMENT ENCODING GLYCOPROTEINS, GD, GI AND GE

[75] Inventors: Leland F. Velicer; Peter Brunovskis, both of East Lansing; Paul M. Coussens, DeWitt, all of Mich.

[73] Assignee: Board of Trustees operating Michigan State University, East Lansing, Mich.

[21] Appl. No.: 07/736,335

[22] Filed: Jul. 25, 1991

Related U.S. Application Data

[63] Continuation-in-part of application No. 07/572,711, Aug. 24, 1990, Pat. No. 5,138,033.
[51] Int. Cl.[7] ............................ C12P 21/02; C12N 15/10; C12N 15/38
[52] U.S. Cl. .................. 435/69.3; 435/91.41; 435/172.3; 435/320.1; 536/23.72
[58] Field of Search .............................. 435/69.1, 172.3, 435/320.1, 69.3, 91.41; 536/27, 23.1, 23.72

[56] References Cited

FOREIGN PATENT DOCUMENTS 9002803   3/1990   WIPO .

OTHER PUBLICATIONS

Production of Human Beta Interferon in Insect Cells Infected With Baculovirus Expansion Vector, Smith et al., Mol. and Cell Biol., vol. 3, pp. 2156–2165, 1983.

Shih et al. PNAS, vol. 81, Sep. 1984 pp. 5867–5870.

McGeoch et al. J. Mol. Biol. vol. 181, 1985, pp. 1–13.

Cebrian et al. PNAS, vol. 79, Jan. 1982, pp. 555–558.

Fukuchi et al. J. Virol. vol. 51, 1984, pp. 102–109.

*Primary Examiner*—David Guzo
*Attorney, Agent, or Firm*—Ian C. McLeod

[57] ABSTRACT

DNA encoding glycoproteins gD, gI and gE from Marek's disease herpesvirus is described. The DNA is useful for probes to detect the DNA in the herpesvirus, for expression to produce the glycoproteins that can be used for producing the antibodies which specifically recognize the three glycoprotein antigens, and in the case of the latter two genes, for potential insertion sites for foreign genes and as possible sites for gene inactivation to attenuate MDV field isolates for vaccine purposes.

2 Claims, 17 Drawing Sheets

```
3901 ATAGTTATCATGGACACACCCATCTTCACCTCCACCAATAATCTTTTTATTGTTAATAACTGGGCCGGTCTGATCTCCAAATCTTATACTTCTGGTAGAA
       I  I  M  S  V  G  M                                                E  C  G  I  S  S  K  V  H  D  S
4001 TATGAAACAGGGTTAAAACTAGGTAATAGAGTCTTCGACTCCGAGGCAGAAACGATGGAATGGCATTTCTTCGTCGAAGTACACGACTCT

14 K  T  N  T  T  Y  G  I  I  H  N  S  I  N  G  T  D  T  L  F  D  T  F  P  D  S  T  D  N  A  E  V  T
4101 AAAACTAATACTACCTACGGAATTATACATAACAGCATCAATGGTACGGATACGACGTTGTTTGATACTTTTCCGACAGTACGATAACGCGGAAGTGA

48 G  D  V  D  D  V  K  T  E  S  S  P  E  S  Q  S  E  D  L  S  P  F  G  N  D  G  N  E  S  P  E  T  V
4201 CGGGGGATGTGGACGATGTGAAGACTGAGAGCTCTCCCGAGTCCCAATCTGAAGATTTGTCACCTTTTGGGAACGATGGAAATGAATCCCCGAAACGGT

81 T  D  I  D  A  V  S  A  V  R  M  Q  Y  N  I  V  S  S  L  P  P  G  S  E  G  Y  I  V  C  T  K  R
4301 GACGGGACATTGATGCAGTTTCAGGTGTGCGAATGCAGTATAACATTGTTTCATCGTTACCGCCGGATCTGAAGGGTATATCTATGTTTGTACAAAGGCGT

114 G  D  N  T  K  R  K  V  I  V  K  A  V  T  G  G  K  T  L  G  S  E  I  D  I  L  K  K  M  S  H  R  S  I
4401 GGGGGATAATACCAAGAGAAAAGTCATTGTGAAAGCTGTGACTGGTGGCAAAACCCTTGGGAGTGAAATTGATATATTAAAAAAAATGTCTCACCGCTCCA

148 I  R  L  V  H  A  Y  R  W  K  S  T  V  C  M  V  M  P  K  Y  K  C  D  L  F  T  Y  I  D  I  M  G  P
4501 TAATTAGATTAGTTCATGCTTATAGATGGAAATCGACAGTTTGTATGTATGCCTAAATACAAATGCGACTTGTTTACGTACATAGATATCATGGGACC

181 I  L  P  L  N  Q  I  I  T  I  E  R  G  L  L  G  A  L  A  Y  I  H  E  K  G  I  I  H  R  D  V  K  T  E
4601 ATTGCCACTAAATCAAATAATTACGATAGAACGGGGTTTGCTTGGAGCATTGGCATATATCCACGAAAAGGGTATAATACATCGTGATGTAAAAACTGAA

214 N  I  F  L  D  K  P  E  N  V  L  G  D  F  G  A  A  C  K  L  D  E  H  T  D  K  P  K  C  Y  G  W  S
4701 AATATATTTTTGGATAAACCTGAAAATGTAGTATTGGGGGACTTTGGGGCAGCATGTAAATTAGATGAACATACAGATAAACCAAATGTTATGGATGGA

248 G  T  L  E  T  N  S  P  E  L  L  A  L  D  P  Y  C  T  K  T  D  I  W  S  A  G  L  V  L  F  E  M  S
4801 GTGGAACTCTGGAACTAATTCGCCTGAACTGCTTGCACTTGATCCATACTGTACAAAAACTGATATATGGAGTGCAGGATTAGTTCTGTTTGAGATGTC

281 V  K  N  I  T  F  F  G  K  Q  V  N  G  S  G  S  Q  L  R  S  I  I  R  C  L  Q  V  H  P  L  E  F  P
4901 AGTAAAAATATAACCTTTTTTGGCAAACAAGTAAACGGCTCAGGTTCTCAGCTACGAGATCCATAATTAGATGCCTGCAAGTCCATCCGTTGGAATTTCCA

314 Q  N  N  S  T  N  L  C  K  H  F  K  Q  Y  A  I  Q  L  R  H  P  Y  A  I  P  Q  I  I  R  K  S  G  M  T
5001 CAGAACAATTCTACAAACTTATGCAAACACTTCAAGCAGTACGCGATTCAGTTACGACAATCCCTCAGATTATACGAAAGAGTGGTATGA
```

```
US1    MDV    32   HPEYGSdsSd  qdfelnnv..  .GkFCplPWk  PDvaRLcaDt  NKLFRcflrc
       HSV1  159   raptpSaPSP  namlrrsvRq  aqrrssarWt  PDlgymrqcl  NqLFRvlrve
       VZV    26   kmEYGSaPgP  lngR.dtsRG  PGAFCtpgWe  ihpaRLveDl  NRvFlclaqS
       PRV    55   HPEYGppPdP  eevRvhgaRG  PGAFCaaPWr  PDtrRLgaDv  NRLFPglavS
       EHV4   51   HPEYGlplSP  rslRpylsRG  PGAFCapPWr  PDvnRLagDv  NRLFRglstS
       cons  3/5   HPEYGS-PSP  ---R----RG  PGAFC--PW-  PQ--RL--D-  NRLFR-I--S
             4/5      ***         *         * **          ** **      * ***
             5/5                                           *             * *

US10   MDV    47   ArtiLtaati  sqaAm..kag  kPPssrLwG.  ..eifdrmtv  tlneydisas
       HSV1  192   frtyvevSrm  c.aAnvrdpp  pPatgamlGr  harlvhtqwl  ranq...ets
       VZV    41   AaalcaiSte  AyeAfihsps  erPcaslwGr  akdafgrmcg  ela....adr
       EHV4   80   AsavramSad  aadAlrrgag  pPPeiqpra.  ....yrmfce  lfgryavspm
       cons  3/4   A------S--  ---A------  -PP-----G-  ----------  ----------
             4/4                    *

US2    MDV    1    MGVsmITiVT  LLDecdRLPg  rSrDAastLW  lF........  LikQCmeqiq
       HSV1   1    MGVvvvnVmT  LLDqnnaLPr  tSvDAsPaLW  sF........  LlrQCRilas
       PRV    1    MGVtalTVVT  LmDgsgRiPa  fvgeAhPdLW  kvltewcyas  LvqQrRaade
       cons  2/3   MGV--ITVVT  LLD---RLP-  -S-DA-P-LW  -F--------  L--QCR----
             3/3    ***         *   *  *    *   * **    *             *  *

US3    MDV   179   gPLplnqlit  leRglLgALa  YiHekgIIHR  DvKtENIFld  kPenVvLGDF
       HSV1  275   nPLgrpqlaa  vsRqlLsAvd  YiHrqgIIHR  DiKtENIFin  tPediCLGDF
       VZV   177   n.Lpicdlla  iqRsvLrALq  YlHnnsIIHR  DiksENIFin  hPgdVCvGDF
       PRV   193   gPLdmrdagr  viRsvLrgLa  YlHgmrImHR  DvKaENIFle  dvdtVCLGDl
       cons  3/4   -PL----I--  --R--L-AL-  Y-H---IIHR  D-K-ENIF--  -P--VCLGDF
             4/4      *                *     *  * **   * * ****          **

US6    MDV   114   YdalVAWFvl  graCgrPIYL  rEYanCstne  pFGtCklksl  gwWdrryAmt
       HSV1  118   YnltiAWFrm  ggnCAIPity  mEYteCsynk  slGaCplRTq  PrWn.yydsf
       PRV    92   YrAhVAWyrI  adgCAhllyf  iEYadCdPrq  vFGrCrrRTt  PmWwtpsAdy
       EHV1  113   YsArltWFkI  mptCAtPIhd  vsYmkCnPkl  sFamCdeRsd  llWqaslltm
       BHV1  101   YnAtViWykI  esgCArPLYy  mEYteCePrk  hFGyCryRTp  PfWdsflAgf
       cons  3/5   Y-A-VAWFPI  ---CA-PIY-  -EY--C-P--  -FG-C--RT-  P-W----A--
             4/5   *  *           **  *     **  * **   * *   *      *
             5/5      *             *            *       *              *

US7    MDV    47   vrGqLLFLGd  Qtrts.sYtG  ttEiLkwOee  ykCYsVlhat  sYmdCPaida
       HSV1   53   llGeLrFvGd  QvPhtTyYdG  gvELwhypmg  hkCprVvhvv  tvtaCPRrpa
       VZV    51   IkGqLvFiGe  QlPtgTNYSG  tlELLyaDtv  afCfrsvqvi  rYdgCPRIrt
       PRV    59   IdGtLLFLeg  psPs..NYSG  rvELLrlDpk  raCYtreyaa  eYdlCPRvhh
       EHV1   51   LvGhLLFLdg  QrlptTNYSG  LiELihynys  svCYtVlqtl  sYesCPRvan
       cons  3/5   I-G-LLFLG-  Q-P---TNYSG  --ELL--D--  --CY-V----  -Y--CPR---
             4/5    * **   *     *   **       * *       *  *        *   ***
             5/5    * *          *            *                         **

US8    MDV   232   CkfvtiYEpC  IfHPkePECi  ttaeqsvChF  aSnidllqiA  aarseNCSt.
       HSV1  271   CaemRiYESC  IYHPqlPECL  sPa.dapCaa  st..wtsrlA  vRsYagCSrt
       VZV   387   CqpmRlYstC  lYHPnAPqCL  shmns.qCtF  TSPhlAqrvA  stvYqNCeha
       PRV   274   CllyyvYEpC  IYHPrAPECL  rP.vdpaCsF  TSParAalvA  rRaYasCSpl
       EHV1  249   CdlfRvfEtC  IfHPtAmaCL  hP.eqhtCsF  TSPirAtkll  hRvYqNCSdh
       cons  3/5   C---R-YE-C  IYHP-APECL  -P-----C-F  TSP--A---A  -R-Y-NCS--
             4/5        *  **   ** ** ***    *      *   *    *     **  * **
             5/5        *        *   * *              *                 *
```

FIG.3A-1

```
rlnsgpfhda  LRRaLfDihm  iGrmgyRlkq  aeWetimnLt  PrQS.lhLRr  127
rdphgsanr.  LRhlirDcYL  MGYcRaRlap  rtWcrLLQys  ggtwgmhLRn  257
sgrVTrDsRr  LRRicIDFYl  MGrTRqRPtl  aCWeeLLQLg  PtQtq.cLRa  123
aadVTgDtRa  LRRaLfDFYa  MGYTRqRPsa  pCWgaLLQLs  PeQSa.pLRs  153
slhVTeDsRv  LRRyLlDFYa  MGYThaRPtl  eCWgaLLQLm  PeQS.lpLRn  149
---VT-D-R-  LRR-L-DFY-  MGYTR-RP--  -CW--LLQL-  P-QS---LR-  60%
            ***  *  *   **  *       *  ****    *  *    **  35%
             **     *     *     *        *           **    11%

P.fhptdPtR  kiVgraLrci  erapl.TheE  mdtRftimmy  WCCLGHAgyC  139
Plw.....pW  Rtaainfitt  maprvqTHrh  mhdlLmacAf  WCCLtHAstC  283
qrppsvpPir  RaVlslLreq  CmpdpqsHlE  lseRLilmAy  WCCLGHAgip  135
PvfhsadPlR  RaVgryLvdl  gaapveTHaE  lstRLlfcAh  WCCLGHAfgC  174
P------P-R  R-V---L---  ------TH-E  ---RL---A-  WCCLGHA--C  26%
                                 *              ****  **    8%

DdvGvPiiaR  aAdLfRfakP  mliLPRqhRP  IVRTkppdgt  gvrgTGLagt   92
eplGtpVVvR  pAnLrRlAeP  LmdLPkpTRP  IVRTRScrcp  PnttTGLfaE   92
DtprqhVVlR  ssei..apgs  LalLPRaTRP  vVRTRSdpta  PfyiTtethE   98
D--G-PVV-R  -A-L-R-A-P  L--LPR-TRP  IVRTRS----  P---TGL--E  54%
    *        **    **     **  **   ***              *      21%

GAACkldeht  dkPkcYGwsG  TleTNsPEIL  AIDPYcTktD  IWSAGIVLFE  278
GAACfvqgsr  ssPfpYGlAG  TidTNaPEvL  AgDPYtTtVD  IWSAGIViFE  374
GAACf.pvdi  nanryYGwAG  TlaTNsPEIL  ArDPYgpaVD  IWSAGiVLFE  274
GAArcnvaa.  ..PnfYGlAG  TleTNaPEvL  ArDrYdTkVD  vWgAGvVLFE  289
GAAC------  --P--YG-AG  TI-TN-PE-L  A-DPY-T-VD  IWSAG-VLFE  58%
*           *    ** * *    * *  *  **  * *  * **   38% syldrDELkL  liAAPsRels  GlYtRLiiin  GepissDill  tv..kGtCsF  211
savseDnLGf  lMhAPAfeta  GtYIRLvkin  dwteITqFil  ehrakGsCky  216
mfpTeDELGL  lMvAPgRfne  GqYRRLvsvD  GvnIITDFmV  alPegqeCpF  191
aaeTdDELGL  vlAAPAhsas  GlYRRvieID  GrrlyTDFsV  tiP.serCpi  211
aypTdDELGL  iMAAPARlve  GqYRRalyID  GtvayTDFmV  slPa.GdCwF  199
---T-DELGL  -MAAPAR---  G-YRRL--ID  G--I-TDF-F  --P--G-C-F  53%
    *****       **       * *          ***           *      30%
              *   **    *  *                      *        16% tvFRgCR..d  avvYaqphgR  VqpfpEkgtL  LrIvePrvsD  tGsYyiRVsL  143
vAFalCRatd  S.thspaypt  lelnlagqpL  Lrvqratrdy  AGvYVLRVwv  151
SAFIsCRykh  SwhYgnstdR  istepdagvm  LkItkPginD  AGvYVLIVrL  150
eAFRgClrKr  eplarrasaa  V....EarrL  LfvsrPappD  AGsYVLRVrv  152
nAFRsClhKt  SkhY.hdyfR  VnasvEtnyL  LnItkPqptD  sGaYiLRVkL  149
-AFR-CR-K-  S--Y-----R  V----E---L  L-I--P---D  AG-YVLRV-L  49%
 **  *                  *     *    *    *     * *    ***   26%
    *                                                 *     15%

....gyrRCi  ydtaidesvq  arltfiepgi  psfkmkDvqv  ddaGLYVvVa  326
nppp...RCs  aeahmepvp.  ..glawqaas  vnLeFrDasp  qhSGLYlcVv  361
dnytay..Cl  gishmep...  sfgillhdgg  ttLkFvDtpe  slSGLYVfVv  480
lgdrwltaC.  ..........  .....pfdaf  geevhtnata  deSGLYV1Vm  356
gns.wpsRCh  stllgnrlyf  iq...paqnr  vdLlFkDtpa  satGLYVfVl  343
-------RC-  ----------  ----------  --L-F-D---  --SGLYV-V-  35%
       *                                         ****  *   24%
          *                               *           ***  * 14%
```

FIG. 3A-2

FIG. 3B-2

MAREK'S DISEASE HERPESVIRUS DNA SEGMENT ENCODING GLYCOPROTEINS, GD, GI AND GE

CROSS-REFERENCE TO RELATED APPLICATION

This application is a continuation-in-part of U.S. application Ser. No. 07/572,711, filed Aug. 24, 1990, now U.S. Pat. No. 5,138,033.

BACKGROUND OF THE INVENTION (1) Field of the Invention

The present invention relates to segments of the Marek's Disease Herpesvirus genome, from its unique short ($U_S$) region encoding glycoproteins gD, gI and gE, and to novel glycoproteins produced therefrom. In particular, the present invention relates to DNA segments containing genes encoding these glycoprotein antigens and containing potential promoter sequences up to 400 nucleotides 5' of each gene, segments which are useful for probing for Marek's disease herpesvirus, as a possible source for Marek's disease virus (MDV) promoters, for gene expression to produce the glycoproteins that in turn can be used for producing antibodies which recognize the three glycoprotein antigens, and in the case of the latter two genes, for potential insertion sites for foreign genes and as possible sites for gene inactivation to attenuate MDV field isolates for vaccine purposes.

(2) Prior Art

MDV is an oncogenic herpesvirus of chickens, which is known to cause T cell lymphomas and peripheral nerve demyelination. The resulting disease, Marek's disease (MD), was the first naturally occurring lymphomatous disorder to be effectively controlled via vaccination, using either the antigenically related, yet apathogenic, herpesvirus of turkeys (HVT) or attenuated field isolates of MDV.

Because of similar biological properties, especially its lymphotropism, MDV has been classified as a member of the gammaherpesvirus subfamily (Roizman, B., et al., Intervirology 16:201–217 (1981)). Of the three herpesvirus subfamilies, gammaherpesviruses exhibit particularly marked differences with regard to genome composition and organization. For example, the B-lymphotropic Epstein-Barr virus (EBV) of humans has a 172.3 kbp genome with 60% G+C content, is bounded by terminal 0.5 kbp direct repeats and contains a characteristic set of internal 3.07 kbp tandem repeats (Baer, R., et al., Nature (London) 310:207–211 (1984)). Herpesvirus saimiri (HVS), a T-lymphotropic herpesvirus of new-world monkeys and lower vertebrates, has an A+T rich coding sequence (112 kbp; 36% G+C; i.e. L-DNA) without any large-scale internal redundancy, but contains instead greater than 30 reiterations of a 1.44 kbp sequence of 71% G+C at the termini of the genome (H-DNA) (Banker, A. T., et al., J. Virol. 55:133–139 (1985)). Despite the structural differences between EBV and HVS, the genomes of these two viruses encode serologically related proteins and share a common organization of coding sequences which differs from that of the neurotropic alphaherpesviruses, exemplified by herpes simplex virus (HSV) and varicella-zoster virus (VZV) (Camerion, K. R., et al., J. Virol. 61:2063–2070 (1987); Davison, A. J., et al., J. Gen. Virol. 68:1067–1079 (1987); Davison, A. J., et al., J. Gen. Virol. 67:597–611 (1986); Davison, A. J., et al., J. Gen. Virol. 76:1759–1816 (1986); Davison, A. J., et al., J. Gen. Virol. 64:1927–1942 (1983); Gompels, U. A., J. of Virol. 62:757–767 (1988); and Nichols, J., of Virol. 62:3250–3257 (1988)).

In contrast to other gammaherpesviruses, MDV has a genome structure closely resembling that of the alphaherpesviruses (Cebrian, J., et al., Proc. Natl. Acad. Sci. USA 79:555–558 (1982); and Fukuchi, K., et al., J. Virol. 51:102–109 (1984)). Members of the latter subfamily have similar genome structures consisting of covalently joined long (L) and short (S) segments. Each segment comprises a unique (U) segment ($U_L$, $U_S$) flanked by a pair (terminal and internals) of inverted repeat regions ($TR_L$, $IR_L$; $TR_S$; respectively). Alphaherpesviruses include human HSV and VZV, porcine pseudorabies virus (PRV), bovine herpesvirus (BHV) and equine herpesvirus (EHV). Because MDV contains extensive repeat sequences flanking its $U_L$ region, its genome structure most resembles that of HSV (Cebrian, J., et al., Proc. Natl. Acad. Sci. USA 79:555–558 (1982); and Fukuchi, K., et al., J. Virol. 51:102–109 (1984)).

Recent studies (Buckmaster, A. E., et al., J. Gen. Virol. 69:2033–2042 (1988)) have shown that the two gammaherpesviruses, MDV and HVT, appear to bear greater similarity to the alphaherpesviruses, VZV and HSV, than to the gammaherpesvirus, EBV. This was based on a comparison of numerous randomly isolated MDV and HVT clones at the predicted amino acid level; not only did individual sequences exhibit greater relatedness to alphaherpesvirus genes than to gammaherpesvirus genes, but the two viral genomes were found to be generally collinear with VZV, at least with respect to the unique long ($U_L$) region. Such collinearity of $U_L$ genes extends to other alphaherpesviruses such as HSV-1, HSV-2, EHV-1 and PRV as evidenced by both sequence analysis (McGeoch, D. J., et al., J. Gen. Virol. 69:1531–1574 (1988)) and DNA hybridization experiments (Davison, A. J., et al., J. Gen. Virol. 64:1927–1942 (1983)). Many of these $U_L$ genes are shared by other herpesviruses, including the beta- and gammaherpesviruses (Davison, A. J., et al., J. Gen. Virol. 68:1067–1079 (1987)). The organization and comparison of such genes has suggested the past occurrence of large-scale rearrangements to account for the divergence of herpesviruses from a common ancestor. Unfortunately, such a hypothesis fails to account for the presence of alphaherpesvirus S component (unique short, $U_S$, and associated inverted/terminal repeat short, $IR_S$, $TR_S$) genes which appear unique to members of this subfamily (Davison, A. J., et al., J. Gen. Virol. 68:1067–1079 (1987); Davison, A. J., et al., J. Gen. Virol. 67:597–611 (1986); and McGeoch, D. J., et al., J. Mol. Biol. 181:1–13 (1985)).

The DNA sequence and organization of genes in a 5.5 kbp EcoRl fragment mapping in the $U_S$ region of MDV strain RBIB was described by Ross, Binns and Pastorek (Ross, L. J. N., et al, Journal of General Virology 72:949–954 (1991)). The properties and evolutionary relationships of four of the predicted polypeptides was also described (Ross, L. J. N. and M. M. Binns, Journal of General Virology, 72:939–947 (1991)). In that fragment they found the homologs of HSV US2, US3, US6 (gD) and US7 (gI), as well as an MDV specific gene. For the latter, only part of the gene was present. These reports confirm the presence of four MDV $U_S$ genes, and the evolutionary relationship proposed above. It is important to note that no evidence for US8 (gE), or the genes to the left of US2 were described.

In addition to its uniqueness compared with beta- and gammaherpesviruses, the alphaherpesvirus $U_S$ region is particularly interesting because of marked differences in its content and genetic organization within the latter subfamily (e.g. HSV-1 $U_S$=13.0 kbp, 12 genes, McGeoch, D. J., et al., J. Mol. Biol. 181:1–13 (1985)); VZV $U_S$=5.2 kbp, 4 genes, Davison, A. J., et al., J. Gen. Virol. 76:1759–1816 (1986)). In the case of HSV-1, 11 of the 12 $U_S$ genes have been found to be dispensable for replication in cell culture (Longnecker, R., et al., Proc. Natl. Acad. Sci. USA 84:4303–4307 (1987)). This has suggested the potential involvement of these genes in pathogenesis and/or latency (Longnecker, R., et al., Proc. Natl. Acad. Sci. USA 84:4303–4307 (1987); Meignier, B., et al., Virology 162:251–254 (1988); and Weber, P. C., et al., Science 236-576–579 (1987)). In the report by Buckmaster et al. (Buckmaster, A. E., et al., J. Gen. Virol. 69:2033–2042 (1988)), except for the identification of partial MDV sequences homologous to HSV immediate early protein alpha 22 (US1) and the serine-threonine protein kinase (US3), the content, localization and organization of MDV S component homologs was not determined. Moreover, despite the presence of at least four HSV $U_S$ glycoprotein genes (two in VZV), no such homologs were identified.

In application Ser. No. 07/229,011 filed Aug. 5, 1988, (now abandoned) including Leland F. Velicer, one of the present inventors, the Marek's Disease herpesvirus DNA segment possibly containing the gene encoding the glycoprotein B antigen complex (gp100, gp60, gp49) was identified but not sequenced. Antigen B is an important glycoprotein complex because it can elicit at least partial protective immunity, and thus MDV DNA segment can be used for probes, as a possible source for promoters in the gene's 5' regulatory region, and for gene expression to produce the glycoproteins, which in turn can be used to produce antibodies that recognize the glycoprotein antigens. However, there was no discussion of the glycoproteins of the present invention. These B antigen glycoproteins are not encoded by the $U_S$ region and thus are from a different region of the MDV genome.

In application Ser. No. 07/526,790, filed May 17, 1987 (now abandoned) by Leland F. Velicer, the MDV herpesvirus DNA segment containing the gene encoding the glycoprotein A antigen (gp57–65) is described but not sequenced. This MDV DNA segment is useful as probes, as a possible source for promoters in the gene's 5' regulatory region, and for producing antibodies by the sequence of events described above. This DNA is also important because antigen A is now known to be a homolog of HSV gC, a gene non-essential for replication in cell culture. Since that property most likely also applies to the MDV homolog, it may be useful as a site for insertion of foreign genes. However, there was no discussion of the glycoproteins of the present invention. This glycoprotein is also not encoded by the $U_S$ region and is thus from a different region of the MDV genome.

Other glycoproteins are encoded by Marek's disease herpesvirus genome. In application Ser. No. 07/572,711, filed Aug. 24, 1990 (now U.S. Pat. No. 5,138,033) by Leland F. Velicer, et al., the MDV DNA containing the genes encoding the MDV, gD, gI and part of gE glycoproteins is described, with MDV nucleotide sequences for the complete gD and gI genes and part of gE (MDV homologs of HSV genes US6, US7, US8, respectively). This MDV DNA segment is useful as probes, as a possible source for promoters in the gene's 5' regulatory region, and for producing antibodies by the sequence of events described above. The present invention is particularly directed to the complete gene (US8) encoding glycoprotein gE.

OBJECTS

It is an object of the present invention to provide sequenced DNA encoding glycoproteins gD, gI and gE, both together and individually. It is further an object of the present invention to provide DNA segments encoding these glycoprotein antigens and containing potential promoter sequences up to 400 nucleotides 5' of each gene; which are useful as DNA probes, as a possible source for MDV promoters, for producing antibodies which recognize the antigens and, in the case of the latter two glycoproteins, as insertion sites for foreign genes and as possible sites for gene inactivation to attenuate MDV field isolates for vaccine purposes. These and other objects will become increasingly apparent by reference to the following description and the drawings.

IN THE DRAWINGS

FIGS. 1A to C show map location, sequencing strategy and organization of MDV open reading frames (ORFs):

FIG. 1A includes MDV genomic structure and restriction maps outlining area sequenced.

FIG. 1B includes map location and sequencing strategy. Boxes define plasmid clones with BamHI, EcoRI or SalI-bound inserts that were used to generate M13mp18 and −19 templates for DNA sequencing. Rightward and leftward arrows define sequences derived from the top and bottom strands, respectively. The restriction enzyme sites are identified as: B=BamHI, E=EcoRI, Nc=NcoI, Ns=NsiI, S=SalI, and P=PstI. Sequences derived from random libraries (Sau3A, TaqI, RsaI), specific cloned restriction fragments, Bal 31-digested libraries or using synthetically-derived oligonucleotides are denoted by a, b, c, and d, respectively.

FIG. 1C includes organization of the MDV $U_S$ ORFs. Numbers refer to homologs based on relation to HSV-1 $U_S$ ORF nomenclature (McGeoch, D. J., et al., J. Mol. Biol. 181:1–13 (1985)). Boxes represent location of MDV ORFs. Arrows define direction of transcription/translation. Names of ORFs are displayed above boxes. Potential polyadenylation signals on the top and bottom strands are highlighted by AATAAA and AAATAA, respectively. SORF1 and SORF2 are MDV-specific S component ORFs given arbitrary names.

Figure 2A:
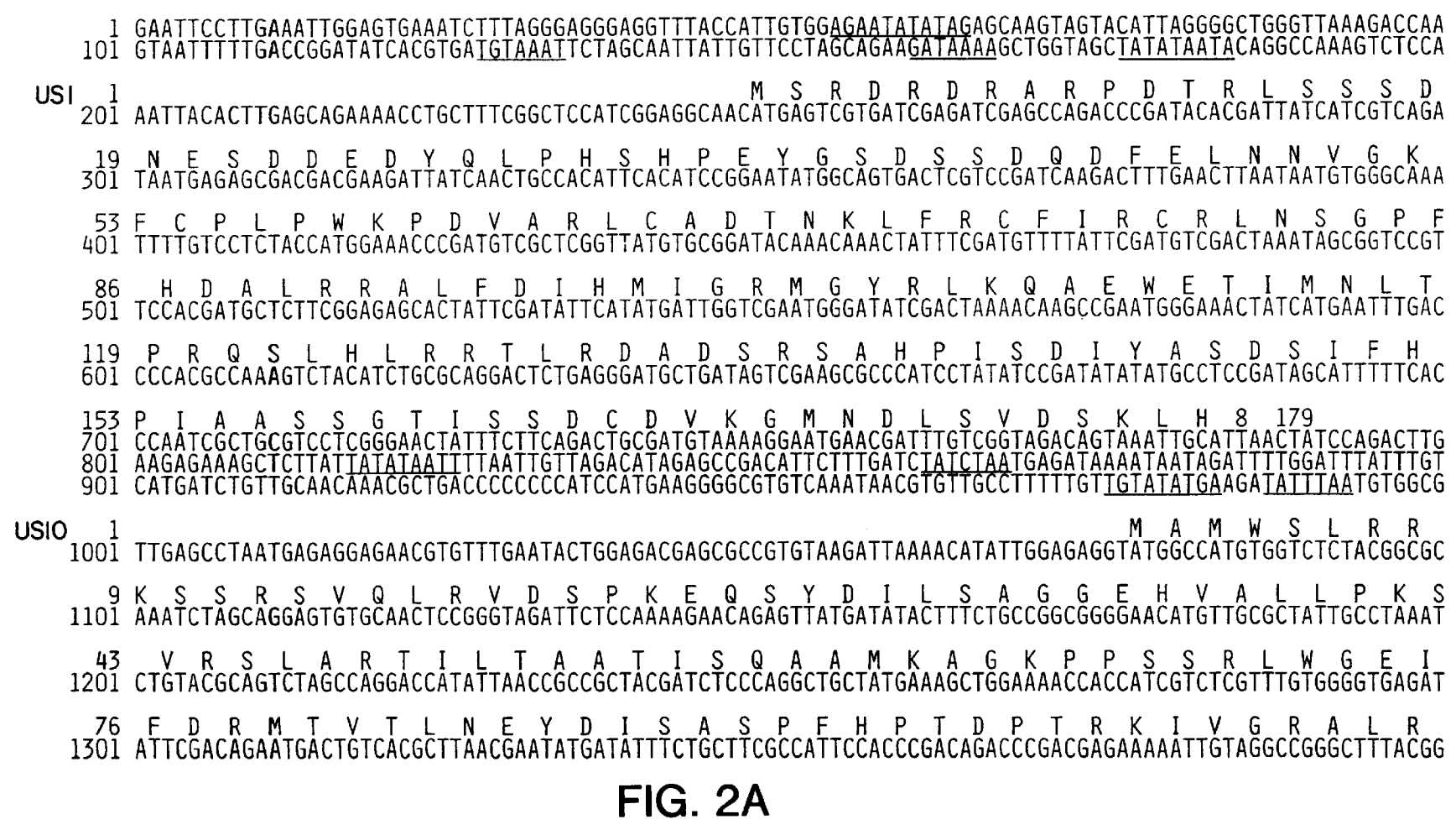
Figure 2B:
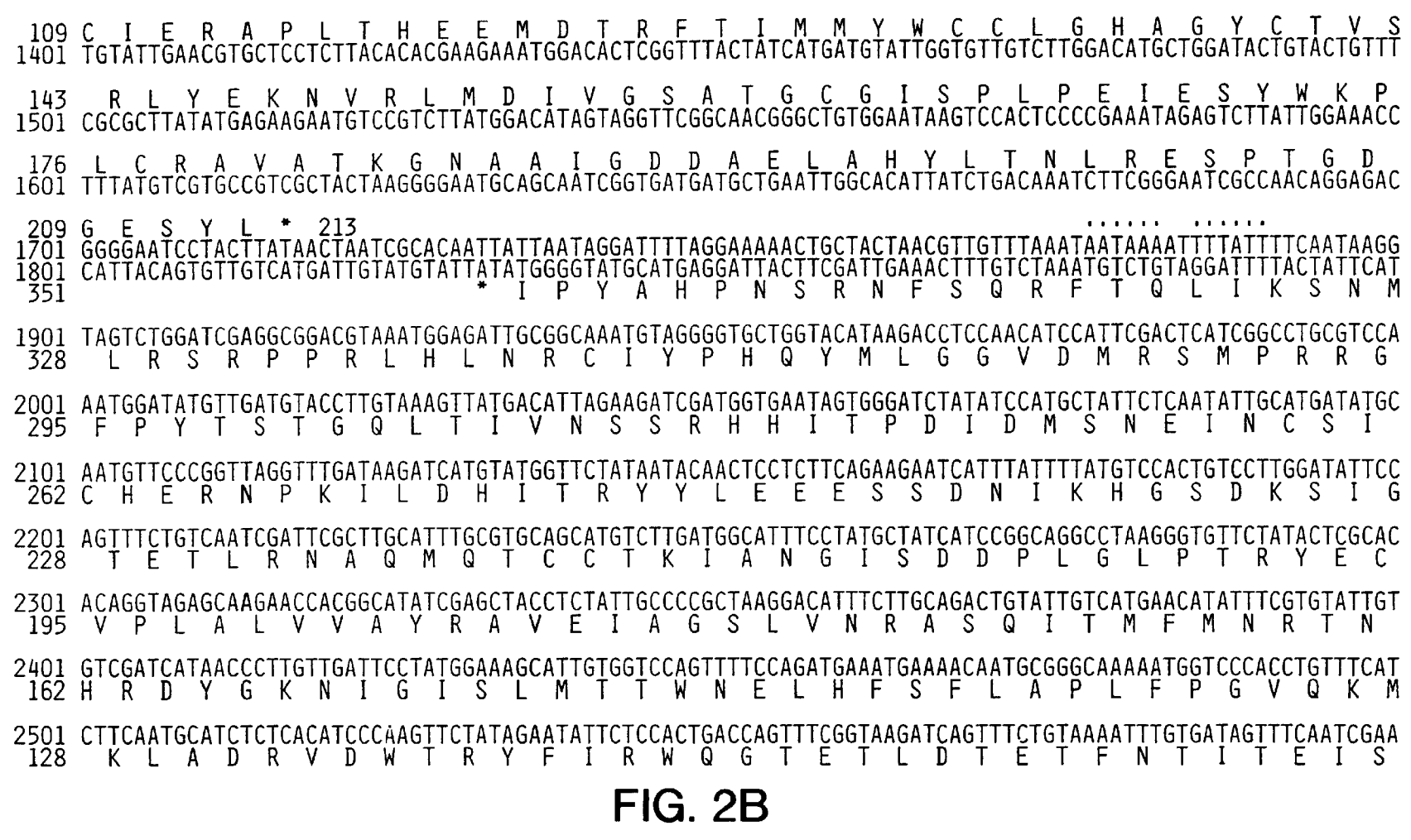
Figure 2C:
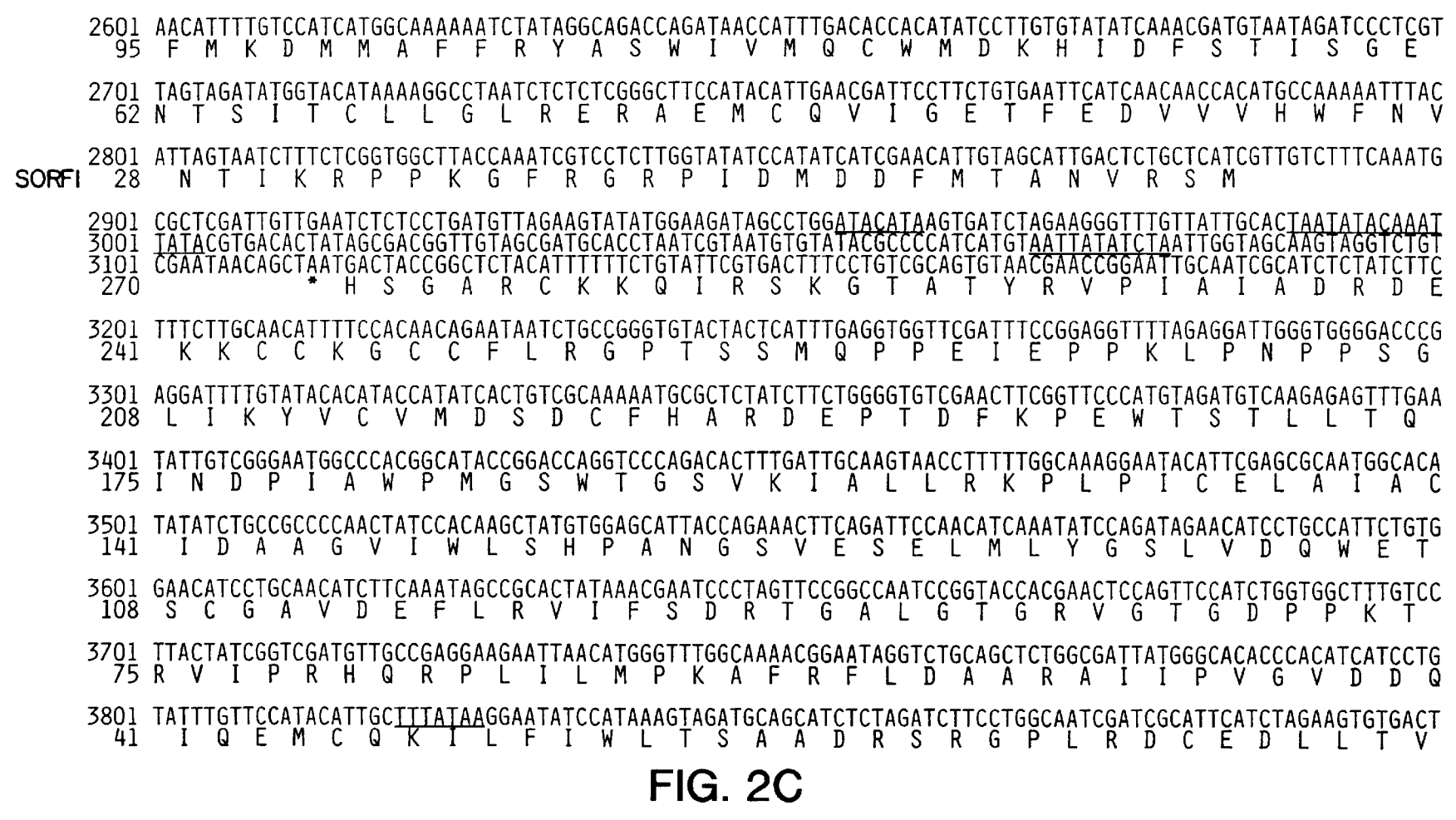
Figure 2E:
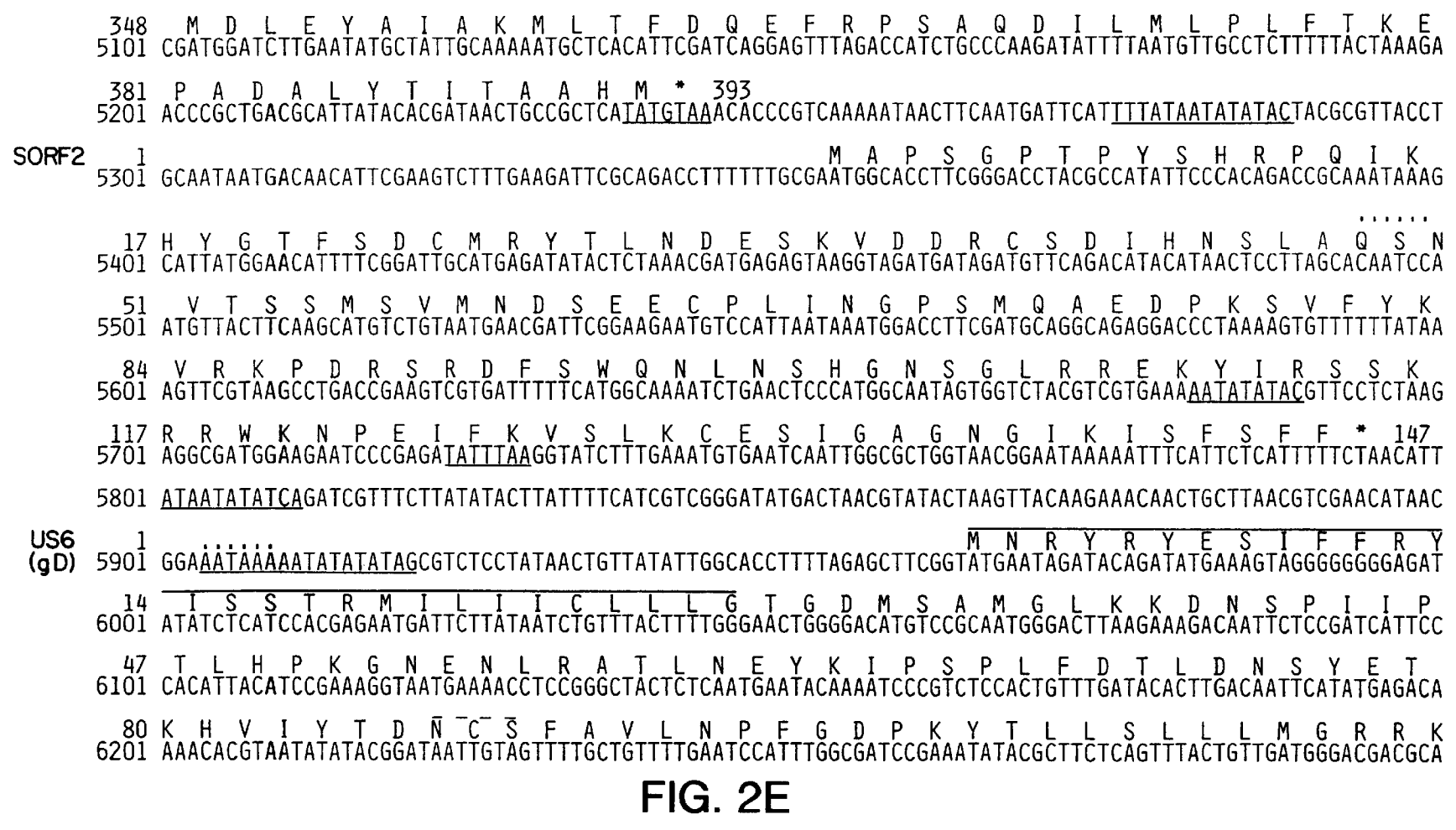
Figure 2F:
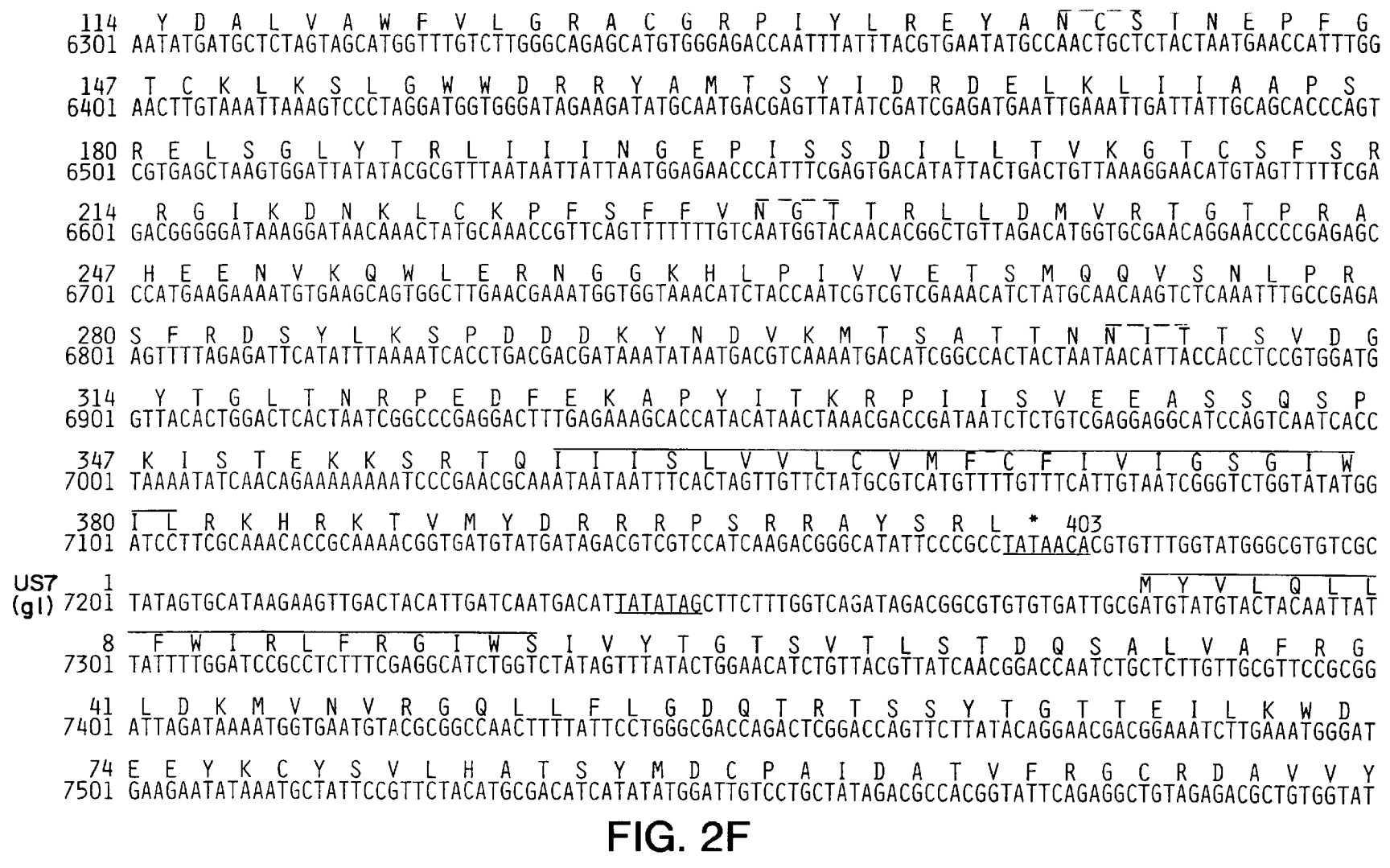
Figure 2G:
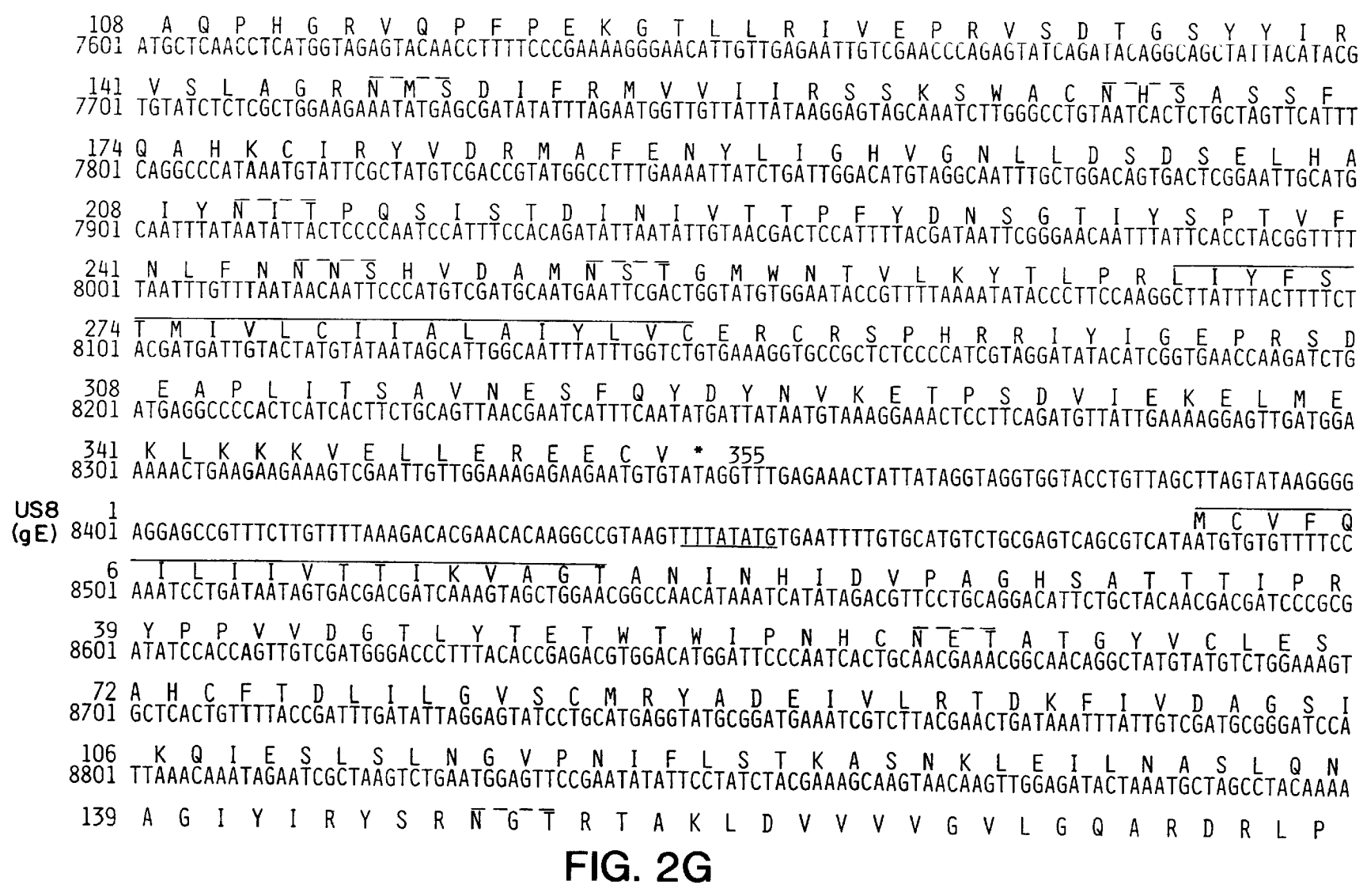
Figure 2H:
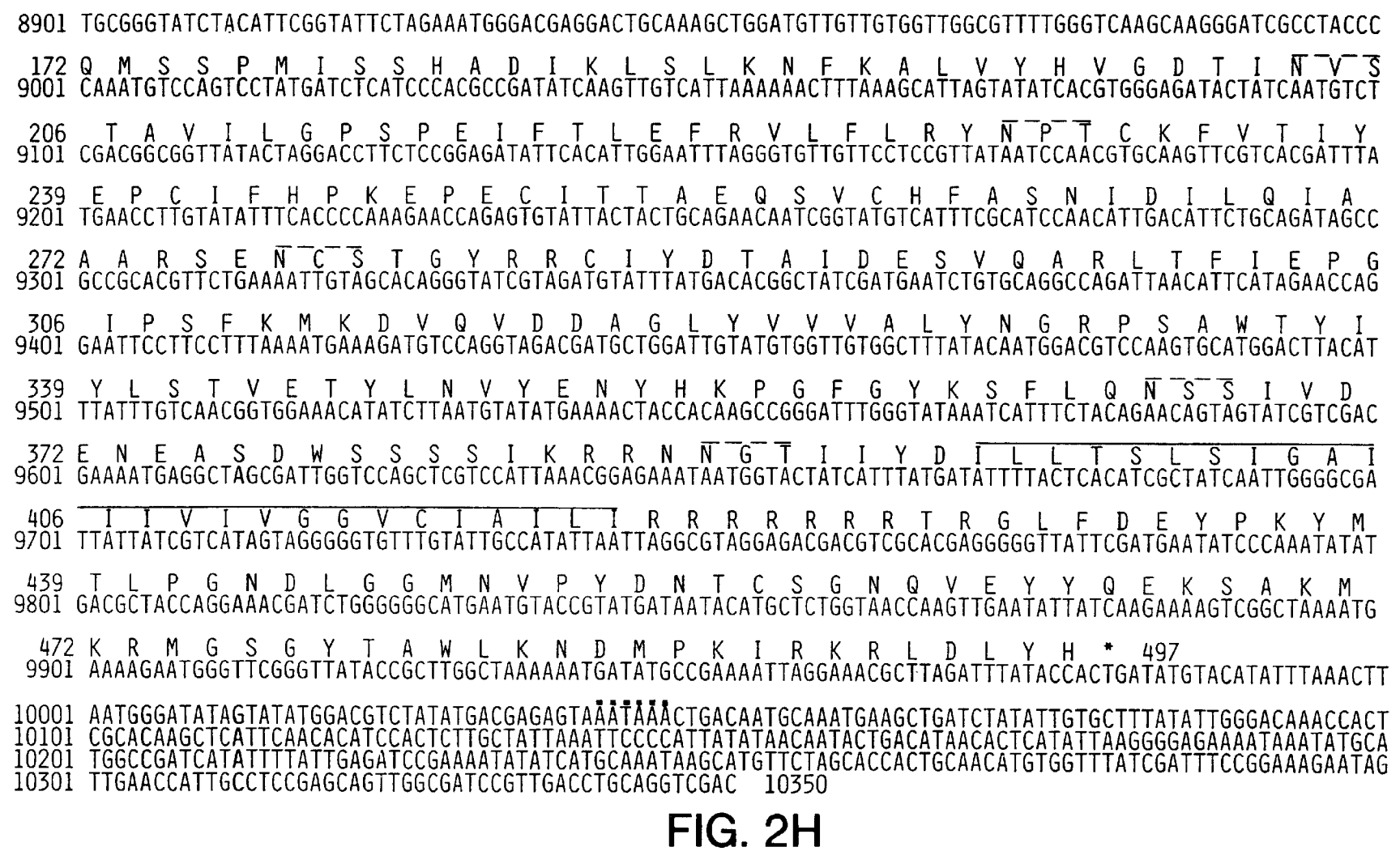

FIGS. 2A to 2H show nucleotide (SEO ID NO:1) and predicted amino acid sequences. The nucleotide sequence is given as the rightward 5' to 3' strand only (numbered 1 to 10350). Rightward- and leftward-directed predicted amino acid sequences are shown above and below the corresponding nucleotide sequences in single-letter code, respectively. The name of each ORF is given to the left of the first line of the amino acid sequence. Amino acid sequences are numbered from the first M (three letter code) (ATG in the DNA) at the N-terminus to the last amino acid at the C-terminus, which precedes the termination codon (identified by an *). Potential TATA consensus sites located within 400 nucleotides of the ATG are underlined and defined as sites containing at least six of seven matches to the TATA(AT)A (AT) consensus sequences defined by Corden et al. (Corden, B., et al., Science 209:1406–1414 (1980)). Underlines longer than seven nucleotides refer to areas containing overlapping TATA consensus sites.

FIGS. 3A-1 to 3A-2 show alignment of S component homologs showing selected regions displaying maximum amino acid conservation (SEO ID NO.:4–38). Gaps have been introduced to maximize alignment of identical amino acids as described in Methods. The consensus sequence (cons) indicates residues that are shared by at least all but one of the viruses and are indicated by capital letters. In alignments between more than two sequences, asterisks (*) indicate residues conserved by all of the viruses. Amino acid numbers (with respect to 5'-ATG) of corresponding regions aligned are listed before and after each sequence.

FIGS. 3B-1 to 3B-2 show the dot matrix analyses depicting overall homologies between selected MDV-alphaherpesvirus S segment homolog comparisons. Points were generated where at least 15 amino acids over a sliding window length of 30 were found identical or similar. The resulting diagonals illustrate regions showing greatest conservation. Amino acid numbers (with respect to 5'-ATG) of corresponding sequences are denoted above and to the right of each plot.

Figure 4:
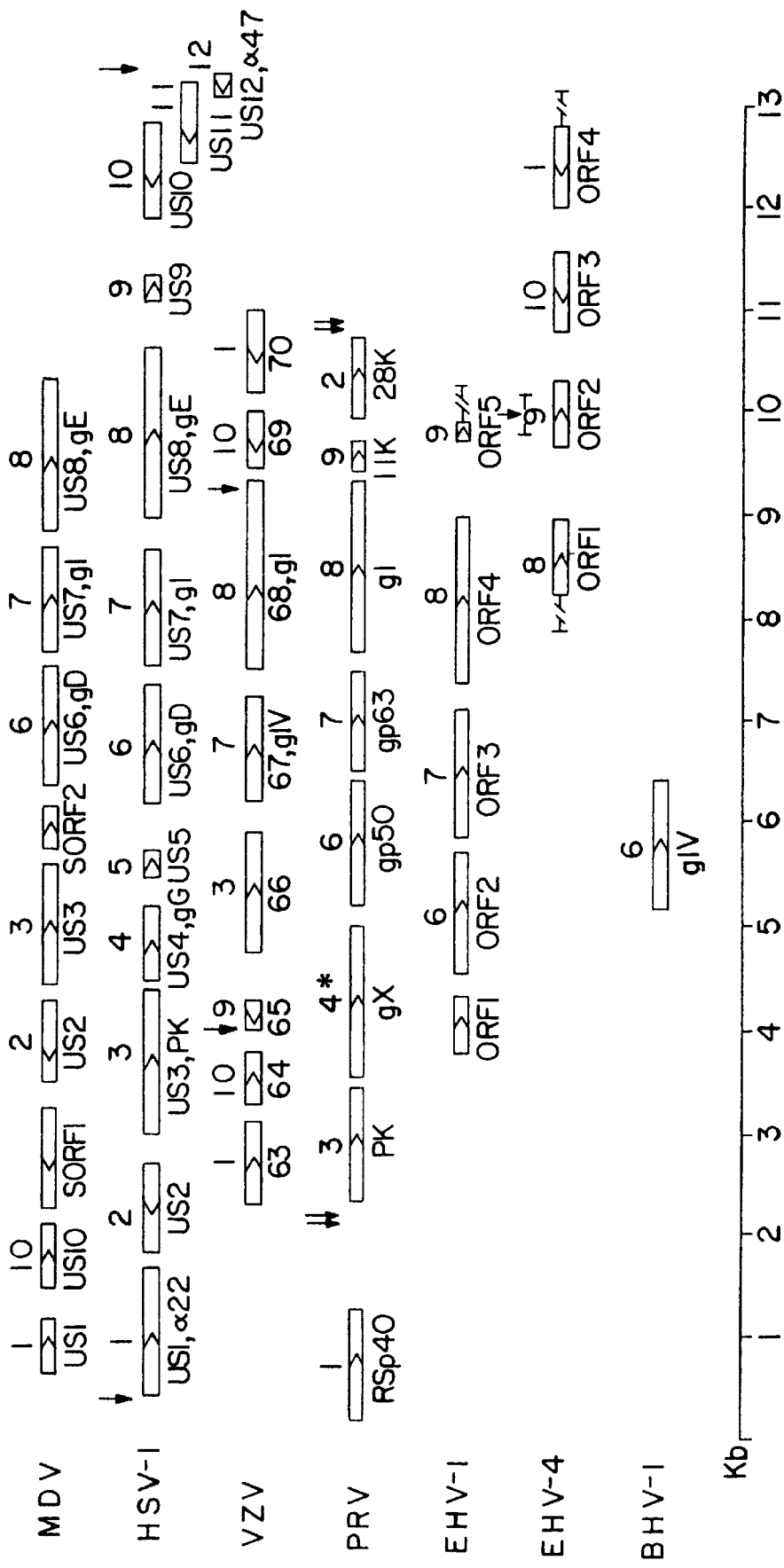

FIG. 4 shows a comparison of overall genome organization of available S component ORFs (Audonnet, J.-C., et al., J. Gen. Virol. 71:2969–2978 (1990); McGeoch, D. J., et al., J. Gen. Virol. 68:19–38 (1987); Tikoo, S. K., et al., J. Virol. 64:5132–5142 (1990), Van Zijl, M., et al., J. Gen. Virol. 71:1747–1755 (1990); Zhang, G., et al., J. Gen. Virol. 71:2433–2441 (1990); Cullinane, A. A., et al., J. Gen. Virol. 69:1575–1590 (1988); Davison, A. J., et al., J. Gen. Virol. 76:1759–1816 (1986); McGeoch, D. J., et al., J. Mol. Biol. 181:1–13 (1985); Petrovskis, E. A., et al., Virology 159:193–195 (1987); Petrovskis, E. A., et al., J. Virol. 60:185–193 (1986); and Petrovskis, E. A., et al., J. Virol. 59:216–223 (1986)). Numbers above each ORF refer to homologs based on relation to HSV-1 $U_S$ ORF nomenclature (McGeoch, D. J., et al., J. Mol. Biol. 181:1–13 (1985)). Alternative polypeptide designations common to each system are listed below those ORFs where applicable. Upper and lower case solid bars refer to rightward and leftward-directed ORFS, respectively. Arrows refer to identified $IR_S$-$U_S$ and/or $U_S$-$TR_S$ junction sites.

Figure 5:
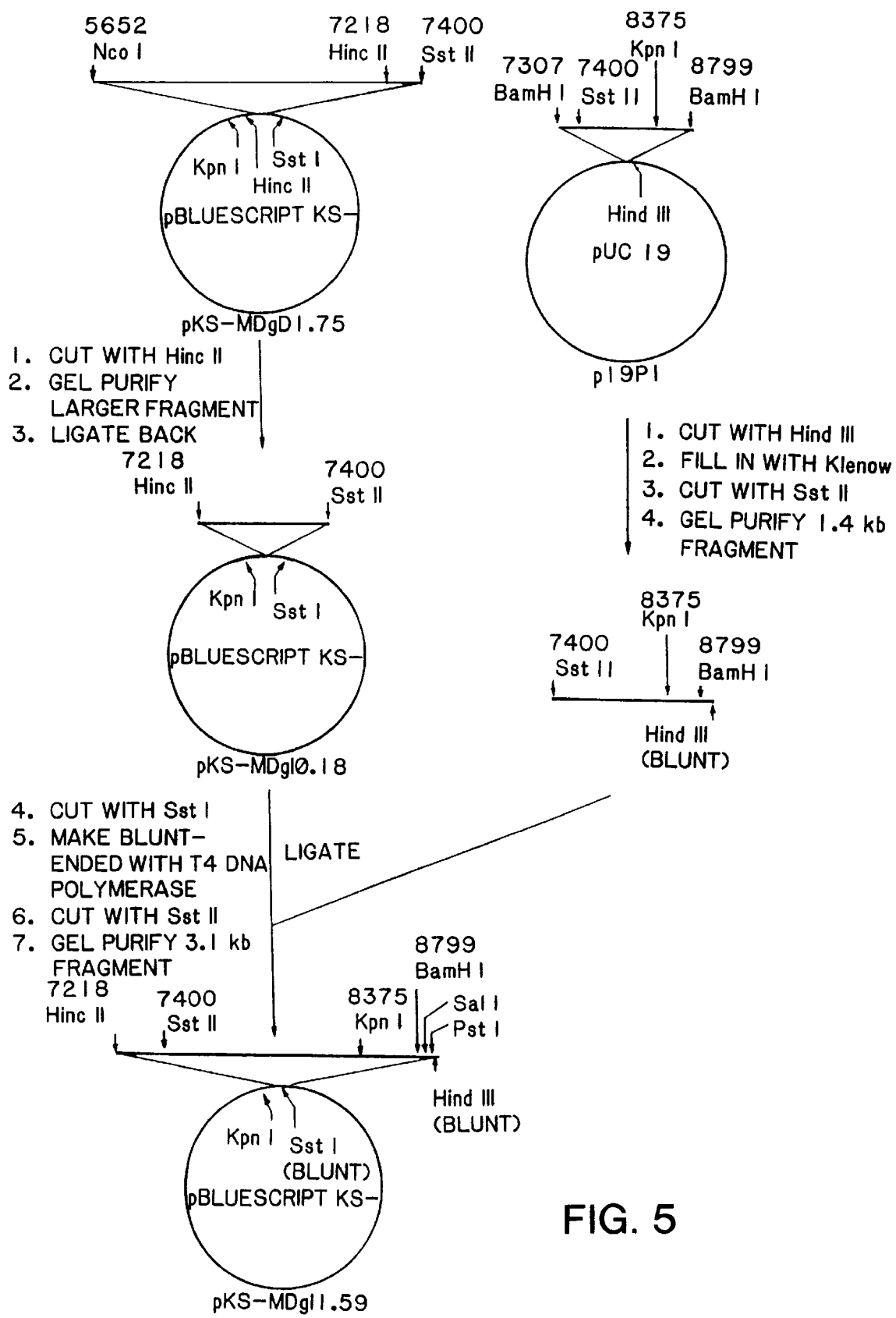

FIG. 5 shows the sequence of steps necessary to produce a complete segment of Marek's disease herpesvirus DNA encoding glycoprotein gI and the part of gE included in the application filed Aug. 24, 1990.

GENERAL DESCRIPTION

The present invention relates to a segment of DNA of Marek's disease herpesvirus genome encoding multiple glycoproteins, and containing potential promoter sequences up to 400 nucleotides 5' of each gene, between a 1 and 10350 nucleotide sequence as shown in FIGS. 2A to 2H (and identified as SEQ ID No:1).

Further, the present invention relates to an EcoRl I segment of Marek's disease herpesvirus genome encoding the glycoprotein D precursor, and subsegments of the DNA.

Further, still, the present invention relates to a segment of DNA encoding glycoprotein gD precursor between a 5964 and 7172 nucleotide sequence of Marek's disease herpesvirus DNA, and containing potential promoter sequences up to 400 nucleotides 5' of each gene, as shown in FIGS. 2A to 2H (and identified as part of SEQ ID No.:1) and subsegments of the segment of DNA which recognize the DNA.

The present invention also relates to a segment of DNA encoding glycoprotein gI precursor between a 7282 and 8346 nucleotide sequence of Marek's disease herpesvirus DNA, and containing potential promoter sequences up to 400 nucleotides 5' of each gene, as shown in FIGS. 2A to 2H (and identified as part of SEQ ID No:1) and subsegments of the segments that recognize the DNA.

The present invention also relates to a segment of DNA encoding glycoprotein gE precursor between a 8488 and 9978 nucleotide sequence of Marek's disease herpesvirus DNA, and containing potential promoter sequences up to 400 nucleotides 5' of each gene, as shown in FIGS. 2A to 2H (and identified as part of SEQ ID No:1) and subfragments of the DNA that recognize the DNA.

Further, the present invention relates to the novel glycoprotein precursors which are produced by expressions of the genes in the segments of DNA.

Further the present invention relates to the potential MDV gene promoters, which are located in the 400 nucleotides 5' of each coding sequence.

SPECIFIC DESCRIPTION

The present invention shows a sequence analysis of a 10.35 kbp DNA stretch encompassing a majority of the MDV $U_S$ region. Altogether seven MDV $U_S$ homologs, including three glycoprotein genes and two additional MDV-specific open reading frames, were identified.

EXAMPLE 1

Materials and Methods

Recombinant Plasmids, M-13 Subcloning and DNA Sequencing

MDV EcoRl-O and EcoRl-I of the pathogenic GA strain were previously cloned into pBR328 (Gibbs, C. P., et al., Proc. Natl. Acad. Sci. USA 81:3365–3369 (1984)), (Silva, R. F., et al., J. Virol. 54:690–696 (1985)) and made available by R. F. Silva, USDA Avian Disease and Oncology Lab, East Lansing, Mich., where these clones are maintained. GA strain BamHI-A and BamHI-P1 were previously cloned into pACYC184 and pBR322, respectively (Fukuchi, K., et al., J. Virol. 51:102–109 (1984)) and kindly provided by M. Nonoyama, Showa University Research Institute, St. Petersburg, Fla. GA strain clone GA-02, an EMBL-3 clone containing a partially digested MDV SalI insert, which contains BamHI-A, -P1, and additional 5' and 3' flanking sequences (kindly provided by P. Sondermeier, Intervet Intl. B. V., Boxmeer, The Netherlands) was used to extend analysis to the right of the above EcoRl and BamHl fragments. This phage clone was used to generate pUC18 subclones with smaller Sal I-bound inserts (psP18-A, pSP18-B, and pSP18-C) containing the 3' BamHI-P1-flanking region. These clones (FIG. 1B) were used to generate M13mp18 and –19 subclones for use as templates for nucleotide sequencing. Small- and large-scale plasmid preparations were made using the alkaline lysis procedure (Maniatis, T., et al., Molecular cloning: a laboratory manual. Cold Spring Harbor Laboratory, Cold Spring Harbor, N.Y. (1982)).

M13mp18 and M13mp19 phage subclones to be used as templates for sequencing were generated using specific restriction subfragments determined by restriction mapping or the use of Sau3A, Taq I or RsaI-digested viral DNA pools ligated into the unique BamHI, AccI or SmaI sites of M13 RF DNA, respectively. In some cases overlapping M13 deletion clones were obtained by processive Ba131 digestions from AccI, NaeI or NsiI restriction sites in EcoRl-O by the method of Poncz et al (Poncz, M., et al., Proc. Natl. Acad. Sci. USA 79:4298–4302 (1982)). Standard methods (Maniatis, T., et al., Molecular cloning: a laboratory manual. Cold Spring Harbor Laboratory, Cold Spring Harbor, N.Y. (1982)) were used for restriction digestions, gel electrophoresis, purification of DNA fragments from agarose gels, ligations and fill-in of 5' overhangs with Klenow fragment.

Ligated M13 products were transformed into $CaCl_2$-competent JM107 host cells and added to melted B top agar containing 10 l of 100 mM IPTG, 50 l of 2% X-gal and 200 l of a fresh overnight JM101 culture. These contents were then plated onto B agar plates and incubated at 37° C. overnight. Recombinant (clear) plaques were then used to infect 5 ml of YT media diluted 1:50 with an overnight JM101 culture and rotated at 37° C. for 6 hours. The resulting cells were pelleted by centrifugation for 5 minutes at room temperature and the supernatants were removed and stored at 4° C. to retain viral stocks of each recombinant clone.

Using the recovered supernatants, single-stranded M13 phage DNA to be used as templates for DNA sequencing by the dideoxy-chain termination method was isolated according to instructions in the M13 Cloning/Dideoxy Sequencing Instruction Manual provided by Bethesda Research Laboratories. Recombinant M13mp phages were further screened by electrophoresing purified single-stranded viral DNA on 1% agarose mini-gels and selecting those templates showing reduced mobility in comparison to single-stranded M13mp 18 control DNA.

DNA sequencing with single-stranded M13 templates was performed by the dideoxy-chain termination method (Sanger, F. S., et al., Proc. Natl. Acad. Sci. USA 74:5463–5467 (1977)) employing the modified T7 DNA polymerase, Sequenase™ (United States Biochemical Corp., Cleveland, Ohio). A summary of the sequencing strategy is included in FIG. 1B. For DNA sequencing reactions, the specific step by step instructions provided with the Sequenase™ sequencing kit were employed. Briefly, single-stranded M13 templates were first annealed with the universal M13 synthetic oligonucleotide primer by incubation at 65° C. for 2 minutes followed by slow cooling until the incubation temperature was below 30° C. Following the addition of proper mixtures of deoxy- and dideoxynucleotide triphosphates (dNTPs and ddNTPs, respectively), radioactively labeled deoxyadenosine 5'-(alpha-thio) triphosphate ($^{35}$S-dATP, 1000–1500 Ci/mmol; NEN-DuPont) and the Sequenase™ enzyme, synthesis of radioactively labeled complementary strands was initiated from the annealed primer. Four separate synthesis reactions were each terminated by the incorporation of the specific ddNTP (ddATP, ddGTP, ddTTP or ddCTP) used in each tube. Reaction products were electrophoresed through 7% polyacrylamide/50% urea/Tris-Borate-EDTA gels and the labeled chains were visualized by autoradiography. Both strands were sequenced at least once. This was facilitated by the use of 16 synthetic 17-mer olignonucleotides generated based on previously determined sequences and substituted for the universal primer under similar reaction conditions above (0.5 pmoles/reaction) according to the general approach described by Strauss (Strauss, E. C., et al., Anal. Biochem. 154:353–360 (1986)).

Analysis of Sequence Data

Sequences were assembled and analyzed on an IBM personal System 2/Model 50 microcomputer utilizing the IBI/Pustell (Pustell, J., et al., Nucl. Acids. Res. 14:479–488 (1986)) and Genepro (Version 4.10; Riverside Scientific Enterprises, Seattle, Wash.) sequence analysis software packages or programs obtained from the University of Wisconsin Genetics Computer Group (GCG; Devereaux, J., et al., Nucl. Acids. Res. 12:387–395 (1984)) and run on a VAX 8650 minicomputer. Database searches of the National Biochemical Research Foundation-Protein (NBRF-Protein, Release 21.0, 6/89) were made with the GCG program FASTA (Pearson, W. R., et al., Proc. Natl. Acad. Sci. USA 85:2444–2448 (1988)) which uses: (1) a modification of the algorithm of Wilbur and Lipman (Wilbur, W. J., et al., Proc. Natl. Acad. Sci. USA 80:726–730 (1983)) to locate regions of similarity; (2) a PAM250-based scoring system (Dayhoff, M. O., et al., p. 345–352. In M. O. Dayhoff (ed.), Atlas of protein sequence and structure, vol. 5, Suppl. 3. National Biomedical Research Foundation, Washington, D.C. (1978)) and (3) the alignment procedure of Smith and Waterman (Smith, T. F., et al., Adv. Appl. Mathematics 2:482–489 (1981)) to join together, when possible, the highest-scoring, non-overlapping regions in order to derive an alignment and its resulting, optimized score. Dot matrix homology plots were generated by using the GCG program DOTPLOT with the output file from GCG's COMPARE. The latter creates a file of the points of similarity between two predicted amino acid sequences for which a window length of 30 and a stringency of 15 (in which conservative amino acid replacements are scored positive) were chosen. Using the GCG program GAP, specific amino acid sequences were aligned using the algorithm of Needleman and Wunsch (Needleman, S. B., et al., J. Mol. Biol. 48:443–453 (1970)); following the insertion of gaps (to maximize the number of matches) the percentage of identical and similar amino acid residues were determined. To create multiple alignments using GAP, output files of gapped MDV sequences were created following successive GAP comparisons between the MDV sequence and its homologous sequences (in descending order of homology). These output files were used as input sequences for subsequent runs of GAP until the alignment of these gapped sequences could no longer be expanded by the addition of new gaps. Following alignment, the gapped output files were displayed and a consensus sequence calculated using the GCG program PRETTY. To achieve optimal results, in some cases manual editing was employed (using GCG's LINEUP).

Results

Figure 1B:
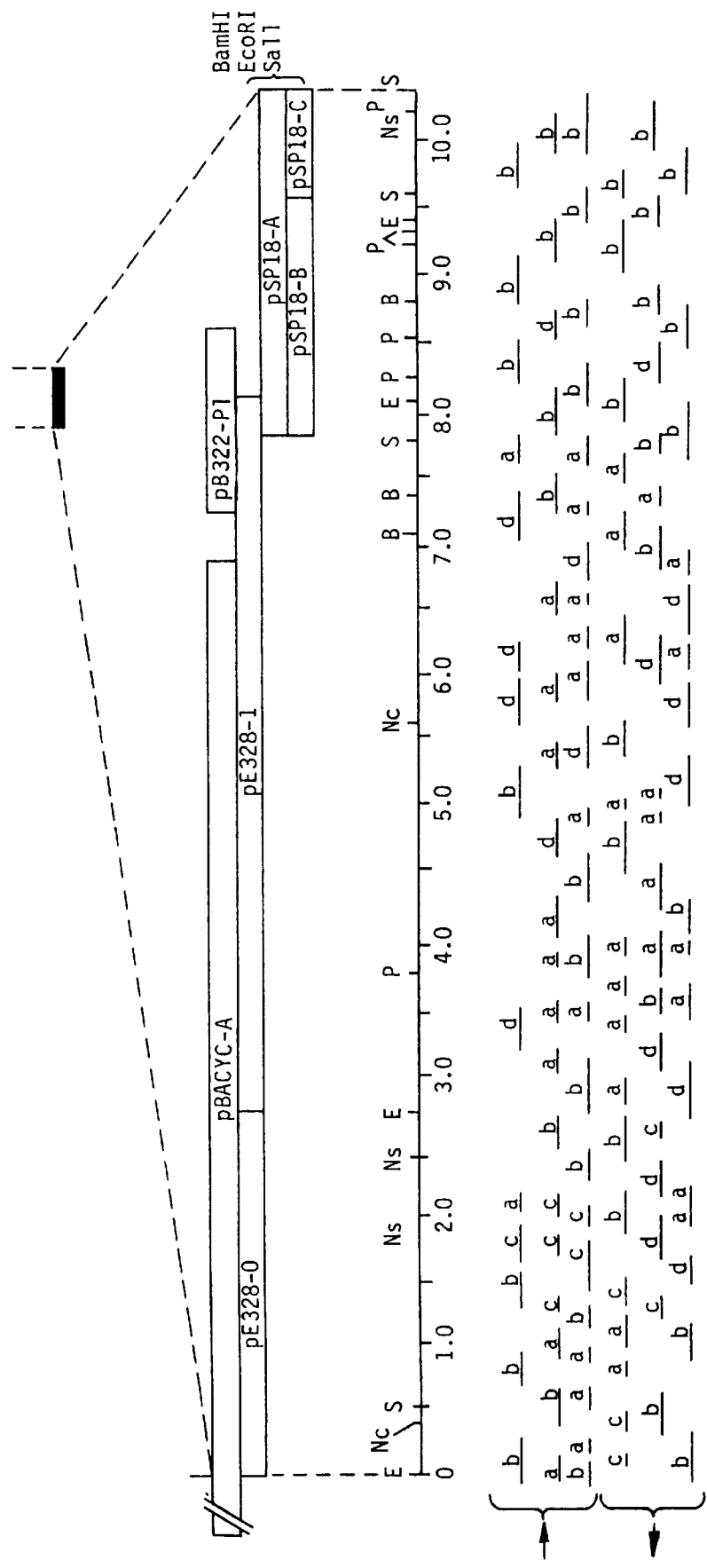

The 10,350 nucleotide DNA sequence presented FIGS. 2A to 2H appears to encompass a majority of the MDV (GA) genome's unique short ($U_S$) region. A summary of the sequencing strategy is included in Materials and Methods and is depicted in FIG. 1B. This sequence spans the $U_S$ fragments, EcoRl-O, EcoRl-I and extends to a SalI site 1.55 kbp downstream of the 3' end of BamHI-$P_1$ (FIGS. 1A and 1B). Fukuchi et al. (Fukuchi, K., et al., J. Virol. 51:102–109 (1984)) have previously mapped the $IR_S$-$U_S$ junction to a 1.4 kb Bgl I fragment located in the second of five EcoRl subfragments of BamHI-A (FIG. 1B). Thus, the sequence presented here should lack between 2.6 and 4.0 kb of the 5'-proximal $U_S$ region, assuming the above $IR_S$-$U_S$ junction location can be independently confirmed. Because the region sequenced does not extend a sufficient distance downstream of BamHI-$P_1$, the MDV $U_S$-$TR_S$ junction has not yet been precisely defined (Davison, A. J., et al., J. Gen. Virol. 76:1759–1816 (1986)). For VZV, EHV-4 and HSV-1, this border is located about 100 bp upstream, or 1.1 and 2.7 kb downstream, respectively, of the termination codon of their respective US8 homologs (Cullinane, A. A., et al., J. Gen. Virol. 69:1575–1590 (1988); Davison, A. J., et al., J. Gen. Virol. 76:1759–1816 (1986); and McGeoch, D. J., et al., J. Gen. Virol. 69:1531–1574 (1988)).

The overall G+C content of the region sequenced was found to be 41%, somewhat below the genomic MDV G+C values of 46% (Lee, L. F., et al., J. Virol. 7:289 (1971)). Observed frequencies of CpG dinucleotides in the whole sequence, or in the coding regions only, did not differ significantly from those expected from their mononucleotide compositions (data not shown). This result agrees with those obtained from alphaherpesviruses, while contrasting with those obtained from gammaherpesviruses, such as the A+T rich HVS and the G+C rich EBV, which are both deficient in CpG dinucleotides (Honess, R. W., et al., J. Gen. Virol. 70:837–855 (1989)).

Figure 1C:
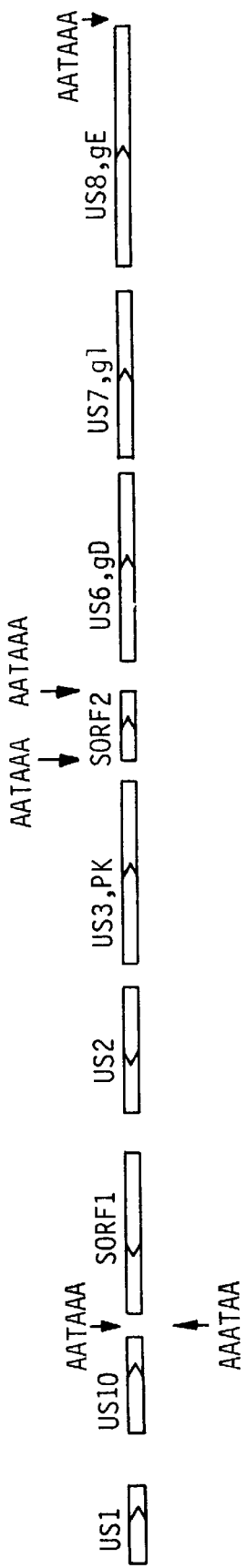

The region sequenced contains 9 complete ORFs likely to code for proteins (FIG. 1C, basis for names is given below). This prediction was based on: (1) homology and positional organization comparisons to other alphaherpesvirus genes and (2) presence of potential TATA and polyadenylation consensus sequences (Birnstiel, M. L., et al., Cell 41:349–359 (1985); and Corden, B., et al., Science 209:1406–1414 (1980)), and (3) possession of favorable contexts for translational initiation (Kozak, M., J. Cell Biool. 108:229–241 (1989)). This identification was further guided by the observation that alphaherpesviruses such as HSV and VZV tend to contain relatively tightly packed, unspliced and generally nonoverlapping coding regions (Davison, A. J., et al., J. Gen. Virol. 76:1759–1816 (1986); Davison, A. J., et al., J. Gen. Virol. 76:1759–1816 (1986); McGeoch, D. J., et al., J. Gen. Virol. 69:1531–1574 (1988); McGeoch, D. J., et al., J. Mol. Biol. 181:1–13 (1985); and McGeoch, D. J., et al., J. Gen. Virol. 68:19–38 (1987)). Such genes, especially those of the $U_S$ regions, often share polyadenylation signals, thereby resulting in 3'-coterminal mRNA families (Rixon, F. J., et al., Nucl. Acids Res. 13:953–973 (1985)). Methods for detecting protein coding regions based on the use of MDV-derived codon frequency tables (using these and previously published MDV sequences, Binns, M. M., et al., Virus Res. 12:371–382 (1989); Ross, L. J. N., et al., J. Gen. Virol. 70:1789–1804 (1989); and Scott, S. D., et al., J. Gen. Virol. 70:3055–3065 (1989)) or analysis of compositional bias (using the GCG programs CODONPREFERENCE and TESTCODE) were largely inconclusive, suggesting that MDV possesses relatively low codon and compositional biases compared to those prediced based on its mononucleotide composition. However, using the GCG program FRAMES, together with the MDV-derived codon frequency table above, the 9 identified ORFs clearly show a significantly low pattern of rare codon usage, which sharply contrasts with that observed in all other potentially translatable regions (data not shown).

The predicted amino acid sequences of the predicted ORFs (beginning from the first ATG codon) are shown relative to the nucleotide sequence in FIGS. 2A to 2H. Potential TATA sites within 400 nucleotides of the initiation codon are underlined. Proposed ORF and potential polyadenylation signal locations, identification of the −3, +4 ATG context nucleotides (Kozak, M., J. Cell Biol. 108:229–241 (1989)), as well as the lengths, relative molecular masses and predicted isoelectric points of the predicted translational products are shown in Table 1.

A summary of MDV data is shown in Table 1, with location of ORFs, predicted polyadenylation signals utilized, translational context nucleotides, lengths, relative molecular sizes and isoelectric points of predicted translation products.

TABLE 1

| Name | ORF Start | ORF End | Predicted Polyadenylation Site | −3, +4 ATG[a] Context Nucleotides | Length (aa) | Predicted[b] Molecular Size (kDa) | Predicted pIc |
|---|---|---|---|---|---|---|---|
| US1 | 248 | 784 | 1777 | A,A | 179 | 20.4 | 6.5 |
| US10 | 1077 | 1715 | 1777 | G,G | 213 | 23.6 | 8.2 |
| SORF1 | 2884 | 1832 | 1790 | A,A | 351 | 40.6 | 8.2 |
| US2 | 3923 | 3114 | 1790 | A,G | 270 | 29.7 | 7.6 |
| US3 | 4062 | 5240 | 5394 | A,G | 393 | 43.8 | 6.1 |
| SORF2 | 5353 | 5793 | 5904 | C,G | 147 | 16.7 | 9.8 |
| US6 | 5964 | 7172 | 10040 | G,G | 403 | 42.6[d] | 10.3[d] |
| US7 | 7282 | 8346 | 10040 | G,T | 355 | 38.3[d] | 6.7[d] |
| US8 | 8488 | 9978 | 10040 | A,T | 497 | 53.7[d] | 8.0[d] |

[a]Nucleotides listed relative to −3, +4 positions, respectively; numbering begins with the A of the ATG (AUG) codon as position +1; nucleotides 5' to that site are assigned negative numbers.
[b]In absence of post-translational modifications.
[c]Calculated using the GCG program, ISOELECTRIC.
[d]Based on sequences that follow the predicted signal peptide cleavage site.

In the absence of previous information concerning these MDV ORFs, and to simplify identification, they have been named (FIG. 1C, Table 1) based on homologous relationships to HSV-1 encoded $U_S$ ORFs (McGeoch, D. J., et al., J. Mol. Biol. 181-1–13 (1985)). When appropriate, the letters MDV will preface the homolog's name to indicate the ORF's origin. The two MDV-specific ORFs have been arbitrarily named SORF1 and SORF2, based on their location in the S component.

According to the scanning model for translation, the 40S ribosomal subunit binds initially at the 5'-end of MRNA and then migrates, stopping at the first AUG (ATG) codon in a favorable context for initiating translation (Kozak, M., J. Cell Biol. 108:229–241 (1989)). However, in the absence of S1 nuclease and/or primer extension analysis, definitive start sites for translation cannot be accurately predicted. Nevertheless, likely start sites are listed in Table 1; these refer to the location of the first inframe ATG codon found in the major open reading frame. According to Kozak (Kozak, M., J. Cell Biol. 108:229–241 (1989)), as long as there is a purine in position −3, deviations from the rest of the consensus only marginally impair initiation. In the absence of such a purine, however, a guanine at position +4 is essential for efficient translation. Table 1 shows that all of the ORFs, except for SORF2, contain the important purine residue in the −3 position. Nevertheless, in the case of SORF2, a compensating guanine in position +4 is indeed present.

In the case of MDV US1, two transcriptional cap sites have been tentatively identified by 5′ S1 nuclease protection analysis (data not shown). These sites appear to be located 18 and 25 nucleotides downstream of a TATATAA sequence at position 200 and 207, respectively (FIGS. 2A to 2H) Based on 3′ S1 data, this transcript utilizes a polyadenylation signal located just downstream of the US10 coding region (Table 1, data not shown). Comparative Northern blot analyses of the $U_S$ region indicate that the MDV US1 transcript appears to be the most prominent transcript expressed at late times (72 h) post-infection when extensive cytopathic effects are observed (data not shown). Phosphonoacetic acid inhibition studies have indicated that MDV US1, in contrast to its immediate-early HSV1 US1 counterpart, is regulated as a late class gene (data not shown).

Using the computer program FASTA (Pearson, W. R., et al., Proc. Natl. Acad. Sci. USA 85:2444–2448 (1988)) with a K-tuple value of 1, each of the 9 predicted amino acid sequences was screened against the NBRF-Protein database (Release 21.0, 6/89), and recently published EHV-4 S segment gene sequences (11). Optimized FASTA scores of greater than 100 were generally considered to indicate a significant degree of amino acid similarity. The results of this analysis are in Table 2.

TABLE 2

PAIRWISE COMPARISONS OF MDV AND ALPHAHERPESVIRUS S COMPONENT HOMOLOGS

|  |  | US1 | | | | | US10 | |
| --- | --- | --- | --- | --- | --- | --- | --- | --- |
|  | Virus | MDV | HSV-1 | VZV | PRV | EHV-4 | MDV | HSV-1 |
| % similar / % identical | MDV | — | 47/26 | 43/27 | 51/33 | 48/30 | — | 45/24 |
|  | HSV-1 | 47/26 | — | 49/29 | 43/25 | 50/29 | 45/24 | — |
|  | VZV | 43/27 | 49/29 | — | 51/35 | 54/36 | 40/24 | 49/27 |
|  | PRV | 51/33 | 43/25 | 51/35 | — | 56/41 | a | a |
|  | EHV-4 | 48/30 | 50/29 | 54/36 | 56/41 | — | 45/29 | 49/27 |
| FASTA scores | MDV | 891 | 101 | 160 | 218 | 208 | 1,071 | 134 |
|  | HSV-1 | 101 | 2,047 | 119 | 201 | 150 | 134 | 1,617 |
|  | VZV | 160 | 119 | 1,378 | 340 | 359 | 147 | 123 |
|  | PRV | 218 | 201 | 340 | 1,724 | 525 | a | a |
|  | EHV-4 | 208 | 150 | 359 | 525 | 1,308 | 251 | 180 |
|  | length (aa) | 179 | 420 | 278 | 364 | *273 | 213 | 312 |

|  |  | US10 | | US2 | | | US3 | | | |
| --- | --- | --- | --- | --- | --- | --- | --- | --- | --- | --- |
|  | Virus | VZV | EHV-4 | MDV | HSV-1 | PRV | MDV | HSV-1 | VZV | PRV |
| % similar / % identical | MDV | 40/24 | 45/29 | — | 51/33 | 48/26 | — | 56/38 | 54/33 | 55/33 |
|  | HSV-1 | 49/27 | 49/27 | 51/33 | — | 50/31 | 56/38 | — | 57/41 | 59/36 |
|  | VZV | — | 55/32 | a | a | a | 54/33 | 57/41 | — | 58/35 |
|  | PRV | a | a | 48/26 | 50/31 | — | 55/33 | 59/36 | 58/35 | — |
|  | ENV-4 | 55/32 | — | a | a | a | a | a | a | a |
| FASTA scores | MDV | 147 | 251 | 1,421 | 355 | **118 | 1,931 | 611 | 616 | 563 |
|  | HSV-1 | 123 | 180 | 335 | 1,554 | 112 | 611 | 2,409 | 717 | 620 |
|  | VZV | 978 | 191 | a | a | a | 616 | 717 | 1,960 | 595 |
|  | PRV | a | a | **168 | 112 | 1,240 | 563 | 620 | 595 | 1,948 |
|  | EHV-4 | 191 | 1,312 | a | a | a | a | a | a | a |
|  | length (aa) | 180 | 259 | 270 | 291 | 256 | 393 | 481 | 393 | 390 |

|  |  | US6 | | | | | US7 | | |
| --- | --- | --- | --- | --- | --- | --- | --- | --- | --- |
|  | Virus | MDV | HSV-1 | PRV | EHV-1 | BHV-1 | MDV | HSV-1 | VZV |
| % similar / % identical | MDV | — | 42/21 | 44/23 | 43/21 | 42/33 | — | 39/22 | 46/23 |
|  | HSV-1 | 42/21 | — | 47/27 | 44/22 | 50/28 | 39/22 | — | 43/24 |
|  | VZV | b | b | b | b | b | 46/23 | 43/24 | — |
|  | PRV | 44/23 | 47/27 | — | 51/30 | 57/38 | 43/25 | 41/26 | 47/25 |
|  | EHV-1 | 43/21 | 44/22 | 51/30 | — | 52/30 | 41/23 | 42/23 | 46/29 |
|  | BHV-1 | 42/33 | 50/28 | 57/38 | 52/30 | — | a | a | a |
| FASTA scores | MDV | 2,068 | 211 | 279 | 246 | 291 | 1,816 | 145 | 228 |
|  | HSV-1 | 211 | 1,999 | 294 | 253 | 304 | 145 | 1,880 | 234 |
|  | VZV | b | b | b | b | b | 228 | 234 | 1,705 |
|  | PRV | 279 | 294 | 2,116 | 428 | 730 | 188 | 188 | 198 |
|  | EHV-1 | 246 | 253 | 428 | 1,995 | 494 | 242 | 249 | 298 |
|  | BHV-1 | 291 | 304 | 730 | 494 | 2,148 | a | a | a |
|  | length (aa) | 403 | 394 | 402 | 395 | 417 | 355 | 390 | 354 |

TABLE 2-continued

PAIRWISE COMPARISONS OF MDV AND ALPHAHERPESVIRUS S COMPONENT HOMOLOGS

|  | | US7 | | US8 | | | | |
| --- | --- | --- | --- | --- | --- | --- | --- | --- |
|  | Virus | PRV | EHV-1 | MDV | HSV-1 | VZV | PRV | EHV-1 |
| % similar | MDV | 43/25 | 41/23 | — | 44/22 | 43/22 | 46/28 | 47/22 |
| ——— | HSV-1 | 41/26 | 42/23 | 44/22 | — | 46/27 | 49/28 | 41/23 |
| % identical | VZV | 47/25 | 46/29 | 43/22 | 46/27 | — | 47/25 | 46/29 |
|  | PRV | — | 51/30 | 46/28 | 49/28 | 49/29 | — | 54/34 |
|  | EHV-1 | 51/30 | — | 47/22 | 41/23 | 50/28 | 54/34 | — |
|  | BHV-1 | a | a | a | a | a | a | a |
| FASTA scores | MDV | 184 | 242 | 2,489 | 192 | 376 | **243 | 399 |
|  | HSV-1 | 188 | 249 | 192 | 2,751 | 357 | 257 | 274 |
|  | VZV | 184 | 242 | 376 | 357 | 3,171 | 329 | 468 |
|  | PRV | 188 | 249 | **217 | 257 | 329 | 2,923 | 417 |
|  | EHV-1 | 274 | 1,979 < | 399 | 274 | 468 | 417 | 2,821 |
|  | BHV-1 | a | a | a | a | a | a | a |
|  | length (aa) | 350 | 424 | 497 | 550 | 623 | 577 | 552 |

[a]existence of homolog undetermined
[b]no homolog present in genome
*actual length will differ somewhat, since probable initiation codon not defined
**different score when order of comparison reversed While SORF1 and SORF2 do not appear to share any significant homology to any of the sequences in the database (data not shown), apart from MDV US3, the other six ORFs (MDV US1, 10, 2, 6, 7, and 8; Tables 1, 2) were found to be homologous to alphaherpesvirus S segment genes exclusively (Table 2). Because the US3 ORF represents a member of the serine-threonine protein kinase superfamily (Hanks, S. K., et al., Science 241:42- (1988)), a relatively large number of scores above 150 were obtained. Nevertheless, these scores were 3–4 fold lower than those obtained in comparisons with US3 homologs of HSV, PRV and VZV. To compare with previously established alphaherpesvirus S segment homologies, all possible FASTA comparisons between the seven groups of alphaherpesvirus-related sequences are included. The program GAP was used in similar pairwise comparisons to generate optimal alignments in order to determine the total percentage of identical and similar amino acids shared by the two sequences. As shown in Table 2, homology comparisons between MDV S segment ORFs and their alphaherpesvirus counterparts were comparable to those previously observed between the other alphaherpesvirus S segment homologs themselves. In some cases MDV ORFs were found to be more related to alphaherpesvirus homologs than those same homologs were to their other alphaherpesvirus counterparts (compare MDV/EHV-4 vs. HSV-1/EHV-4 US1 and MDV/EHV-4 vs. HSV-1/EHV-4 US10 homologies). Moreover, despite the fact that VZV lacks US2 and US6 homologs, MDV, although formally considered a gammaherpesvirus, clearly does possess US2 and US6 homologs. The results of limited multiple alignments for each of the seven homologs in which areas showing best conservation are depicted in FIGS. 3A-1 to 3A-2.

Figures 1, 3B:
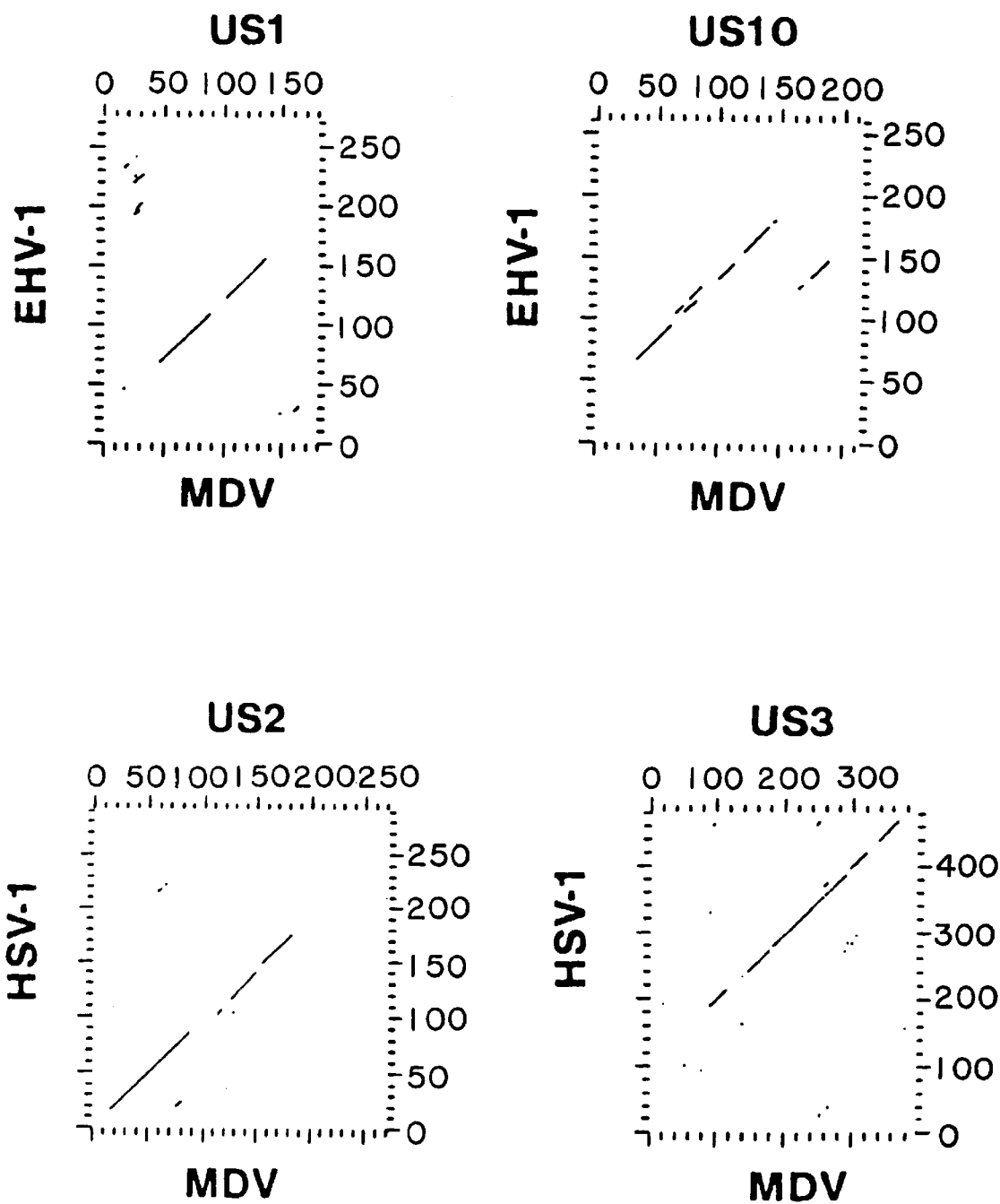

Dot matrix homology plots depicting overall homologies between selected MDV-alphaherpesvirus S segment homolog comparisons are included in FIGS. 3B-1 to 3B-2. (Using a sliding window length of 30 amino acids, in which points are generated where at least 15 amino acids are found identical or similar). The resulting diagonals illustrate the regions showing greatest conservation. Such regions include and in some cases extend upon those regions depicted in FIGS. 3A-1 to 3A-2.

More sensitive attempts to identify other related proteins not detected with FASTA were made using the GCG programs PROFILE and PROFILESEARCH. Use of these programs permit database comparisons which rely on information available from structural studies and, in this case, from information implicit in the alignments of related S component ORFs (including MDV sequences using GAP) (Gribskov, M., et al., Proc. Natl. Acad. Sci. USA 84:4355–4358 (1987)); nevertheless, such analyses failed to extend upon the groups of related proteins described here.

Herpesvirus glycoprotein homologs have generally been found to contain similar patterns of conserved cysteine residues. In comparing the gB homologs of seven different herpesviruses included in the alpha-, beta- and gammaherpesvirus subclasses, there is complete conservation of 10 cysteine residues (Ross, L. J. N., et al., J. Gen. Virol. 70:1789–1804 (1989)). HSV-1 US6 (gD) contains 7 cysteine residues: six appear critical for correct folding, antigenic structure and extent of oligosaccharide processing (Wilcox, W. C., et al., J. Virol. 62:1941–1947 (1988)). Not only is this same general pattern of cysteines conserved in the gD homologs of HSV-2 (McGeoch, D. J., et al., J. Gen. Virol. 68:19–38 (1987)) and PRV (Petrovskis, E. A., et al., J. Virol. 59:216–223 (1986)), but they are conserved in the MDV gD homolog as well (full alignment not shown). FIGS. 3A-1 to 3A-2 depict portions of cysteine conservation patterns observed among the US6 (gD), US7 (gI), and US8 (gE) homologs (in which case 4, 3, and 6 conserved cysteine residues are shown, respectively). While the MDV, VZV, PREV, and EHV-1 US8 homologs (Audonnet, J.-C., et al., J. Gen. Virol. 71:2969–2978 (1990); Davison, A. J., et al., J. Gen. Virol. 76:1759–1816 (1986); and Petrovskis, E. A., et al., J. Virol. 60:185–193 (1986)) all share a similar pattern of four conserved cysteine residues near their amino termini, the HSV-1 and -2 counterparts carry only two of these (McGeoch, D. J., J. Gen. Virol. 71:2361–2367 (1990); data not shown). It is quite possible that the unique pattern of four conserved cysteines could facilitate the formation of different secondary and tertiary structures which might impart important functional consequences. These might be reflected by findings which show that HSV-1 gE has Fc receptor activity (Johnson, D. C., et al., J. Virol. 62:1347–1354 (1988)), while its PRV and VZV counterparts do not (Edson, C. M., et al., Virology, 161:599–602 (1987); and Zuckerman, F. A., et al., J. Virol. 62:4622–4626 (1988)).

Careful inspection of the N-terminal regions of the MDV gD, gI and gE homologs has revealed that they contain the three basic building blocks of signal peptide sequences: a basic, positively charged N-terminal region (n-region), a central hydrophobic region (h-region), and a more polar terminal region (c-region) that seems to define the cleavage site (von Heijne, G. J. Mol. Biol. 184:99–105 (1985)). Using a recently improved method for predicting signal sequence cleavage sites (von Heijne, G. Nucl. Acids Res. 14: 4683–4690 (1986)), Table 3 shows the likely position of these sites, the location of the hydrophobic transmembrane and charged cytoplasmic domains near the C-terminal end and the location of potential N-glycosylation sites.

Table 3 shows MDV $U_S$ glycoprotein data on predicted signal peptide cleavage sites and locations of transmembrane and cytoplasmic domains and potential N-glycosylation sites (with respect to the ATG initiation codon).

TABLE 3

| Name | Predicted Signal Peptide Cleavage Site | Trans-membrane Domain | Cyto-plasmic Domain | N-glycosylation Sites |
|---|---|---|---|---|
| US6 | $G_{30}$–$D_{31}$ | 358–374 | 375–403 | 87,138,230,306 |
| US7 | $S_{18}$–$I_{19}$ | 269–288 | 289–355 | 147,167,210,245, 253 |
| US8 | $T_{18}$–$A_{19}$ | 394–419 | 420–497 | 60,133,148,203, 229,277,366,388 |

Like the other gI homologs, MDV's counterpart contains a relatively long cytoplasmic domain. However, in contrast to the other gD homologs, MDV gD's signal peptide contains a relatively long n-region (18 residues), that is unusually highly charged (+4; FIGS. 2A to 2H) considering an overall mean value of +1.7 among eukaryotes, which generally does not vary with length (von Heijne, G, J. Mol. Biol. 184:99–105 (1985)). Although a more distal methionine codon exists directly before the initiation codon (as in the PRV gD homolog, Petrovskis, E. A., et al., J. Virol. 59:216–223 (1986)) the scanning model for translation (Gribskov, M., et al., Proc. Natl. Acad. Sci. USA 84:4355–4358 (1987)) favors usage of the more 5'-proximal initiation codon (at position 5964, FIGS. 2A to 2H). Further support is based on an overall translation context that appears at least as good as, if not better than, the one corresponding to the downstream ATG. Despite such a prediction, a possible mRNA cap site location between the two ATG sites, which would preclude such a prediction, cannot be ruled out at this point.

One final point concerning MDV gD requires mention. Using the 10,350 nucleotide DNA sequence as a probe for screening the GenBank (62.0, 12/89) and EMBL (19.0, 5/89) nucleic acid databases with the computer program FASTA (K-tuple=6), an optimized score of 1027, corresponding to 91.5% nucleotide identity in a 342 bp overlap between MDV gD coding sequences (6479–6814; aa#173–aa#284; FIGS. 2A to 2H) and a previously reported 467 bp MDV DNA segment (Wen, L.-T., et al., J. Virol. 62:3764–3771 (1988)). The latter sequence has been reported to contain a 60 bp segment protected against DNAse digestion by binding of a 28 kD MDV nuclear antigen (MDNA) expressed only in "latently" infected MDV-transformed lymphoblastoid cells. In view of similarities between MDV and VZV, these authors suggested that MDNA may function in a manner analogous to that of EBNA-1 in immortalizing primate cells. In their report, Wen et al. (Wen, L.-T., et al., J. Virol. 62:3764–3771 (1988)) mapped the MDNA binding site to the same EcoRI subfragment of BamHI-A in which MDV gD is located (EcoRI-I, FIG. 1). Although our sequence covering this region is consistent with a complete, uninterrupted ORF containing all the characteristic features of a glycoprotein, and showing significant homology to HSV gD, their sequence contains about 140 bases of 5'-proximal sequence unrelated to any determined from our 5.3 kbp EcoRl-I fragment or its adjoining 3.5 kb sequences. The remaining 327 bp sequence (which contains the putative nuclear antigen binding site) while clearly resembling our gD coding sequence, upon computer translation fails to yield any ORF longer than 30 aa.

Discussion

Recent data have shown that despite MDV's classification as a gammaherpesvirus, based on lymphotropic properties shared with other members of this subfamily, its genome structure (Cebrian, J., et al., Proc. Natl. Acad. Sci. USA 79:555–558 (1982); and Fukuchi, K., et al., J. Virol. 51:102–109 (1984)) and genetic organization of primarily its $U_L$ region (Buckmaster, A. E., et al., J. Gen. Virol. 69:2033–2042 (1988)) more closely resembles that of the neurotropic alphaherpesviruses. Moreover, in cases where polypeptide sequences were found conserved among the three herpesvirus subfamilies (e.g. $U_L$ genes), significantly higher homology scores were consistently observed against the respective alpha- rather than beta- or gammaherpesvirus counterparts (Davison, A. J., et al., J. Gen. Virol. 67:597–611 (1986); Buckmaster, A. E., et al., J. Gen. Virol. 69:2033–2042 (1988); Ross, L. J. N., et al., J. Gen. Virol. 70:1789–1804 (1989); and Scott, S. D., et al., J. Gen. Virol. 70:3055–3065 (1989)). Alphaherpesvirus S segment genes have previously been found to be unique to members of this taxonomic subfamily (Davison, A. J., et al., J. Gen. Virol. 68:1067–1079 (1987); and Davison, A. J., et al., J. Gen. Virol. 67:597–611 (1986)). The identification of seven MDV homologs of alphaherpesvirus S segment genes in this study is consistent with the idea that MDV shares a closer evolutionary relationship with alphaherpesviruses than gammaherpesviruses. This is further supported by dinucleotide frequency analysis which fails to show a lack of CpG suppression as observed among all gammaherpesviruses thus far studied (Efstathiou, S., et al., J. Gen. Virol. 71:1365–1372 (1990); and Honess, R. W., et al., J. Gen. Virol. 70:837–855 (1989)). The above situation resembles a similar one observed with human herpesvirus-6 (HHV-6), in which case its T-lymphotropism suggested provisional classification as a gammaherpesvirus (Lopez, C., et al., J. Infect. Dis. 157:1271–1273 (1988)). However, subsequent genetic analysis has shown a greater relatedness between HHV-6 and the betaherpesvirus, human cytomegalovirus (HCMV; Lawrence, G. L., et al., J. Virol. 64:287–299 (1990)).

A comparison of the genetic organization of alphaherpesvirus S segment genes is presented in FIG. 4. The organization of these genes in some cases vary greatly in overall length, organization and degree of homology. Nevertheless, the overall gene layouts displayed are consistent with a model to account for the divergence of alphaherpesviruses from a common ancestor by a number of homologous recombination events which result in expansion or contraction of the inverted repeat regions and a concomitant loss or gain of $U_S$ gene(s). In the case of VZV, six S segment homologs are lacking compared to HSV-1 (US2, US4, US5, US6, US11, US12). Some genes, such as the US1 homologs, show particular sequence and length divergences. Compared to HSV-1, the MDV, VZV and EHV-4 US1 homologs lack approximately 120 aa of sequence comparable to the 5'-proximal portion of HSV-1 US1 (alpha 22) Based on Northern blot analysis, S1 nuclease protection analysis and phosphonoacetic acid inhibition studies, in contrast to its relatively uncharacterized immediate-early HSV-1 counterpart, the MDV US1 gene appears to be regulated as an abundantly expressed late class gene (data not shown). In contrast to the other alphaherpesviruses, MDV contains two apparently MDV-specific ORFs. Moreover, the MDV $U_S$ region appears to contain approximately 2.6 to 4.0 kb of additional 5'-proximal sequences. Based on a comparison of FIG. 4 and consideration of the expansion-contraction recombination scheme, it appears likely that there are additional MDV-specific $U_S$ genes.

Since MDV has long been regarded as a gammaherpesvirus, much of the previous work interpreting their properties has proceeded by analogy with the association between EBV and B cells (Nonoyama, M. p. 333–341. In B. Roizman (ed.), The herpesviruses, vol. 1. Plenum Press (1982); and Wilbur, W. J., et al., Proc. Natl. Acad. Sci. USA 80:726–730 (1983)). Because of a closer genetic relationship to the alphaherpesviruses, and keeping in mind the analysis of HHV-6 above, we agree with Lawrence et al. (Lawrence, G. L., et al., J. Virol. 64:287–299 (1990)) that the lymphotropic properties of MDV and HVT are unlikely to be determined by molecules homologous to EBV and that a delineation of molecular differences between MDV and the neurotropic alphaherpesviruses would be more fruitful in explaining the observed biological differences than employing analogies based on properties of gammaherpesviruses such as EBV and HVS.

To account for such differences, the MDV $U_S$ region may be particularly important. With few exceptions, each HSV-1 L component gene possesses an equivalent in VZV (McGeoch, D. J., et al., J. Gen. Virol. 69:1531–1574 (1988)); a considerable number of these are related to beta- and gammaherpesvirus genes as well (29 of 67 EBV counterparts to VZV $U_L$ genes; Davison, A. J., et al., J. Gen. Virol. 68:1067–1079 (1987)). In contrast, the S segments of HSV-1 and VZV differ significantly in size and appear to be among the least related parts of the two genomes (Davison, A. J., et al., J. Gen. Virol. 67:597–611 (1986; and Davison, A. J., et al., J. Gen. Virol. 64:1927–1942 (1983)). Recent studies have shown that 11 of 12 open reading frames contained in the HSV-1 S component are dispensable for growth in cell culture (Longnecker, R., et al., Proc. Natl. Acad. Sci. USA 84:4303–4307 (1987); and Weber, P. C., et al., Science 236:576–579 (1987)). The maintenance and evolution of such a dispensable gene cluster suggests the presence of functions relevant to the viruses survival in its specific ecological niche in the natural or laboratory animal host, rather than the presence of functions necessary for replication (Longnecker, R., et al., Proc. Natl. Acad. Sci. USA 84:4303–4307 (1987); and Weber, P. C., et al., Science 236:576–579 (1987)). Consistent with such a hypothesis are findings that HSV mutants carrying different S component gene-specific deletions were significantly less pathogenic and exhibited a reduced capacity for latency establishment in mice (Meignier, B., et al., Virology 162:251–254 (1988)). In regard to the latter, there is evidence suggesting that RNA transcribed from the HSV $U_S$ region may be involved in the establishment and maintenance of an in vitro latency system employing human fetus lung fibroblast cells (Scheck, A. C., et al., Intervirology 30:121–136 (1989)). Taken together, the above evidence suggest(s) potentially important role(s) for MDV's $U_S$ genes in tissue tropism, latency, and/or induction of cell transformation.

A consideration of the three gD, gI and gE homologs identified in this invention raises two other questions of relevance to future vaccine development. The 11 HSV-1 $U_S$ region genes dispensible for growth in tissue culture described above include HSV-1 US7 (gI) and US8 (gE) (Longnecker, R., et al., Proc. Natl. Acad. Sci. USA 84:4303–4307 (1987); and Weber, P. C., et al., Science 236:576–579 (1987)). Assuming the MDV homologs have the same properties, these genes may be useful as sites for insertion of foreign genes. Further the same two MDV homologs, and especially US8 (gE), may very likely be involved in the pathogenicity-related issues introduced above. Specifically HSV's gE seem to play a role in HSV-1's ability to establish lethal infections and latency in mice (Meignier, B., et al., Virology 162:251–254 (1988)). Further, the gI and gE homologs of PRV of swine play a clear role in PRV virulence for 1-day-old chickens and young pigs (Mettenleiter, Thomas C., et al., Journal of Virology, p. 4030–4032 (December 1987)). Assuming the same holds true for the MDV US7 (gI) and US8 (gE) homologs, it may be possible to inactivate one or both of these genes from very virulent MDV isolates which cause outbreaks not prevented by current vaccines, and thereby creating an attenuated vaccine viruses more closely related to field virus causing disease outbreaks.

A further consideration of the three (gD, gI and gE) homologs identified in this invention raises another interesting question. Fully enveloped infectious MDV virions are only known to be produced in feather follicle epithelial cells (Payne, L. N. p. 347–431. In B. Roizman (ed.), The herpesviruses, vol. 1. Plenum Press (1982)). Because of this, MDV studies have had to rely on limited fibroblast cell cultures which only promote the spread of cell-associated infections in vitro. Over the last 20 years, studies aimed at identifying immunogenic surface antigens have relied on this in vitro culture system and altogether only two glycoprotein antigens (A antigen/gC homolog; B antigen) have been routinely identified and characterized (Binns, M. M., et al., Virus Res. 12:371–382 (1989); Coussens, P. M., et al., J. Virol. 62:2373–2379 (1988); Isfort, R. J., et al., J. Virol. 59:411–419 (1986); Isfort, R. J., et al., J. Virol. 57:464–474 (1986); and Sithole, I., et al., J. Virol. 62:4270–4279 (1988)). This is despite findings of three MDV gD, gI and gE homologs of the present invention and two additional glycoprotein homologs (gB and gH, Buckmaster, A. E., et al., J. Gen. Virol. 69:2033–2042 (1988); and Ross, L. J. N., et al., J. Gen. Virol. 70:1789–1804 (1989)). While immune chicken sera (ICS) from naturally infected birds is likely to react with many, if not all, MDV-encoded surface antigens, this complex polyclonal sera would only be useful to the extent that antigen expression/processing in semi-productive cell culture resembles that in feather follicle epithelial cells. Northern blot analysis using MDV gD-specific probes suggests that MDV gD mRNA is either not expressed or poorly expressed in DEF cells at a time when extensive cytopathic effects are observed (data not shown). In light of the fact that VZV lacks a gD homolog and is strongly cell-associated, it will be interesting to see whether the block in MDV virion formation in primary avian fibroblast cells is found to correlate with lack of expression (in these cells) of a glycoprotein, such as gD, and/or some other S component gene(s).

Because the protection against MD conferred by attenuated MDV strains (serotype 2) or HVT (serotype 3) appears to have an immunological basis, there is considerable interest in identifying common antigens. In view of this invention identifying seven MDV $U_S$ homologs to $U_S$ genes of HSV (the latter of which is clearly less related to MDV than HVT is), it would be surprising if the previous report showing lack of homology between MDV-HVT $U_S$ regions (Igarashi, T., et al., Virology 157:351–358 (1987)) were proven correct. Such negative results may reflect the limitations regarding homology estimates based on hybridization, rather than sequence analysis studies.

Example 2 shows the molecular cloning of a construct containing the DNA encoding the complete MDV US7 (gI) gene and part of the MDV US8 (gE) gene. As can be seen, this is accomplished using segments of DNA spanning the gI and part of the gE coding region.

EXAMPLE 2

MOLECULAR CLONING OF A CONSTRUCT CONTAINING THE DNA ENCODING THE COMPLETE MDV US7 (gI) and PART OF MDV US8 (gE)

Construction of a recombinant clone (pKS-MDgI1.59) containing the complete MDV US7 (gI) coding sequence and a portion of the MDV US8 (gE) coding sequence requires two preexisting MDV clones, pKS-MDgD1.75 and p19P1 (FIG. 5). pKS-MDgD1.75 is a recombinant plasmid containing the 1.75 kbp NcoI-SstII subfragment of MDV EcoRl-I ligated into the SmaI-Sst II site of the cloning vector, pBluescript KS-. This clone contains the complete MDV US6 (gD) coding sequence and additional sequences at the 3' end which code for the first 39 amino acids (aa) of MDV gI. p19P1 is a recombinant plasmid containing the 1.5 kbp BamHI-$P_1$ subfragment of MDV cloned into the unique BamHI site of pUC19. This clone contains the entire MDV gI coding sequence, except for the first 9 aa of its signal sequence. In addition, at the 3' end, p19P1 contains the first 104 aa of the MDV US8 (gE) coding region.

To generate pKS-MDgI1.59, pKS-MgD1.75 is first cut with HincII, which cuts once in the multiple cloning site of the pBluescript vector and once about 180 bp upstream of the insert's SstII terminus. This results in two fragments: one fragment (1.6 kbp) consists primarily of insert sequences encoding MDV US6 (gD); the larger fragment (3.1 kbp) consists of pBluescript vector sequences, in addition to about 180 bp which encode the N-terminus of MDV gI. The 3.1 kb fragment is gel purified and self-ligated by way of the two HincII ends. The resulting recombinant plasmid, pKS-MDgI0.18, is then cut with SstI (in the multiple cloning site, just downstream of the SstII site). Prior to subsequent digestion with SstII, the cohesive SstI ends is made blunt-ended with T4 DNA polymerase. The resulting 3.1 kbp SstII-SstI (blunt) fragment of pMDgI0.18 is gel purified and used in the final ligation step to create pKS-MDgI1.59. While the enzymatic manipulations of pKS-MDgD1.75 and pKS-MDgI0.18 are taking place, p19P1 is cut with HindIII, which cuts just downstream of the partial MDV US8 (gE) coding sequence in the multiple cloning site of pUC19. Prior to digestion with SstIId, the cohesive HindIII ends is made blunt-ended using Klenow fragment. The smaller SstII-HindIII (blunt) fragment (1.4 kbp) contains a majority of the MDV US7 (gI) coding sequence, in addition to 312 nucleotides at the 3' end which code for the 5' end of MDV gE. This 1.4 kbp SstII-HindIII(blunt) fragment is gel purified and ligated to the 3.1 kbp SstII-SstI(blunt) fragment of pKS-MDgD0.18. The resulting recombinant, pKS-MDgI1.59, contains the complete coding sequence for MDV gI and a portion of the N-terminal gE coding sequence. Digestion of pKS-MDgI1.59 with KpnI yields two fragments; the smaller 1.15 kbp fragment contains the complete coding sequence for MDV gI.

Example 3 shows molecular subcloning of a construct containing the complete MDV US8 (gE) gene.

EXAMPLE 3

MOLECULAR CLONING OF A CONSTRUCT ENCODING THE COMPLETE MDV US8 (gE)

Construction of a recombinant clone (p18-MDgE2.53) containing the complete MDV US8 (gE) coding sequence requires a clone other than the BamHI or EcoRl clones used previously. GA strain clone GA-02, an EMBL-3 clone containing a partially digested MDV SalI insert, which contains BamHI-A, -P1, and additional 5' and 3' flanking sequences (kindly provided by P. Sondermeier, Intervet Intl. B. V., Boxmeer, The Netherlands) was used to extend analysis 3' of the EcoRl-I and BamHl-P1 fragments. Smaller SalI subfragments located at the 3' end of this phage clones MDV insert were gel purified and ligated to pUC18 linearized to SalI (pSP18-A, pSP18-B, and pSP18-C, FIG. 1B). The pUC18 subclone, pSP18-A contains the entire MDV US8 (gE) coding sequence and is designated p18-MDgE2.53 for ATCC deposit purposes.

Index of definition of letters in FIGS. 2A to 2H. Table 4 showing the amino acids with both their single letter and three letter symbols.

TABLE 4

| A | Ala | Alanine | M | Met | Methionine |
|---|---|---|---|---|---|
| C | Cys | Cysteine | N | Asn | Asparagine |
| D | Asp | Aspartic Acid | P | Pro | Proline |
| E | Glu | Glutamic Acid | Q | Gln | Glutamine |
| F | Phe | Phenylalanine | R | Arg | Arginine |
| G | Gly | Glycine | S | Ser | Serine |
| H | His | Histidine | T | Thr | Threonine |
| I | Ile | Isoleucine | V | Val | Valine |
| K | Lys | Lysine | W | Trp | Tryptophan |
| L | Leu | Leucine | Y | Tyr | Tyrosine |

When the DNA segments encoding glycoproteins gI and gE are altered by insertional, site-directed or deletion mutagenesis, the pathogenicity of the MDV may be reduced. Also, the segments of DNA encoding the non-essential gI and gE can be used as insertion sites for segments of foreign DNA which encode proteins that are antigenically active for the purpose of producing a recombinant vaccine.

ATCC Deposit

The gene for MDV US6 (MDV gD) has been deposited in a plasmid (phagemid) pKS-MDgD1.75, as ATCC 40855, with The American Type Culture Collection, Rockville, Md., 20852, USA.

The gene for MDV US7 (MDV gI) has been deposited in a plasmid (phagemid) pKS-MDgI1.59, as ATCC 75040, with The American Type Culture Collection, Rockville, Md., 20852, USA.

The gene for MDV US8 (MDV gE) has been deposited in a plasmid p18-MDgE 2.53, as ATCC 75039, with The American Type Culture Collection, Rockville, Md., 20852, USA.

Attached are Sequence Listings for Sequence ID NOS. 1, 2 and 3 as previously described in the application.

We claim:

1. A 2.53 Kb isolated segment of DNA with a gene coding for MDV glycoprotein E (gE) precursor containing 497 amino acids, which extends from nucleotide 8488 to nucleotide 9978 of SEQ ID No:1, and optionally containing sequences 5' of the gene in SEQ ID NO:1.

2. In a method for producing an in vitro expression vector for a protein by providing in the vector a segment of DNA from the genome of a Marek's disease herpesvirus the improvement which comprises:

inserting into the vector a segment of DNA selected from the group consisting of nucleotide 7282 to nucleotide 8345 and nucleotide 8488 to nucleotide 9978 of SEQ ID NO:1 the segment encoding a glycoprotein precursor selected from the group consisting of gI and gE of the Marek's disease herpesvirus, respectively and optionally containing sequences 5' of the segments as shown in SEQ ID NO:1.

* * * * *

UNITED STATES PATENT AND TRADEMARK OFFICE
CERTIFICATE OF CORRECTION

PATENT NO. : 6,087,127
DATED : July 11, 2000
INVENTOR(S) : Leland F. Velicer, Peter Brunovskis and Paul M. Coussens It is certified that error appears in the above-indentified patent and that said Letters Patent is hereby corrected as shown below:

Column 13, Table 2, line 12, "184" should be -198-.
Column 13, Table 2, line 12, "242" should be -298-.
Column 13, Table 2, line 13, "188" should be 1652-.
Column 13, Table 2, line 13, "249" should be -274-.

Signed and Sealed this

Seventeenth Day of April, 2001

Attest:

NICHOLAS P. GODICI

Attesting Officer     Acting Director of the United States Patent and Trademark Office

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
       (A) LENGTH: 10350 base pairs
       (B) TYPE: nucleic acid
       (C) STRANDEDNESS: double
       (D) TOPOLOGY: linear (ii) MOLECULE TYPE: genomic DNA (iii) HYPOTHETICAL: Yes (v) ANTI-SENSE: No (vi) ORIGINAL SOURCE:
       (A) ORGANISM: MDV, GA strain (vii) IMMEDIATE SOURCE:
       (A) LIBRARY: genomic (xi) SEQUENCE DESCRIPTION: SEQ ID NO:1:

```
GAATTCCTTG AAATTGGAGT GAAATCTTTA GGGAGGGAGG TTTACCATTG TGGAGAATAT        60

ATAGAGCAAG TAGTACATTA GGGGCTGGGT TAAAGACCAA GTAATTTTTG ACCGGATATC       120

ACGTGATGTA AATTCTAGCA ATTATTGTTC CTAGCAGAAG ATAAAAGCTG GTAGCTATAT       180

AATACAGGCC AAAGTCTCCA AATTACACTT GAGCAGAAAA CCTGCTTTCG GCTCCATCGG       240

AGGCAAC ATG AGT CGT GAT CGA GAT CGA GCC AGA CCC GAT ACA CGA TTA        289
        Met Ser Arg Asp Arg Asp Arg Ala Arg Pro Asp Thr Arg Leu
         1               5                  10

TCA TCG TCA GAT AAT GAG AGC GAC GAC GAA GAT TAT CAA CTG CCA CAT        337
Ser Ser Ser Asp Asn Glu Ser Asp Asp Glu Asp Tyr Gln Leu Pro His
 15                  20                  25                  30

TCA CAT CCG GAA TAT GGC AGT GAC TCG TCC GAT CAA GAC TTT GAA CTT        385
Ser His Pro Glu Tyr Gly Ser Asp Ser Ser Asp Gln Asp Phe Glu Leu
                 35                  40                  45

AAT AAT GTG GGC AAA TTT TGT CCT CTA CCA TGG AAA CCC GAT GTC GCT        433
Asn Asn Val Gly Lys Phe Cys Pro Leu Pro Trp Lys Pro Asp Val Ala
             50                  55                  60

CGG TTA TGT GCG GAT ACA AAC AAA CTA TTT CGA TGT TTT ATT CGA TGT        481
Arg Leu Cys Ala Asp Thr Asn Lys Leu Phe Arg Cys Phe Ile Arg Cys
         65                  70                  75

CGA CTA AAT AGC GGT CCG TTC CAC GAT GCT CTT CGG AGA GCA CTA TTC        529
Arg Leu Asn Ser Gly Pro Phe His Asp Ala Leu Arg Arg Ala Leu Phe
     80                  85                  90

GAT ATT CAT ATG ATT GGT CGA ATG GGA TAT CGA CTA AAA CAA GCC GAA        577
Asp Ile His Met Ile Gly Arg Met Gly Tyr Arg Leu Lys Gln Ala Glu
 95                 100                 105                 110

TGG GAA ACT ATC ATG AAT TTG ACC CCA CGC CAA AGT CTA CAT CTG CGC        625
Trp Glu Thr Ile Met Asn Leu Thr Pro Arg Gln Ser Leu His Leu Arg
                115                 120                 125

AGG ACT CTG AGG GAT GCT GAT AGT CGA AGC GCC CAT CCT ATA TCC GAT        673
Arg Thr Leu Arg Asp Ala Asp Ser Arg Ser Ala His Pro Ile Ser Asp
            130                 135                 140

ATA TAT GCC TCC GAT AGC ATT TTT CAC CCA ATC GCT GCG TCC TCG GGA        721
Ile Tyr Ala Ser Asp Ser Ile Phe His Pro Ile Ala Ala Ser Ser Gly
        145                 150                 155

ACT ATT TCT TCA GAC TGC GAT GTA AAA GGA ATG AAC GAT TTG TCG GTA        769
```

```
Thr Ile Ser Ser Asp Cys Asp Val Lys Gly Met Asn Asp Leu Ser Val
        160                 165                 170

GAC AGT AAA TTG CAT TAA CTATCCAGAC TTGAAGAGAA AGCTCTTATT           817
Asp Ser Lys Leu His
175

ATATAATTTT AATTGTTAGA CATAGAGCCG ACATTCTTTG ATCTATCTAA TGAGATAAAA   877

TAATAGATTT TGGATTTATT TGTCATGATC TGTTGCAACA AACGCTGACC CCCCCCATCC   937

ATGAAGGGGC GTGTCAAATA ACGTGTTGCC TTTTTGTTGT ATATGAAGAT ATTTAATGTG   997

GCGTTGAGCC TAATGAGAGG AGAACGTGTT TGAATACTGG AGACGAGCGC CGTGTAAGAT  1057

TAAAACATAT TGGAGAGGT  ATG GCC ATG TGG TCT CTA CGG CGC AAA TCT     1106
                      Met Ala Met Trp Ser Leu Arg Arg Lys Ser
                       1               5                  10

AGC AGG AGT GTG CAA CTC CGG GTA GAT TCT CCA AAA GAA CAG AGT TAT   1154
Ser Arg Ser Val Gln Leu Arg Val Asp Ser Pro Lys Glu Gln Ser Tyr
            15                  20                  25

GAT ATA CTT TCT GCC GGC GGG GAA CAT GTT GCG CTA TTG CCT AAA TCT   1202
Asp Ile Leu Ser Ala Gly Gly Glu His Val Ala Leu Leu Pro Lys Ser
                30                  35                  40

GTA CGC AGT CTA GCC AGG ACC ATA TTA ACC GCC GCT ACG ATC TCC CAG   1250
Val Arg Ser Leu Ala Arg Thr Ile Leu Thr Ala Ala Thr Ile Ser Gln
        45                  50                  55

GCT GCT ATG AAA GCT GGA AAA CCA CCA TCG TCT CGT TTG TGG GGT GAG   1298
Ala Ala Met Lys Ala Gly Lys Pro Pro Ser Ser Arg Leu Trp Gly Glu
    60                  65                  70

ATA TTC GAC AGA ATG ACT GTC ACG CTT AAC GAA TAT GAT ATT TCT GCT   1346
Ile Phe Asp Arg Met Thr Val Thr Leu Asn Glu Tyr Asp Ile Ser Ala
75                  80                  85                  90

TCG CCA TTC CAC CCG ACA GAC CCG ACG AGA AAA ATT GTA GGC CGG GCT   1394
Ser Pro Phe His Pro Thr Asp Pro Thr Arg Lys Ile Val Gly Arg Ala
                95                 100                 105

TTA CGG TGT ATT GAA CGT GCT CCT CTT ACA CAC GAA GAA ATG GAC ACT   1442
Leu Arg Cys Ile Glu Arg Ala Pro Leu Thr His Glu Glu Met Asp Thr
            110                 115                 120

CGG TTT ACT ATC ATG ATG TAT TGG TGT TGT CTT GGA CAT GCT GGA TAC   1490
Arg Phe Thr Ile Met Met Tyr Trp Cys Cys Leu Gly His Ala Gly Tyr
        125                 130                 135

TGT ACT GTT TCG CGC TTA TAT GAG AAG AAT GTC CGT CTT ATG GAC ATA   1538
Cys Thr Val Ser Arg Leu Tyr Glu Lys Asn Val Arg Leu Met Asp Ile
    140                 145                 150

GTA GGT TCG GCA ACG GGC TGT GGA ATA AGT CCA CTC CCC GAA ATA GAG   1586
Val Gly Ser Ala Thr Gly Cys Gly Ile Ser Pro Leu Pro Glu Ile Glu
155                 160                 165                 170

TCT TAT TGG AAA CCT TTA TGT CGT GCC GTC GCT ACT AAG GGG AAT GCA   1634
Ser Tyr Trp Lys Pro Leu Cys Arg Ala Val Ala Thr Lys Gly Asn Ala
                175                 180                 185

GCA ATC GGT GAT GAT GCT GAA TTG GCA CAT TAT CTG ACA AAT CTT CGG   1682
Ala Ile Gly Asp Asp Ala Glu Leu Ala His Tyr Leu Thr Asn Leu Arg
            190                 195                 200

GAA TCG CCA ACA GGA GAC GGG GAA TCC TAC TTA TAA CTAATCGCAC        1728
Glu Ser Pro Thr Gly Asp Gly Glu Ser Tyr Leu
        205                 210

AATTATTAAT AGGATTTTAG GAAAAACTGC TACTAACGTT GTTAAATAA TAAAATTTTA   1788

TTTTCAATAA GGCATTACAG TGTTGTCATG ATTGTATGTA TTATATGGGG TATGCATGAG  1848

GATTACTTCG ATTGAAACTT TGTCTAAATG TCTGTAGGAT TTTACTATTC ATTAGTCTGG  1908

ATCGAGGCGG ACGTAAATGG AGATTGCGGC AAATGTAGGG GTGCTGGTAC ATAAGACCTC  1968
```

-continued

```
CAACATCCAT TCGACTCATC GGCCTGCGTC CAAATGGATA TGTTGATGTA CCTTGTAAAG    2028

TTATGACATT AGAAGATCGA TGGTGAATAG TGGGATCTAT ATCCATGCTA TTCTCAATAT    2088

TGCATGATAT GCAATGTTCC CGGTTAGGTT TGATAAGATC ATGTATGGTT CTATAATACA    2148

ACTCCTCTTC AGAAGAATCA TTTATTTTAT GTCCACTGTC CTTGGATATT CCAGTTTCTG    2208

TCAATCGATT CGCTTGCATT TGCGTGCAGC ATGTCTTGAT GGCATTTCCT ATGCTATCAT    2268

CCGGCAGGCC TAAGGGTGTT CTATACTCGC ACACAGGTAG AGCAAGAACC ACGGCATATC    2328

GAGCTACCTC TATTGCCCCG CTAAGGACAT TTCTTGCAGA CTGTATTGTC ATGAACATAT    2388

TTCGTGTATT GTGTCGATCA TAACCCTTGT TGATTCCTAT GGAAAGCATT GTGGTCCAGT    2448

TTTCCAGATG AAATGAAAAC AATGCGGGCA AAAATGGTCC CACCTGTTTC ATCTTCAATG    2508

CATCTCTCAC ATCCCAAGTT CTATAGAATA TTCTCCACTG ACCAGTTTCG GTAAGATCAG    2568

TTTCTGTAAA ATTTGTGATA GTTTCAATCG AAAACATTTT GTCCATCATG GCAAAAAATC    2628

TATAGGCAGA CCAGATAACC ATTTGACACC ACATATCCTT GTGTATATCA AACGATGTAA    2688

TAGATCCCTC GTTAGTAGAT ATGGTACATA AAAGGCCTAA TCTCTCTCGG GCTTCCATAC    2748

ATTGAACGAT TCCTTCTGTG AATTCATCAA CAACCACATG CCAAAAATTT ACATTAGTAA    2808

TCTTTCTCGG TGGCTTACCA AATCGTCCTC TTGGTATATC CATATCATCG AACATTGTAG    2868

CATTGACTCT GCTCATCGTT GTCTTTCAAA TGCGCTCGAT TGTTGAATCT CTCCTGATGT    2928

TAGAAGTATA TGGAAGATAG CCTGGATACA TAAGTGATCT AGAAGGGTTT GTTATTGCAC    2988

TAATATACAA ATTATACGTG ACACTATAGC GACGGTTGTA GCGATGCACC TAATCGTAAT    3048

GTGTATACGC CCCATCATGT AATTATATCT AATTGGTAGC AAGTAGGTCT GTCGAATAAC    3108

AGCTAATGAC TACCGGCTCT ACATTTTTTC TGTATTCGTG ACTTTCCTGT CGCAGTGTAA    3168

CGAACCGGAA TTGCAATCGC ATCTCTATCT TCTTTCTTGC AACATTTTCC ACAACAGAAT    3228

AATCTGCCGG GTGTACTACT CATTTGAGGT GGTTCGATTT CCGGAGGTTT TAGAGGATTG    3288

GGTGGGGACC CGAGGATTTT GTATACACAT ACCATATCAC TGTCGCAAAA ATGCGCTCTA    3348

TCTTCTGGGG TGTCGAACTT CGGTTCCCAT GTAGATGTCA AGAGAGTTTG AATATTGTCG    3408

GGAATGGCCC ACGGCATACC GGACCAGGTC CCAGACACTT TGATTGCAAG TAACCTTTTT    3468

GGCAAAGGAA TACATTCGAG CGCAATGGCA CATATATCTG CCGCCCCAAC TATCCACAAG    3528

CTATGTGGAG CATTACCAGA AACTTCAGAT TCCAACATCA AATATCCAGA TAGAACATCC    3588

TGCCATTCTG TGGAACATCC TGCAACATCT TCAAATAGCC GCACTATAAA CGAATCCCTA    3648

GTTCCGGCCA ATCCGGTACC ACGAACTCCA GTTCCATCTG GTGGCTTTGT CCTTACTATC    3708

GGTCGATGTT GCCGAGGAAG AATTAACATG GGTTTGGCAA AACGGAATAG GTCTGCAGCT    3768

CTGGCGATTA TGGGCACACC CACATCATCC TGTATTTGTT CCATACATTG CTTTATAAGG    3828

AATATCCATA AAGTAGATGC AGCATCTCTA GATCTTCCTG GCAATCGATC GCATTCATCT    3888

AGAAGTGTGA CTATAGTTAT CATGGACACA CCCATCTTCA CCTCCACCAA TAATCTTTTT    3948

TATTGTTAAT AACTGGGCCG GTCTGATCTC CAAATCTTAT ACTCTGGTAG AATATGAAAC    4008

AGGGTTAAAA CTAGGTAATA GACTGGATGT CTTCGACTCC GGAGGCAGAA ACG   ATG    4064
                                                            Met
                                                             1

GAA TGT GGC ATT TCT TCG TCG AAA GTA CAC GAC TCT AAA ACT AAT ACT      4112
Glu Cys Gly Ile Ser Ser Ser Lys Val His Asp Ser Lys Thr Asn Thr
         5                  10                  15

ACC TAC GGA ATT ATA CAT AAC AGC ATC AAT GGT ACG GAT ACG ACG TTG      4160
Thr Tyr Gly Ile Ile His Asn Ser Ile Asn Gly Thr Asp Thr Thr Leu
     20                  25                  30
```

-continued

| | | |
|---|---|---|
| TTT GAT ACT TTT CCC GAC AGT ACC GAT AAC GCG GAA GTG ACG GGG GAT<br>Phe Asp Thr Phe Pro Asp Ser Thr Asp Asn Ala Glu Val Thr Gly Asp<br>35                  40                45 | 4208 |
| GTG GAC GAT GTG AAG ACT GAG AGC TCT CCC GAG TCC CAA TCT GAA GAT<br>Val Asp Asp Val Lys Thr Glu Ser Ser Pro Glu Ser Gln Ser Glu Asp<br>50                  55                60              65 | 4256 |
| TTG TCA CCT TTT GGG AAC GAT GGA AAT GAA TCC CCC GAA ACG GTG ACG<br>Leu Ser Pro Phe Gly Asn Asp Gly Asn Glu Ser Pro Glu Thr Val Thr<br>                  70                75                80 | 4304 |
| GAC ATT GAT GCA GTT TCA GCT GTG CGA ATG CAG TAT AAC ATT GTT TCA<br>Asp Ile Asp Ala Val Ser Ala Val Arg Met Gln Tyr Asn Ile Val Ser<br>                  85                90                95 | 4352 |
| TCG TTA CCG CCC GGA TCT GAA GGG TAT ATC TAT GTT TGT ACA AAG CGT<br>Ser Leu Pro Pro Gly Ser Glu Gly Tyr Ile Tyr Val Cys Thr Lys Arg<br>          100                105              110 | 4400 |
| GGG GAT AAT ACC AAG AGA AAA GTC ATT GTG AAA GCT GTG ACT GGT GGC<br>Gly Asp Asn Thr Lys Arg Lys Val Ile Val Lys Ala Val Thr Gly Gly<br>115                      120              125 | 4448 |
| AAA ACC CTT GGG AGT GAA ATT GAT ATA TTA AAA AAA ATG TCT CAC CGC<br>Lys Thr Leu Gly Ser Glu Ile Asp Ile Leu Lys Lys Met Ser His Arg<br>130                  135              140              145 | 4496 |
| TCC ATA ATT AGA TTA GTT CAT GCT TAT AGA TGG AAA TCG ACA GTT TGT<br>Ser Ile Ile Arg Leu Val His Ala Tyr Arg Trp Lys Ser Thr Val Cys<br>                  150              155              160 | 4544 |
| ATG GTA ATG CCT AAA TAC AAA TGC GAC TTG TTT ACG TAC ATA GAT ATC<br>Met Val Met Pro Lys Tyr Lys Cys Asp Leu Phe Thr Tyr Ile Asp Ile<br>          165                170              175 | 4592 |
| ATG GGA CCA TTG CCA CTA AAT CAA ATA ATT ACG ATA GAA CGG GGT TTG<br>Met Gly Pro Leu Pro Leu Asn Gln Ile Ile Thr Ile Glu Arg Gly Leu<br>          180                185              190 | 4640 |
| CTT GGA GCA TTG GCA TAT ATC CAC GAA AAG GGT ATA ATA CAT CGT GAT<br>Leu Gly Ala Leu Ala Tyr Ile His Glu Lys Gly Ile Ile His Arg Asp<br>195                      200              205 | 4688 |
| GTA AAA ACT GAA AAT ATA TTT TTG GAT AAA CCT GAA AAT GTA GTA TTG<br>Val Lys Thr Glu Asn Ile Phe Leu Asp Lys Pro Glu Asn Val Val Leu<br>210                  215              220              225 | 4736 |
| GGG GAC TTT GGG GCA GCA TGT AAA TTA GAT GAA CAT ACA GAT AAA CCC<br>Gly Asp Phe Gly Ala Ala Cys Lys Leu Asp Glu His Thr Asp Lys Pro<br>          230                235              240 | 4784 |
| AAA TGT TAT GGA TGG AGT GGA ACT CTG GAA ACC AAT TCG CCT GAA CTG<br>Lys Cys Tyr Gly Trp Ser Gly Thr Leu Glu Thr Asn Ser Pro Glu Leu<br>          245                250              255 | 4832 |
| CTT GCA CTT GAT CCA TAC TGT ACA AAA ACT GAT ATA TGG AGT GCA GGA<br>Leu Ala Leu Asp Pro Tyr Cys Thr Lys Thr Asp Ile Trp Ser Ala Gly<br>260                      265              270 | 4880 |
| TTA GTT CTG TTT GAG ATG TCA GTA AAA AAT ATA ACC TTT TTT GGC AAA<br>Leu Val Leu Phe Glu Met Ser Val Lys Asn Ile Thr Phe Phe Gly Lys<br>275                      280              285 | 4928 |
| CAA GTA AAC GGC TCA GGT TCT CAG CTG AGA TCC ATA ATT AGA TGC CTG<br>Gln Val Asn Gly Ser Gly Ser Gln Leu Arg Ser Ile Ile Arg Cys Leu<br>290                  295              300              305 | 4976 |
| CAA GTC CAT CCG TTG GAA TTT CCA CAG AAC AAT TCT ACA AAC TTA TGC<br>Gln Val His Pro Leu Glu Phe Pro Gln Asn Asn Ser Thr Asn Leu Cys<br>          310                315              320 | 5024 |
| AAA CAC TTC AAG CAG TAC GCG ATT CAG TTA CGA CAT CCA TAT GCA ATC<br>Lys His Phe Lys Gln Tyr Ala Ile Gln Leu Arg His Pro Tyr Ala Ile<br>          325                330              335 | 5072 |
| CCT CAG ATT ATA CGA AAG AGT GGT ATG ACG ATG GAT CTT GAA TAT GCT<br>Pro Gln Ile Ile Arg Lys Ser Gly Met Thr Met Asp Leu Glu Tyr Ala | 5120 |

```
                340                 345                  350
ATT GCA AAA ATG CTC ACA TTC GAT CAG GAG TTT AGA CCA TCT GCC CAA    5168
Ile Ala Lys Met Leu Thr Phe Asp Gln Glu Phe Arg Pro Ser Ala Gln
        355                 360                 365

GAT ATT TTA ATG TTG CCT CTT TTT ACT AAA GAA CCC GCT GAC GCA TTA    5216
Asp Ile Leu Met Leu Pro Leu Phe Thr Lys Glu Pro Ala Asp Ala Leu
370                 375                 380                 385

TAC ACG ATA ACT GCC GCT CAT ATG TAA ACACCCGTCA AAAATAACTT          5263
Tyr Thr Ile Thr Ala Ala His Met
                390

CAATGATTCA TTTTATAATA TATACTACGC GTTACCTGCA ATAATGACAA CATTCGAAGT  5323

CTTTGAAGAT TCGCAGACCT TTTTTGCGA ATG GCA CCT TCG GGA CCT ACG CCA    5376
                                Met Ala Pro Ser Gly Pro Thr Pro
                                  1                 5

TAT TCC CAC AGA CCG CAA ATA AAG CAT TAT GGA ACA TTT TCG GAT TGC    5424
Tyr Ser His Arg Pro Gln Ile Lys His Tyr Gly Thr Phe Ser Asp Cys
        10                  15                  20

ATG AGA TAT ACT CTA AAC GAT GAG AGT AAG GTA GAT GAT AGA TGT TCA    5472
Met Arg Tyr Thr Leu Asn Asp Glu Ser Lys Val Asp Asp Arg Cys Ser
25                  30                  35                  40

GAC ATA CAT AAC TCC TTA GCA CAA TCC AAT GTT ACT TCA AGC ATG TCT    5520
Asp Ile His Asn Ser Leu Ala Gln Ser Asn Val Thr Ser Ser Met Ser
                45                  50                  55

GTA ATG AAC GAT TCG GAA GAA TGT CCA TTA ATA AAT GGA CCT TCG ATG    5568
Val Met Asn Asp Ser Glu Glu Cys Pro Leu Ile Asn Gly Pro Ser Met
        60                  65                  70

CAG GCA GAG GAC CCT AAA AGT GTT TTT TAT AAA GTT CGT AAG CCT GAC    5616
Gln Ala Glu Asp Pro Lys Ser Val Phe Tyr Lys Val Arg Lys Pro Asp
        75                  80                  85

CGA AGT CGT GAT TTT TCA TGG CAA AAT CTG AAC TCC CAT GGC AAT AGT    5664
Arg Ser Arg Asp Phe Ser Trp Gln Asn Leu Asn Ser His Gly Asn Ser
        90                  95                  100

GGT CTA CGT CGT GAA AAA TAT ATA CGT TCC TCT AAG AGG CGA TGG AAG    5712
Gly Leu Arg Arg Glu Lys Tyr Ile Arg Ser Ser Lys Arg Arg Trp Lys
105                 110                 115                 120

AAT CCC GAG ATA TTT AAG GTA TCT TTG AAA TGT GAA TCA ATT GGC GCT    5760
Asn Pro Glu Ile Phe Lys Val Ser Leu Lys Cys Glu Ser Ile Gly Ala
                125                 130                 135

GGT AAC GGA ATA AAA ATT TCA TTC TCA TTT TTC TAA CATTATAATA         5806
Gly Asn Gly Ile Lys Ile Ser Phe Ser Phe Phe
                140                 145

TATCAGATCG TTTCTTATAT ACTTATTTTC ATCGTCGGGA TATGACTAAC GTATACTAAG  5866

TTACAAGAAA CAACTGCTTA ACGTCGAACA TAACGGAAAT AAAAATATAT ATAGCGTCTC  5926

CTATAACTGT TATATTGGCA CCTTTTAGAG CTTCGGT ATG AAT AGA TAC AGA TAT   5981
                                        Met Asn Arg Tyr Arg Tyr
                                          -30                 -25

GAA AGT ATT TTT TTT AGA TAT ATC TCA TCC ACG AGA ATG ATT CTT ATA    6029
Glu Ser Ile Phe Phe Arg Tyr Ile Ser Ser Thr Arg Met Ile Leu Ile
                -20                 -15                 -10

ATC TGT TTA CTT TTG GGA ACT GGG GAC ATG TCC GCA ATG GGA CTT AAG    6077
Ile Cys Leu Leu Leu Gly Thr Gly Asp Met Ser Ala Met Gly Leu Lys
            -5                   1                   5

AAA GAC AAT TCT CCG ATC ATT CCC ACA TTA CAT CCG AAA GGT AAT GAA    6125
Lys Asp Asn Ser Pro Ile Ile Pro Thr Leu His Pro Lys Gly Asn Glu
        10                  15                  20

AAC CTC CGG GCT ACT CTC AAT GAA TAC AAA ATC CCG TCT CCA CTG TTT    6173
Asn Leu Arg Ala Thr Leu Asn Glu Tyr Lys Ile Pro Ser Pro Leu Phe
25                  30                  35                  40
```

```
GAT ACA CTT GAC AAT TCA TAT GAG ACA AAA CAC GTA ATA TAT ACG GAT       6221
Asp Thr Leu Asp Asn Ser Tyr Glu Thr Lys His Val Ile Tyr Thr Asp
             45                  50                  55

AAT TGT AGT TTT GCT GTT TTG AAT CCA TTT GGC GAT CCG AAA TAT ACG       6269
Asn Cys Ser Phe Ala Val Leu Asn Pro Phe Gly Asp Pro Lys Tyr Thr
             60                  65                  70

CTT CTC AGT TTA CTG TTG ATG GGA CGA CGC AAA TAT GAT GCT CTA GTA       6317
Leu Leu Ser Leu Leu Leu Met Gly Arg Arg Lys Tyr Asp Ala Leu Val
             75                  80                  85

GCA TGG TTT GTC TTG GGC AGA GCA TGT GGG AGA CCA ATT TAT TTA CGT       6365
Ala Trp Phe Val Leu Gly Arg Ala Cys Gly Arg Pro Ile Tyr Leu Arg
             90                  95                 100

GAA TAT GCC AAC TGC TCT ACT AAT GAA CCA TTT GGA ACT TGT AAA TTA       6413
Glu Tyr Ala Asn Cys Ser Thr Asn Glu Pro Phe Gly Thr Cys Lys Leu
105                 110                 115                 120

AAG TCC CTA GGA TGG TGG GAT AGA AGA TAT GCA ATG ACG AGT TAT ATC       6461
Lys Ser Leu Gly Trp Trp Asp Arg Arg Tyr Ala Met Thr Ser Tyr Ile
                125                 130                 135

GAT CGA GAT GAA TTG AAA TTG ATT ATT GCA GCA CCC AGT CGT GAG CTA       6509
Asp Arg Asp Glu Leu Lys Leu Ile Ile Ala Ala Pro Ser Arg Glu Leu
                140                 145                 150

AGT GGA TTA TAT ACG CGT TTA ATA ATT ATT AAT GGA GAA CCC ATT TCG       6557
Ser Gly Leu Tyr Thr Arg Leu Ile Ile Ile Asn Gly Glu Pro Ile Ser
                155                 160                 165

AGT GAC ATA TTA CTG ACT GTT AAA GGA ACA TGT AGT TTT TCG AGA CGG       6605
Ser Asp Ile Leu Leu Thr Val Lys Gly Thr Cys Ser Phe Ser Arg Arg
            170                 175                 180

GGG ATA AAG GAT AAC AAA CTA TGC AAA CCG TTC AGT TTT TTT GTC AAT       6653
Gly Ile Lys Asp Asn Lys Leu Cys Lys Pro Phe Ser Phe Phe Val Asn
185                 190                 195                 200

GGT ACA ACA CGG CTG TTA GAC ATG GTG CGA ACA GGA ACC CCG AGA GCC       6701
Gly Thr Thr Arg Leu Leu Asp Met Val Arg Thr Gly Thr Pro Arg Ala
                205                 210                 215

CAT GAA GAA AAT GTG AAG CAG TGG CTT GAA CGA AAT GGT GGT AAA CAT       6749
His Glu Glu Asn Val Lys Gln Trp Leu Glu Arg Asn Gly Gly Lys His
                220                 225                 230

CTA CCA ATC GTC GTC GAA ACA TCT ATG CAA CAA GTC TCA AAT TTG CCG       6797
Leu Pro Ile Val Val Glu Thr Ser Met Gln Gln Val Ser Asn Leu Pro
            235                 240                 245

AGA AGT TTT AGA GAT TCA TAT TTA AAA TCA CCT GAC GAC GAT AAA TAT       6845
Arg Ser Phe Arg Asp Ser Tyr Leu Lys Ser Pro Asp Asp Asp Lys Tyr
            250                 255                 260

AAT GAC GTC AAA ATG ACA TCG GCC ACT ACT AAT AAC ATT ACC ACC TCC       6893
Asn Asp Val Lys Met Thr Ser Ala Thr Thr Asn Asn Ile Thr Thr Ser
265                 270                 275                 280

GTG GAT GGT TAC ACT GGA CTC ACT AAT CGG CCC GAG GAC TTT GAG AAA       6941
Val Asp Gly Tyr Thr Gly Leu Thr Asn Arg Pro Glu Asp Phe Glu Lys
                285                 290                 295

GCA CCA TAC ATA ACT AAA CGA CCG ATA ATC TCT GTC GAG GAG GCA TCC       6989
Ala Pro Tyr Ile Thr Lys Arg Pro Ile Ile Ser Val Glu Glu Ala Ser
                300                 305                 310

AGT CAA TCA CCT AAA ATA TCA ACA GAA AAA AAA TCC CGA ACG CAA ATA       7037
Ser Gln Ser Pro Lys Ile Ser Thr Glu Lys Lys Ser Arg Thr Gln Ile
            315                 320                 325

ATA ATT TCA CTA GTT GTT CTA TGC GTC ATG TTT TGT TTC ATT GTA ATC       7085
Ile Ile Ser Leu Val Val Leu Cys Val Met Phe Cys Phe Ile Val Ile
            330                 335                 340

GGG TCT GGT ATA TGG ATC CTT CGC AAA CAC CGC AAA ACG GTG ATG TAT       7133
Gly Ser Gly Ile Trp Ile Leu Arg Lys His Arg Lys Thr Val Met Tyr
```

```
345                  350                  355                  360
GAT AGA CGT CGT CCA TCA AGA CGG GCA TAT TCC CGC CTA TAA            7175
Asp Arg Arg Arg Pro Ser Arg Arg Ala Tyr Ser Arg Leu
                365                 370

CACGTGTTTG GTATGGGCGT GTCGCTATAG TGCATAAGAA GTTGACTACA TTGATCAATG   7235

ACATTATATA GCTTCTTTGG TCAGATAGAC GGCGTGTGTG ATTGCG ATG TAT GTA     7290
                                                 Met Tyr Val

CTA CAA TTA TTA TTT TGG ATC CGC CTC TTT CGA GGC ATC TGG TCT ATA    7338
Leu Gln Leu Leu Phe Trp Ile Arg Leu Phe Arg Gly Ile Trp Ser Ile
-15             -10                 -5                    1

GTT TAT ACT GGA ACA TCT GTT ACG TTA TCA ACG GAC CAA TCT GCT CTT    7386
Val Tyr Thr Gly Thr Ser Val Thr Leu Ser Thr Asp Gln Ser Ala Leu
            5                   10                  15

GTT GCG TTC CGC GGA TTA GAT AAA ATG GTG AAT GTA CGC GGC CAA CTT    7434
Val Ala Phe Arg Gly Leu Asp Lys Met Val Asn Val Arg Gly Gln Leu
        20                  25                  30

TTA TTC CTG GGC GAC CAG ACT CGG ACC AGT TCT TAT ACA GGA ACG ACG    7482
Leu Phe Leu Gly Asp Gln Thr Arg Thr Ser Ser Tyr Thr Gly Thr Thr
    35                  40                  45

GAA ATC TTG AAA TGG GAT GAA GAA TAT AAA TGC TAT TCC GTT CTA CAT    7530
Glu Ile Leu Lys Trp Asp Glu Glu Tyr Lys Cys Tyr Ser Val Leu His
50                  55                  60                  65

GCG ACA TCA TAT ATG GAT TGT CCT GCT ATA GAC GCC ACG GTA TTC AGA    7578
Ala Thr Ser Tyr Met Asp Cys Pro Ala Ile Asp Ala Thr Val Phe Arg
                70                  75                  80

GGC TGT AGA GAC GCT GTG GTA TAT GCT CAA CCT CAT GGT AGA GTA CAA    7626
Gly Cys Arg Asp Ala Val Val Tyr Ala Gln Pro His Gly Arg Val Gln
            85                  90                  95

CCT TTT CCC GAA AAG GGA ACA TTG TTG AGA ATT GTC GAA CCC AGA GTA    7674
Pro Phe Pro Glu Lys Gly Thr Leu Leu Arg Ile Val Glu Pro Arg Val
        100                 105                 110

TCA GAT ACA GGC AGC TAT TAC ATA CGT GTA TCT CTC GCT GGA AGA AAT    7722
Ser Asp Thr Gly Ser Tyr Tyr Ile Arg Val Ser Leu Ala Gly Arg Asn
    115                 120                 125

ATG AGC GAT ATA TTT AGA ATG GTT GTT ATT ATA AGG AGT AGC AAA TCT    7770
Met Ser Asp Ile Phe Arg Met Val Val Ile Ile Arg Ser Ser Lys Ser
130                 135                 140                 145

TGG GCC TGT AAT CAC TCT GCT AGT TCA TTT CAG GCC CAT AAA TGT ATT    7818
Trp Ala Cys Asn His Ser Ala Ser Ser Phe Gln Ala His Lys Cys Ile
                150                 155                 160

CGC TAT GTC GAC CGT ATG GCC TTT GAA AAT TAT CTG ATT GGA CAT GTA    7866
Arg Tyr Val Asp Arg Met Ala Phe Glu Asn Tyr Leu Ile Gly His Val
            165                 170                 175

GGC AAT TTG CTG GAC AGT GAC TCG GAA TTG CAT GCA ATT TAT AAT ATT    7914
Gly Asn Leu Leu Asp Ser Asp Ser Glu Leu His Ala Ile Tyr Asn Ile
        180                 185                 190

ACT CCC CAA TCC ATT TCC ACA GAT ATT AAT ATT GTA ACG ACT CCA TTT    7962
Thr Pro Gln Ser Ile Ser Thr Asp Ile Asn Ile Val Thr Thr Pro Phe
    195                 200                 205

TAC GAT AAT TCG GGA ACA ATT TAT TCA CCT ACG GTT TTT AAT TTG TTT    8010
Tyr Asp Asn Ser Gly Thr Ile Tyr Ser Pro Thr Val Phe Asn Leu Phe
210                 215                 220                 225

AAT AAC AAT TCC CAT GTC GAT GCA ATG AAT TCG ACT GGT ATG TGG AAT    8058
Asn Asn Asn Ser His Val Asp Ala Met Asn Ser Thr Gly Met Trp Asn
                230                 235                 240

ACC GTT TTA AAA TAT ACC CTT CCA AGG CTT ATT TAC TTT TCT ACG ATG    8106
Thr Val Leu Lys Tyr Thr Leu Pro Arg Leu Ile Tyr Phe Ser Thr Met
            245                 250                 255
```

```
                                                              -continued

ATT GTA CTA TGT ATA ATA GCA TTG GCA ATT TAT TTG GTC TGT GAA AGG         8154
Ile Val Leu Cys Ile Ile Ala Leu Ala Ile Tyr Leu Val Cys Glu Arg
            260                 265                 270

TGC CGC TCT CCC CAT CGT AGG ATA TAC ATC GGT GAA CCA AGA TCT GAT         8202
Cys Arg Ser Pro His Arg Arg Ile Tyr Ile Gly Glu Pro Arg Ser Asp
275                 280                 285

GAG GCC CCA CTC ATC ACT TCT GCA GTT AAC GAA TCA TTT CAA TAT GAT         8250
Glu Ala Pro Leu Ile Thr Ser Ala Val Asn Glu Ser Phe Gln Tyr Asp
290                 295                 300                 305

TAT AAT GTA AAG GAA ACT CCT TCA GAT GTT ATT GAA AAG GAG TTG ATG         8298
Tyr Asn Val Lys Glu Thr Pro Ser Asp Val Ile Glu Lys Glu Leu Met
                310                 315                 320

GAA AAA CTG AAG AAG AAA GTC GAA TTG TTG GAA AGA GAA GAA TGT GTA         8346
Glu Lys Leu Lys Lys Lys Val Glu Leu Leu Glu Arg Glu Glu Cys Val
            325                 330                 335

TAG GTTTGAGAAA CTATTATAGG TAGGTGGTAC CTGTTAGCTT AGTATAAGGG              8399
End

GAGGAGCCGT TCTTGTTTTT AAAGACACGA ACACAAGGCC GTAAGTTTTA TATGTGAATT       8459

TTGTGCATGT CTGCGAGTCA GCGTCATA ATG TGT GTT TTC CAA ATC CTG ATA          8511
                              Met Cys Val Phe Gln Ile Leu Ile
                                                  -15

ATA GTG ACG ACG ATC AAA GTA GCT GGA ACG GCC AAC ATA AAT CAT ATA         8559
Ile Val Thr Thr Ile Lys Val Ala Gly Thr Ala Asn Ile Asn His Ile
-10                 -5                  1                   5

GAC GTT CCT GCA GGA CAT TCT GCT ACA ACG ACG ATC CCG CGA TAT CCA         8607
Asp Val Pro Ala Gly His Ser Ala Thr Thr Thr Ile Pro Arg Tyr Pro
                10                  15                  20

CCA GTT GTC GAT GGG ACC CTT TAC ACC GAG ACG TGG ACA TGG ATT CCC         8655
Pro Val Val Asp Gly Thr Leu Tyr Thr Glu Thr Trp Thr Trp Ile Pro
            25                  30                  35

AAT CAC TGC AAC GAA ACG GCA ACA GGC TAT GTA TGT CTG GAA AGT GCT         8703
Asn His Cys Asn Glu Thr Ala Thr Gly Tyr Val Cys Leu Glu Ser Ala
40                  45                  50

CAC TGT TTT ACC GAT TTG ATA TTA GGA GTA TCC TGC ATG AGG TAT GCG         8751
His Cys Phe Thr Asp Leu Ile Leu Gly Val Ser Cys Met Arg Tyr Ala
55                  60                  65                  70

GAT GAA ATC GTC TTA CGA ACT GAT AAA TTT ATT GTC GAT GCG GGA TCC         8799
Asp Glu Ile Val Leu Arg Thr Asp Lys Phe Ile Val Asp Ala Gly Ser
                75                  80                  85

ATT AAA CAA ATA GAA TCG CTA AGT CTG AAT GGA GTT CCG AAT ATA TTC         8847
Ile Lys Gln Ile Glu Ser Leu Ser Leu Asn Gly Val Pro Asn Ile Phe
            90                  95                  100

CTA TCT ACG AAA GCA AGT AAC AAG TTG GAG ATA CTA AAT GCT AGC CTA         8895
Leu Ser Thr Lys Ala Ser Asn Lys Leu Glu Ile Leu Asn Ala Ser Leu
        105                 110                 115

CAA AAT GCG GGT ATC TAC ATT CGG TAT TCT AGA AAT GGG ACG AGG ACT         8943
Gln Asn Ala Gly Ile Tyr Ile Arg Tyr Ser Arg Asn Gly Thr Arg Thr
120                 125                 130

GCA AAG CTG GAT GTT GTT GTG GTT GGC GTT TTG GGT CAA GCA AGG GAT         8991
Ala Lys Leu Asp Val Val Val Val Gly Val Leu Gly Gln Ala Arg Asp
135                 140                 145                 150

CGC CTA CCC CAA ATG TCC AGT CCT ATG ATC TCA TCC CAC GCC GAT ATC         9039
Arg Leu Pro Gln Met Ser Ser Pro Met Ile Ser Ser His Ala Asp Ile
                155                 160                 165

AAG TTG TCA TTA AAA AAC TTT AAA GCA TTA GTA TAT CAC GTG GGA GAT         9087
Lys Leu Ser Leu Lys Asn Phe Lys Ala Leu Val Tyr His Val Gly Asp
            170                 175                 180

ACT ATC AAT GTC TCG ACG GCG GTT ATA CTA GGA CCT TCT CCG GAG ATA         9135
Thr Ile Asn Val Ser Thr Ala Val Ile Leu Gly Pro Ser Pro Glu Ile
```

```
              185                 190                 195
TTC ACA TTG GAA TTT AGG GTG TTG TTC CTC CGT TAT AAT CCA ACG TGC       9183
Phe Thr Leu Glu Phe Arg Val Leu Phe Leu Arg Tyr Asn Pro Thr Cys
    200                 205                 210

AAG TTC GTC ACG ATT TAT GAA CCT TGT ATA TTT CAC CCC AAA GAA CCA       9231
Lys Phe Val Thr Ile Tyr Glu Pro Cys Ile Phe His Pro Lys Glu Pro
215                 220                 225                 230

GAG TGT ATT ACT ACT GCA GAA CAA TCG GTA TGT CAT TTC GCA TCC AAC       9279
Glu Cys Ile Thr Thr Ala Glu Gln Ser Val Cys His Phe Ala Ser Asn
                235                 240                 245

ATT GAC ATT CTG CAG ATA GCC GCC GCA CGT TCT GAA AAT TGT AGC ACA       9327
Ile Asp Ile Leu Gln Ile Ala Ala Ala Arg Ser Glu Asn Cys Ser Thr
            250                 255                 260

GGG TAT CGT AGA TGT ATT TAT GAC ACG GCT ATC GAT GAA TCT GTG CAG       9375
Gly Tyr Arg Arg Cys Ile Tyr Asp Thr Ala Ile Asp Glu Ser Val Gln
        265                 270                 275

GCC AGA TTA ACA TTC ATA GAA CCA GGA ATT CCT TCC TTT AAA ATG AAA       9423
Ala Arg Leu Thr Phe Ile Glu Pro Gly Ile Pro Ser Phe Lys Met Lys
    280                 285                 290

GAT GTC CAG GTA GAC GAT GCT GGA TTG TAT GTG GTT GTG GCT TTA TAC       9471
Asp Val Gln Val Asp Asp Ala Gly Leu Tyr Val Val Val Ala Leu Tyr
295                 300                 305                 310

AAT GGA CGT CCA AGT GCA TGG ACT TAC ATT TAT TTG TCA ACG GTG GAA       9519
Asn Gly Arg Pro Ser Ala Trp Thr Tyr Ile Tyr Leu Ser Thr Val Glu
                315                 320                 325

ACA TAT CTT AAT GTA TAT GAA AAC TAC CAC AAG CCG GGA TTT GGG TAT       9567
Thr Tyr Leu Asn Val Tyr Glu Asn Tyr His Lys Pro Gly Phe Gly Tyr
            330                 335                 340

AAA TCA TTT CTA CAG AAC AGT AGT ATC GTC GAC GAA AAT GAG GCT AGC       9615
Lys Ser Phe Leu Gln Asn Ser Ser Ile Val Asp Glu Asn Glu Ala Ser
        345                 350                 355

GAT TGG TCC AGC TCG TCC ATT AAA CGG AGA AAT AAT GGT ACT ATC ATT       9663
Asp Trp Ser Ser Ser Ser Ile Lys Arg Arg Asn Asn Gly Thr Ile Ile
    360                 365                 370

TAT GAT ATT TTA CTC ACA TCG CTA TCA ATT GGG GCG ATT ATT ATC GTC       9711
Tyr Asp Ile Leu Leu Thr Ser Leu Ser Ile Gly Ala Ile Ile Ile Val
375                 380                 385                 390

ATA GTA GGG GGT GTT TGT ATT GCC ATA TTA ATT AGG CGT AGG AGA CGA       9759
Ile Val Gly Gly Val Cys Ile Ala Ile Leu Ile Arg Arg Arg Arg Arg
                395                 410                 415

CGT CGC ACG AGG GGG TTA TTC GAT GAA TAT CCC AAA TAT ATG ACG CTA       9807
Arg Arg Thr Arg Gly Leu Phe Asp Glu Tyr Pro Lys Tyr Met Thr Leu
            420                 425                 430

CCA GGA AAC GAT CTG GGG GGC ATG AAT GTA CCG TAT GAT AAT ACA TGC       9855
Pro Gly Asn Asp Leu Gly Gly Met Asn Val Pro Tyr Asp Asn Thr Cys
        435                 440                 445

TCT GGT AAC CAA GTT GAA TAT TAT CAA GAA AAG TCG GCT AAA ATG AAA       9903
Ser Gly Asn Gln Val Glu Tyr Tyr Gln Glu Lys Ser Ala Lys Met Lys
    450                 455                 460

AGA ATG GGT TCG GGT TAT ACC GCT TGG CTA AAA AAT GAT ATG CCG AAA       9951
Arg Met Gly Ser Gly Tyr Thr Ala Trp Leu Lys Asn Asp Met Pro Lys
465                 470                 475                 480

ATT AGG AAA CGC TTA GAT TTA TAC CAC TGA TATGTACATA TTTAAACTTA         10001
Ile Arg Lys Arg Leu Asp Leu Tyr His End
                485

ATGGGATATA GTATATGGAC GTCTATATGA CGAGAGTAAA TAAACTGACA ATGCAAATGA     10061

AGCTGATCTA TATTGTGCTT TATATTGGGA CAAACCACTC GCACAAGCTC ATTCAACACA     10121

TCCACTCTTG CTATTAAATT CCCCATTATA TAACAATACT GACATAACAC TCATATTAAG    10181
```

```
GGGAGAAAAT AAATATGCAT GGCCGATCAT ATTTTATTGA GATCCGAAAA TATATCATGC    10241

AAATAAGCAT GTTCTAGCAC CACTGCAACA TGTGGTTTAT CGATTTCCGG AAAGAATAGT    10301

TGAACCATTG CCTCCGAGCA GTTGGCGATC CGTTGACCTG CAGGTCGAC               10350
```

(2) INFORMATION FOR SEQ ID NO:2:

(i) SEQUENCE CHARACTERISTICS:
        (A) LENGTH: 10350 base pairs
        (B) TYPE: nucleic acid
        (C) STRANDEDNESS: double
        (D) TOPOLOGY: linear (ii) MOLECULE TYPE:
        (A) DESCRIPTION: genomic DNA (iii) HYPOTHETICAL: Yes (iv) ANTI-SENSE: Yes (vi) ORIGINAL SOURCE:
        (A) ORGANISM: MDV, GA strain (vii) IMMEDIATE SOURCE:
        (A) LIBRARY: genomic (xi) SEQUENCE DESCRIPTION: SEQ ID NO:2:

```
GTCGACCTGC AGGTCAACGG ATCGCCAACT GCTCGGAGGC AATGGTTCAA CTATTCTTTC      60

CGGAAATCGA TAAACCACAT GTTGCAGTGG TGCTAGAACA TGCTTATTTG CATGATATAT     120

TTTCGGATCT CAATAAAATA TGATCGGCCA TGCATATTTA TTTTCTCCCC TTAATATGAG     180

TGTTATGTCA GTATTGTTAT ATAATGGGGA ATTTAATAGC AAGAGTGGAT GTGTTGAATG     240

AGCTTGTGCG AGTGGTTTGT CCCAATATAA AGCACAATAT AGATCAGCTT CATTTGCATT     300

GTCAGTTTAT TTACTCTCGT CATATAGACG TCCATATACT ATATCCCATT AAGTTTAAAT     360

ATGTACATAT CAGTGGTATA AATCTAAGCG TTTCCTAATT TTCGGCATAT CATTTTTTAG     420

CCAAGCGGTA TAACCCGAAC CCATTCTTTT CATTTTAGCC GACTTTTCTT GATAATATTC     480

AACTTGGTTA CCAGAGCATG TATTATCATA CGGTACATTC ATGCCCCCCA GATCGTTTCC     540

TGGTAGCGTC ATATATTTGG GATATTCATC GAATAACCCC CTCGTGCGAC GTCGTCTCCT     600

ACGCCTAATT AATATGGCAA TACAAACACC CCCTACTATG ACGATAATAA TCGCCCCAAT     660

TGATAGCGAT GTGAGTAAAA TATCATAAAT GATAGTACCA TTATTTCTCC GTTTAATGGA     720

CGAGCTGGAC CAATCGCTAG CCTCATTTTC GTCGACGATA CTACTGTTCT GTAGAAATGA     780

TTTATACCCA ATCCCGGCT TGTGGTAGTT TTCATATACA TTAAGATATG TTTCCACCGT      840

TGACAAATAA ATGTAAGTCC ATGCACTTGG ACGTCCATTG TATAAAGCCA CAACCACATA     900

CAATCCAGCA TCGTCTACCT GGACATCTTT CATTTTAAAG GAAGGAATTC CTGGTTCTAT     960

GAATGTTAAT CTGGCCTGCA CAGATTCATC GATAGCCGTG TCATAAATAC ATCTACGATA    1020

CCCTGTGCTA CAATTTTCAG AACGTGCGGC GGCTATCTGC AGAATGTCAA TGTTGGATGC    1080

GAAATGACAT ACCGATTGTT CTGCAGTAGT AATACACTCT GGTTCTTTGG GGTGAAATAT    1140

ACAAGGTTCA TAAATCGTGA CGAACTTGCA CGTTGGATTA TAACGGAGGA CAACACCCT     1200

AAATTCCAAT GTGAATATCT CCGGAGAAGG TCCTAGTATA ACCGCCGTCG AGACATTGAT    1260

AGTATCTCCC ACGTGATATA CTAATGCTTT AAAGTTTTTT AATGACAACT TGATATCGGC    1320

GTGGGATGAG ATCATAGGAC TGGACATTTG GGGTAGGCGA TCCCTTGCTT GACCCAAAAC    1380

GCCAACCACA ACAACATCCA GCTTTGCAGT CCTCGTCCCA TTTCTAGAAT ACCGAATGTA    1440
```

```
GATACCCGCA TTTTGTAGGC TAGCATTTAG TATCTCCAAC TTGTTACTTG CTTTCGTAGA    1500

TAGGAATATA TTCGGAACTC CATTCAGACT TAGCGATTCT ATTTGTTTAA TGGATCCCGC    1560

ATCGACAATA AATTTATCAG TTCGTAAGAC GATTTCATCC GCATACCTCA TGCAGGATAC    1620

TCCTAATATC AAATCGGTAA AACAGTGAGC ACTTTCCAGA CATACATAGC CTGTTGCCGT    1680

TTCGTTGCAG TGATTGGGAA TCCATGTCCA CGTCTCGGTG TAAAGGGTCC CATCGACAAC    1740

TGGTGGATAT CGCGGGATCG TCGTTGTAGC AGAATGTCCT GCAGGAACGT CTATATGATT    1800

TATGTTGGCC GTTCCAGCTA CTTTGATCGT CGTCACTATT ATCAGGATTT GGAAAACACA    1860

CATTATGACG CTGACTCGCA GACATGCACA AAATTCACAT ATAAAACTTA CGGCCTTGTG    1920

TTCGTGTCTT TAAAACAAGA AACGGCTCCT CCCCTTATAC TAAGCTAACA GGTACCACCT    1980

ACCTATAATA GTTTCTCAAA CCTATACACA TTCTTCTCTT TCCAACAATT CGACTTTCTT    2040

CTTCAGTTTT TCCATCAACT CCTTTTCAAT AACATCTGAA GGAGTTTCCT TTACATTATA    2100

ATCATATTGA AATGATTCGT TAACTGCAGA AGTGATGAGT GGGGCCTCAT CAGATCTTGG    2160

TTCACCGATG TATATCCTAC GATGGGGAGA GCGGCACCTT TCACAGACCA AATAAATTGC    2220

CAATGCTATT ATACATAGTA CAATCATCGT AGAAAAGTAA ATAAGCCTTG GAAGGGTATA    2280

TTTTAAAACG GTATTCCACA TACCAGTCGA ATTCATTGCA TCGACATGGG AATTGTTATT    2340

AAACAAATTA AAAACCGTAG GTGAATAAAT TGTTCCCGAA TTATCGTAAA ATGGAGTCGT    2400

TACAATATTA ATATCTGTGG AAATGGATTG GGGAGTAATA TTATAAATTG CATGCAATTC    2460

CGAGTCACTG TCCAGCAAAT TGCCTACATG TCCAATCAGA TAATTTTCAA AGGCCATACG    2520

GTCGACATAG CGAATACATT TATGGGCCTG AAATGAACTA GCAGAGTGAT TACAGGCCCA    2580

AGATTTGCTA CTCCTTATAA TAACAACCAT TCTAAATATA TCGCTCATAT TTCTTCCAGC    2640

GAGAGATACA CGTATGTAAT AGCTGCCTGT ATCTGATACT CTGGGTTCGA CAATTCTCAA    2700

CAATGTTCCC TTTTCGGGAA AAGGTTGTAC TCTACCATGA GGTTGAGCAT ATACCACAGC    2760

GTCTCTACAG CCTCTGAATA CCGTGGCGTC TATAGCAGGA CAATCCATAT ATGATGTCGC    2820

ATGTAGAACG GAATAGCATT TATATTCTTC ATCCCATTTC AAGATTTCCG TCGTTCCTGT    2880

ATAAGAACTG GTCCGAGTCT GGTCGCCCAG GAATAAAAGT TGGCCGCGTA CATTCACCAT    2940

TTTATCTAAT CCGCGGAACG CAACAAGAGC AGATTGGTCC GTTGATAACG TAACAGATGT    3000

TCCAGTATAA ACTATAGACC AGATGCCTCG AAAGAGGCGG ATCCAAAATA ATAATTGTAG    3060

TACATACATC GCAATCACAC ACGCCGTCTA TCTGACCAAA GAAGCTATAT AATGTCATTG    3120

ATCAATGTAG TCAACTTCTT ATGCACTATA GCGACACGCC CATACCAAAC ACGTGTTATA    3180

GGCGGGAATA TGCCCGTCTT GATGGACGAC GTCTATCATA CATCACCGTT TTGCGGTGTT    3240

TGCGAAGGAT CCATATACCA GACCCGATTA CAATGAAACA AAACATGACG CATAGAACAA    3300

CTAGTGAAAT TATTATTTGC GTTCGGGATT TTTTTTCTGT TGATATTTTA GGTGATTGAC    3360

TGGATGCCTC CTCGACAGAG ATTATCGGTC GTTTAGTTAT GTATGGTGCT TTCTCAAAGT    3420

CCTCGGGCCG ATTAGTGAGT CCAGTGTAAC CATCCACGGA GGTGGTAATG TTATTAGTAG    3480

TGGCCGATGT CATTTTGACG TCATTATATT TATCGTCGTC AGGTGATTTT AAATATGAAT    3540

CTCTAAAACT TCTCGGCAAA TTTGAGACTT GTTGCATAGA TGTTTCGACG ACGATTGGTA    3600

GATGTTTACC ACCATTTCGT TCAAGCCACT GCTTCACATT TTCTTCATGG GCTCTCGGGG    3660

TTCCTGTTCG CACCATGTCT AACAGCCGTG TTGTACCATT GACAAAAAAA CTGAACGGTT    3720

TGCATAGTTT GTTATCCTTT ATCCCCCGTC TCGAAAAACT ACATGTTCCT TTAACAGTCA    3780

GTAATATGTC ACTCGAAATG GGTTCTCCAT TAATAATTAT TAAACGCGTA TATAATCCAC    3840
```

```
TTAGCTCACG ACTGGGTGCT GCAATAATCA ATTTCAATTC ATCTCGATCG ATATAACTCG    3900

TCATTGCATA TCTTCTATCC CACCATCCTA GGGACTTTAA TTTACAAGTT CCAAATGGTT    3960

CATTAGTAGA GCAGTTGGCA TATTCACGTA AATAAATTGG TCTCCCACAT GCTCTGCCCA    4020

AGACAAACCA TGCTACTAGA GCATCATATT TGCGTCGTCC CATCAACAGT AAACTGAGAA    4080

GCGTATATTT CGGATCGCCA AATGGATTCA AAACAGCAAA ACTACAATTA TCCGTATATA    4140

TTACGTGTTT TGTCTCATAT GAATTGTCAA GTGTATCAAA CAGTGGAGAC GGGATTTTGT    4200

ATTCATTGAG AGTAGCCCGG AGGTTTTCAT TACCTTTCGG ATGTAATGTG GGAATGATCG    4260

GAGAATTGTC TTTCTTAAGT CCCATTGCGG ACATGTCCCC AGTTCCCAAA AGTAAACAGA    4320

TTATAAGAAT CATTCTCGTG GATGAGATAT ATCTAAAAAA AATACTTTCA TATCTGTATC    4380

TATTCATACC GAAGCTCTAA AAGGTGCCAA TATAACAGTT ATAGGAGACG CTATATATAT    4440

TTTTATTTCC GTTATGTTCG ACGTTAAGCA GTTGTTTCTT GTAACTTAGT ATACGTTAGT    4500

CATATCCCGA CGATGAAAAT AAGTATATAA GAAACGATCT GATATATTAT AATGTTAGAA    4560

AAATGAGAAT GAAATTTTTA TTCCGTTACC AGCGCCAATT GATTCACATT TCAAAGATAC    4620

CTTAAATATC TCGGGATTCT TCCATCGCCT CTTAGAGGAA CGTATATATT TTTCACGACG    4680

TAGACCACTA TTGCCATGGG AGTTCAGATT TTGCCATGAA AAATCACGAC TTCGGTCAGG    4740

CTTACGAACT TTATAAAAAA CACTTTTAGG GTCCTCTGCC TGCATCGAAG GTCCATTTAT    4800

TAATGGACAT TCTTCCGAAT CGTTCATTAC AGACATGCTT GAAGTAACAT TGGATTGTGC    4860

TAAGGAGTTA TGTATGTCTG AACATCTATC ATCTACCTTA CTCTCATCGT TTAGAGTATA    4920

TCTCATGCAA TCCGAAAATG TTCCATAATG CTTTATTTGC GGTCTGTGGG AATATGGCGT    4980

AGGTCCCGAA GGTGCCATTC GCAAAAAAGG TCTGCGAATC TTCAAAGACT TCGAATGTTG    5040

TCATTATTGC AGGTAACGCG TAGTATATAT TATAAAATGA ATCATTGAAG TTATTTTTGA    5100

CGGGTGTTTA CATATGAGCG GCAGTTATCG TGTATAATGC GTCAGCGGGT TCTTTAGTAA    5160

AAAGAGGCAA CATTAAAATA TCTTGGGCAG ATGGTCTAAA CTCCTGATCG AATGTGAGCA    5220

TTTTTGCAAT AGCATATTCA AGATCCATCG TCATACCACT CTTTCGTATA ATCTGAGGGA    5280

TTGCATATGG ATGTCGTAAC TGAATCGCGT ACTGCTTGAA GTGTTTGCAT AAGTTTGTAG    5340

AATTGTTCTG TGGAAATTCC AACGGATGGA CTTGCAGGCA TCTAATTATG GATCTCAGCT    5400

GAGAACCTGA GCCGTTTACT TGTTTGCCAA AAAAGGTTAT ATTTTTTACT GACATCTCAA    5460

ACAGAACTAA TCCTGCACTC CATATATCAG TTTTTGTACA GTATGGATCA AGTGCAAGCA    5520

GTTCAGGCGA ATTGGTTTCC AGAGTTCCAC TCCATCCATA ACATTTGGGT TTATCTGTAT    5580

GTTCATCTAA TTTACATGCT GCCCCAAAGT CCCCCAATAC TACATTTTCA GGTTTATCCA    5640

AAAATATATT TTCAGTTTTT ACATCACGAT GTATTATACC CTTTTCGTGG ATATATGCCA    5700

ATGCTCCAAG CAAACCCCGT TCTATCGTAA TTATTTGATT TAGTGGCAAT GGTCCCATGA    5760

TATCTATGTA CGTAAACAAG TCGCATTTGT ATTTAGGCAT TACCATACAA ACTGTCGATT    5820

TCCATCTATA AGCATGAACT AATCTAATTA TGGAGCGGTG AGACATTTTT TTTAATATAT    5880

CAATTTCACT CCCAAGGGTT TTGCCACCAG TCACAGCTTT CACAATGACT TTTCTCTTGG    5940

TATTATCCCC ACGCTTTGTA CAAACATAGA TATACCCTTC AGATCGGGC GGTAACGATG     6000

AAACAATGTT ATACTGCATT CGCACAGCTG AAACTGCATC AATGTCCGTC ACCGTTTCGG    6060

GGGATTCATT TCCATCGTTC CCAAAAGGTG ACAAATCTTC AGATTGGGAC TCGGGAGAGC    6120

TCTCAGTCTT CACATCGTCC ACATCCCCCG TCACTTCCGC GTTATCGGTA CTGTCGGGAA    6180
```

-continued

```
AAGTATCAAA CAACGTCGTA TCCGTACCAT TGATGCTGTT ATGTATAATT CCGTAGGTAG      6240

TATTAGTTTT AGAGTCGTGT ACTTTCGACG AAGAAATGCC ACATTCCATC GTTTCTGCCT      6300

CCGGAGTCGA AGACATCCAG TCTATTACCT AGTTTTAACC CTGTTTCATA TTCTACCAGA      6360

GTATAAGATT TGGAGATCAG ACCGGCCCAG TTATTAACAA TAAAAAAGAT TATTGGTGGA      6420

GGTGAAG  ATG GGT GTG TCC ATG ATA ACT ATA GTC ACA CTT CTA GAT GAA       6469
         Met Gly Val Ser Met Ile Thr Ile Val Thr Leu Leu Asp Glu
          1               5                  10

TGC GAT CGA TTG CCA GGA AGA TCT AGA GAT GCT GCA TCT ACT TTA TGG        6517
Cys Asp Arg Leu Pro Gly Arg Ser Arg Asp Ala Ala Ser Thr Leu Trp
 15              20                  25                  30

ATA TTC CTT ATA AAG CAA TGT ATG GAA CAA ATA CAG GAT GAT GTG GGT        6565
Ile Phe Leu Ile Lys Gln Cys Met Glu Gln Ile Gln Asp Asp Val Gly
                 35                  40                  45

GTG CCC ATA ATC GCC AGA GCT GCA GAC CTA TTC CGT TTT GCA AAA CCC        6613
Val Pro Ile Ile Ala Arg Ala Ala Asp Leu Phe Arg Phe Ala Lys Pro
             50                  55                  60

ATG TTA ATT CTT CCT CGG CAA CAT CGA CCG ATA GTA AGG ACA AAG CCA        6661
Met Leu Ile Leu Pro Arg Gln His Arg Pro Ile Val Arg Thr Lys Pro
 65                  70                  75

CCA GAT GGA ACT GGA GTT CGT GGT ACC GGA TTG GCC GGA ACT AGG GAT        6709
Pro Asp Gly Thr Gly Val Arg Gly Thr Gly Leu Ala Gly Thr Arg Asp
     80                  85                  90

TCG TTT ATA GTG CGG CTA TTT GAA GAT GTT GCA GGA TGT TCC ACA GAA        6757
Ser Phe Ile Val Arg Leu Phe Glu Asp Val Ala Gly Cys Ser Thr Glu
 95                 100                 105                 110

TGG CAG GAT GTT CTA TCT GGA TAT TTG ATG TTG GAA TCT GAA GTT TCT        6805
Trp Gln Asp Val Leu Ser Gly Tyr Leu Met Leu Glu Ser Glu Val Ser
                115                 120                 125

GGT AAT GCT CCA CAT AGC TTG TGG ATA GTT GGG GCG GCA GAT ATA TGT        6853
Gly Asn Ala Pro His Ser Leu Trp Ile Val Gly Ala Ala Asp Ile Cys
            130                 135                 140

GCC ATT GCG CTC GAA TGT ATT CCT TTG CCA AAA AGG TTA CTT GCA ATC        6901
Ala Ile Ala Leu Glu Cys Ile Pro Leu Pro Lys Arg Leu Leu Ala Ile
            145                 150                 155

AAA GTG TCT GGG ACC TGG TCC GGT ATG CCG TGG GCC ATT CCC GAC AAT        6949
Lys Val Ser Gly Thr Trp Ser Gly Met Pro Trp Ala Ile Pro Asp Asn
160                 165                 170

ATT CAA ACT CTC TTG ACA TCT ACA TGG GAA CCG AAG TTC GAC ACC CCA        6997
Ile Gln Thr Leu Leu Thr Ser Thr Trp Glu Pro Lys Phe Asp Thr Pro
175                 180                 185                 190

GAA GAT AGA GCG CAT TTT TGC GAC AGT GAT ATG GTA TGT GTA TAC AAA        7045
Glu Asp Arg Ala His Phe Cys Asp Ser Asp Met Val Cys Val Tyr Lys
                195                 200                 205

ATC CTC GGG TCC CCA CCC AAT CCT CTA AAA CCT CCG GAA ATC GAA CCA        7093
Ile Leu Gly Ser Pro Pro Asn Pro Leu Lys Pro Pro Glu Ile Glu Pro
            210                 215                 220

CCT CAA ATG AGT AGT ACA CCC GGC AGA TTA TTC TGT TGT GGA AAA TGT        7141
Pro Gln Met Ser Ser Thr Pro Gly Arg Leu Phe Cys Cys Gly Lys Cys
            225                 230                 235

TGC AAG AAA GAA GAT AGA GAT GCG ATT GCA ATT CCG GTT CGT TAC ACT        7189
Cys Lys Lys Glu Asp Arg Asp Ala Ile Ala Ile Pro Val Arg Tyr Thr
240                 245                 250

GCG ACA GGA AAG TCA CGA ATA CAG AAA AAA TGT AGA GCC GGT AGT CAT        7237
Ala Thr Gly Lys Ser Arg Ile Gln Lys Lys Cys Arg Ala Gly Ser His
255                 260                 265                 270

TAG   CTGTTATTCG ACAGACCTAC TTGCTACCAA TTAGATATAA TTACATGATG           7290

GGGCGTATAC ACATTACGAT TAGGTGCATC GCTACAACCG TCGCTATAGT GTCACGTATA      7350
```

-continued

```
ATTTGTATAT TAGTGCAATA ACAAACCCTT CTAGATCACT TATGTATCCA GGCTATCTTC      7410

CATATACTTC TAACATCAGG AGAGATTCAA CAATCGAGCG CATTTGAAAG ACAACG ATG      7469
                                                              Met
                                                               1

AGC AGA GTC AAT GCT ACA ATG TTC GAT GAT ATG GAT ATA CCA AGA GGA        7517
Ser Arg Val Asn Ala Thr Met Phe Asp Asp Met Asp Ile Pro Arg Gly
         5                  10                  15

CGA TTT GGT AAG CCA CCG AGA AAG ATT ACT AAT GTA AAT TTT TGG CAT        7565
Arg Phe Gly Lys Pro Pro Arg Lys Ile Thr Asn Val Asn Phe Trp His
         20                  25                  30

GTG GTT GTT GAT GAA TTC ACA GAA GGA ATC GTT CAA TGT ATG GAA GCC        7613
Val Val Val Asp Glu Phe Thr Glu Gly Ile Val Gln Cys Met Glu Ala
 35                  40                  45

CGA GAG AGA TTA GGC CTT TTA TGT ACC ATA TCT ACT AAC GAG GGA TCT        7661
Arg Glu Arg Leu Gly Leu Leu Cys Thr Ile Ser Thr Asn Glu Gly Ser
 50                  55                  60                  65

ATT ACA TCG TTT GAT ATA CAC AAG GAT ATG TGG TGT CAA ATG GTT ATC        7709
Ile Thr Ser Phe Asp Ile His Lys Asp Met Trp Cys Gln Met Val Ile
             70                  75                  80

TGG TCT GCC TAT AGA TTT TTT GCC ATG ATG GAC AAA ATG TTT TCG ATT        7757
Trp Ser Ala Tyr Arg Phe Phe Ala Met Met Asp Lys Met Phe Ser Ile
             85                  90                  95

GAA ACT ATC ACA AAT TTT ACA GAA ACT GAT CTT ACC GAA ACT GGT CAG        7805
Glu Thr Ile Thr Asn Phe Thr Glu Thr Asp Leu Thr Glu Thr Gly Gln
            100                 105                 110

TGG AGA ATA TTC TAT AGA ACT TGG GAT GTG AGA GAT GCA TTG AAG ATG        7853
Trp Arg Ile Phe Tyr Arg Thr Trp Asp Val Arg Asp Ala Leu Lys Met
            115                 120                 125

AAA CAG GTG GGA CCA TTT TTG CCC GCA TTG TTT TCA TTT CAT CTG GAA        7901
Lys Gln Val Gly Pro Phe Leu Pro Ala Leu Phe Ser Phe His Leu Glu
130                 135                 140                 145

AAC TGG ACC ACA ATG CTT TCC ATA GGA ATC AAC AAG GGT TAT GAT CGA        7949
Asn Trp Thr Thr Met Leu Ser Ile Gly Ile Asn Lys Gly Tyr Asp Arg
                150                 155                 160

CAC AAT ACA CGA AAT ATG TTC ATG ACA ATA CAG TCT GCA AGA AAT GTC        7997
His Asn Thr Arg Asn Met Phe Met Thr Ile Gln Ser Ala Arg Asn Val
                165                 170                 175

CTT AGC GGG GCA ATA GAG GTA GCT CGA TAT GCC GTG GTT CTT GCT CTA        8045
Leu Ser Gly Ala Ile Glu Val Ala Arg Tyr Ala Val Val Leu Ala Leu
            180                 185                 190

CCT GTG TGC GAG TAT AGA ACA CCC TTA GGC CTG CCG GAT GAT AGC ATA        8093
Pro Val Cys Glu Tyr Arg Thr Pro Leu Gly Leu Pro Asp Asp Ser Ile
            195                 200                 205

GGA AAT GCC ATC AAG ACA TGC TGC ACG CAA ATG CAA GCG AAT CGA TTG        8141
Gly Asn Ala Ile Lys Thr Cys Cys Thr Gln Met Gln Ala Asn Arg Leu
210                 215                 220                 225

ACA GAA ACT GGA ATA TCC AAG GAC AGT GGA CAT AAA ATA AAT GAT TCT        8189
Thr Glu Thr Gly Ile Ser Lys Asp Ser Gly His Lys Ile Asn Asp Ser
                230                 235                 240

TCT GAA GAG GAG TTG TAT TAT AGA ACC ATA CAT GAT CTT ATC AAA CCT        8237
Ser Glu Glu Glu Leu Tyr Tyr Arg Thr Ile His Asp Leu Ile Lys Pro
            245                 250                 255

AAC CGG GAA CAT TGC ATA TCA TGC AAT ATT GAG AAT AGC ATG GAT ATA        8285
Asn Arg Glu His Cys Ile Ser Cys Asn Ile Glu Asn Ser Met Asp Ile
            260                 265                 270

GAT CCC ACT ATT CAC CAT CGA TCT TCT AAT GTC ATA ACT TTA CAA GGT        8333
Asp Pro Thr Ile His His Arg Ser Ser Asn Val Ile Thr Leu Gln Gly
275                 280                 285
```

```
ACA TCA ACA TAT CCA TTT GGA CGC AGG CCG ATG AGT CGA ATG GAT GTT      8381
Thr Ser Thr Tyr Pro Phe Gly Arg Arg Pro Met Ser Arg Met Asp Val
290                 295                 300                 305

GGA GGT CTT ATG TAC CAG CAC CCC TAC ATT TGC CGC AAT CTC CAT TTA      8429
Gly Gly Leu Met Tyr Gln His Pro Tyr Ile Cys Arg Asn Leu His Leu
                310                 315                 320

CGT CCG CCT CGA TCC AGA CTA ATG AAT AGT AAA ATC CTA CAG ACA TTT      8477
Arg Pro Pro Arg Ser Arg Leu Met Asn Ser Lys Ile Leu Gln Thr Phe
            325                 330                 335

AGA CAA AGT TTC AAT CGA AGT AAT CCT CAT GCA TAC CCC ATA TAA          8522
Arg Gln Ser Phe Asn Arg Ser Asn Pro His Ala Tyr Pro Ile
        340                 345                 350
```

```
TACATACAAT CATGACAACA CTGTAATGCC TTATTGAAAA TAAAATTTTA TTATTTAAAC     8582
AACGTTAGTA GCAGTTTTTC CTAAAATCCT ATTAATAATT GTGCGATTAG TTATAAGTAG     8642
GATTCCCCGT CTCCTGTTGG CGATTCCCGA AGATTTGTCA GATAATGTGC CAATTCAGCA     8702
TCATCACCGA TTGCTGCATT CCCCTTAGTA GCGACGGCAC GACATAAAGG TTTCCAATAA     8762
GACTCTATTT CGGGGAGTGG ACTTATTCCA CAGCCCGTTG CCGAACCTAC TATGTCCATA     8822
AGACGGACAT TCTTCTCATA TAAGCGCGAA ACAGTACAGT ATCCAGCATG TCCAAGACAA     8882
CACCAATACA TCATGATAGT AAACCGAGTG TCCATTTCTT CGTGTGTAAG AGGAGCACGT     8942
TCAATACACC GTAAAGCCCG GCCTACAATT TTTCTCGTCG GGTCTGTCGG GTGGAATGGC     9002
GAAGCAGAAA TATCATATTC GTTAAGCGTG ACAGTCATTC TGTCGAATAT CTCACCCCAC     9062
AAACGAGACG ATGGTGGTTT TCCAGCTTTC ATAGCAGCCT GGGAGATCGT AGCGGCGGTT     9122
AATATGGTCC TGGCTAGACT GCGTACAGAT TTAGGCAATA GCGCAACATG TTCCCCGCCG     9182
GCAGAAAGTA TATCATAACT CTGTTCTTTT GGAGAATCTA CCCGGAGTTG CACACTCCTG     9242
CTAGATTTGC GCCGTAGAGA CCACATGGCC ATACCTCTCC AATATGTTTT AATCTTACAC     9302
GGCGCTCGTC TCCAGTATTC AAACACGTTC TCCTCTCATT AGGCTCAACG CCACATTAAA     9362
TATCTTCATA TACAACAAAA AGGCAACACG TTATTTGACA CGCCCCTTCA TGGATGGGGG     9422
GGGTCAGCGT TTGTTGCAAC AGATCATGAC AAATAAATCC AAAATCTATT ATTTTATCTC     9482
ATTAGATAGA TCAAAGAATG TCGGCTCTAT GTCTAACAAT TAAAATTATA TAATAAGAGC     9542
TTTCTCTTCA AGTCTGGATA GTTAATGCAA TTTACTGTCT ACCGACAAAT CGTTCATTCC     9602
TTTTACATCG CAGTCTGAAG AAATAGTTCC CGAGGACGCA GCGATTGGGT GAAAAATGCT     9662
ATCGGAGGCA TATATATCGG ATATAGGATG GGCGCTTCGA CTATCAGCAT CCCTCAGAGT     9722
CCTGCGCAGA TGTAGACTTT GGCGTGGGGT CAAATTCATG ATAGTTTCCC ATTCGGCTTG     9782
TTTTAGTCGA TATCCCATTC GACCAATCAT ATGAATATCG AATAGTGCTC TCCGAAGAGC     9842
ATCGTGGAAC GGACCGCTAT TTAGTCGACA TCGAATAAAA CATCGAAATA GTTTGTTTGT     9902
ATCCGCACAT AACCGAGCGA CATCGGGTTT CCATGGTAGA GGACAAAATT TGCCCACATT     9962
ATTAAGTTCA AGTCTTGAT CGGACGAGTC ACTGCCATAT TCCGGATGTG AATGTGGCAG    10022
TTGATAATCT TCGTCGTCGC TCTCATTATC TGACGATGAT AATCGTGTAT CGGGTCTGGC    10082
TCGATCTCGA TCACGACTCA TGTTGCCTCC GATGGAGCCG AAAGCAGGTT TTCTGCTCAA    10142
GTGTAATTTG GAGACTTTGG CCTGTATTAT ATAGCTACCA GCTTTTATCT TCTGCTAGGA    10202
ACAATAATTG CTAGAATTTA CATCACGTGA TATCCGGTCA AAAATTACTT GGTCTTTAAC    10262
CCAGCCCCTA ATGTACTACT TGCTCTATAT ATTCTCCACA ATGGTAAACC TCCCTCCCTA    10322
AAGATTTCAC TCCAATTTCA AGGAATTC                                       10350
```

-continued (2) INFORMATION FOR SEQ ID NO:3:

(i) SEQUENCE CHARACTERISTICS:
(A) LENGTH: 497 amino acids
(B) TYPE: amino acids
(C) STRANDEDNESS: single
(D) TOPOLOGY: linear (ii) MOLECULE TYPE:
(A) DESCRIPTION: polypeptide (vi) ORIGINAL SOURCE:
(A) ORGANISM: MDV, GA strain (vii) IMMEDIATE SOURCE:
(A) LIBRARY: genomic (xi) SEQUENCE DESCRIPTION: SEQ ID NO:3:

```
Met Cys Val Phe Gln Ile Leu Ile Ile Val Thr Thr Ile Lys Val Ala
 1               5                  10                  15

Gly Thr Ala Asn Ile Asn His Ile Asp Val Pro Ala Gly His Ser Ala
            20                  25                  30

Thr Thr Thr Ile Pro Arg Tyr Pro Pro Val Val Asp Gly Thr Leu Tyr
        35                  40                  45

Thr Glu Thr Trp Thr Trp Ile Pro Asn His Cys Asn Glu Thr Ala Thr
    50                  55                  60

Gly Tyr Val Cys Leu Glu Ser Ala His Cys Phe Thr Asp Leu Ile Leu
 65                  70                  75                  80

Gly Val Ser Cys Met Arg Tyr Ala Asp Glu Ile Val Leu Arg Thr Asp
                 85                  90                  95

Lys Phe Ile Val Asp Ala Gly Ser Ile Lys Gln Ile Glu Ser Leu Ser
            100                 105                 110

Leu Asn Gly Val Pro Asn Ile Phe Leu Ser Thr Lys Ala Ser Asn Lys
        115                 120                 125

Leu Glu Ile Leu Asn Ala Ser Leu Gln Asn Ala Gly Ile Tyr Ile Arg
    130                 135                 140

Tyr Ser Arg Asn Gly Thr Arg Thr Ala Lys Leu Asp Val Val Val Val
145                 150                 155                 160

Gly Val Leu Gly Gln Ala Arg Asp Arg Leu Pro Gln Met Ser Ser Pro
                165                 170                 175

Met Ile Ser Ser His Ala Asp Ile Lys Leu Ser Leu Lys Asn Phe Lys
            180                 185                 190

Ala Leu Val Tyr His Val Gly Asp Thr Ile Asn Val Ser Thr Ala Val
        195                 200                 205

Ile Leu Gly Pro Ser Pro Glu Ile Phe Thr Leu Glu Phe Arg Val Leu
    210                 215                 220

Phe Leu Arg Tyr Asn Pro Thr Cys Lys Phe Val Thr Ile Tyr Glu Pro
225                 230                 235                 240

Cys Ile Phe His Pro Lys Glu Pro Glu Cys Ile Thr Thr Ala Glu Gln
                245                 250                 255

Ser Val Cys His Phe Ala Ser Asn Ile Asp Ile Leu Gln Ile Ala Ala
            260                 265                 270

Ala Arg Ser Glu Asn Cys Ser Thr Gly Tyr Arg Arg Cys Ile Tyr Asp
        275                 280                 285

Thr Ala Ile Asp Glu Ser Val Gln Ala Arg Leu Thr Phe Ile Glu Pro
    290                 295                 300

Gly Ile Pro Ser Phe Lys Met Lys Asp Val Gln Val Asp Asp Ala Gly
305                 310                 315                 320

-continued

```
Leu Tyr Val Val Ala Leu Tyr Asn Gly Arg Pro Ser Ala Trp Thr
            325                 330                 335

Tyr Ile Tyr Leu Ser Thr Val Glu Thr Tyr Leu Asn Val Tyr Glu Asn
                340                 345                 350

Tyr His Lys Pro Gly Phe Gly Tyr Lys Ser Phe Leu Gln Asn Ser Ser
            355                 360                 365

Ile Val Asp Glu Asn Glu Ala Ser Asp Trp Ser Ser Ser Ile Lys
            370                 375                 380

Arg Arg Asn Asn Gly Thr Ile Ile Tyr Asp Ile Leu Thr Ser Leu
385                 390                 395                 400

Ser Ile Gly Ala Ile Ile Val Ile Val Gly Val Cys Ile Ala
            405                 410                 415

Ile Leu Ile Arg Arg Arg Arg Arg Thr Arg Gly Leu Phe Asp
            420                 425                 430

Glu Tyr Pro Lys Tyr Met Thr Leu Pro Gly Asn Asp Leu Gly Gly Met
            435                 440                 445

Asn Val Pro Tyr Asp Asn Thr Cys Ser Gly Asn Gln Val Glu Tyr Tyr
            450                 455                 460

Gln Glu Lys Ser Ala Lys Met Lys Arg Met Gly Ser Gly Tyr Thr Ala
465                 470                 475                 480

Trp Leu Lys Asn Asp Met Pro Lys Ile Arg Lys Arg Leu Asp Leu Tyr
            485                 490                 495

His
```

(2) INFORMATION FOR SEQ ID NO:4:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (iii) HYPOTHETICAL: yes (v) FRAGMENT TYPE: internal fragment (vi) ORIGINAL SOURCE:
        (A) ORGANISM: MDV
        (B) STRAIN: GA (ix) FEATURE:
        (A) NAME/KEY: peptide of MDV gene US1 polypeptide
        (B) LOCATION: 32 TO 127
        (D) OTHER INFORMATION: peptide homologous to the US1 gene
           polypeptide of herpes simplex virus type 1

(xi) SEQUENCE DESCRIPTION: SEQ ID NO: 4:

```
His Pro Glu Tyr Gly Ser Asp Ser Ser Asp Gln Asp Phe Glu Leu Asn
                5                   10                  15

Asn Val Gly Lys Phe Cys Pro Leu Pro Trp Lys Pro Asp Val Ala Arg
            20                  25                  30

Leu Cys Ala Asp Thr Asn Lys Leu Phe Arg Cys Phe Ile Arg Cys Arg
            35                  40                  45

Leu Asn Ser Gly Pro Phe His Asp Ala Leu Arg Arg Ala Leu Phe Asp
        50                  55                  60

Ile His Met Ile Gly Arg Met Gly Tyr Arg Leu Lys Gln Ala Glu Trp
65                  70                  75                  80

Glu Thr Ile Met Asn Leu Thr Pro Arg Gln Ser Leu His Leu Arg Arg
            85                  90                  95
```

(2) INFORMATION FOR SEQ ID NO:5:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: herpes simplex virus type 1 (HSV1)

(ix) FEATURE:
        (A) NAME/KEY: peptide of HSV1 gene US1 polypeptide
        (B) LOCATION: 159 TO 257
        (D) OTHER INFORMATION: peptide homologous to the US1 gene
            polypeptide of MDV (xi) SEQUENCE DESCRIPTION: SEQ ID NO: 5:

```
Arg Ala Pro Thr Pro Ser Ala Pro Ser Pro Asn Ala Met Leu Arg Arg
                 5                  10                  15

Ser Val Arg Gln Ala Gln Arg Arg Ser Ser Ala Arg Trp Thr Pro Asp
             20                  25                  30

Leu Gly Tyr Met Arg Gln Cys Ile Asn Gln Leu Phe Arg Val Leu Arg
             35                  40                  45

Val Ala Arg Asp Pro His Gly Ser Ala Asn Arg Leu Arg His Leu Ile
         50                  55                  60

Arg Asp Cys Tyr Leu Met Gly Tyr Cys Arg Ala Arg Leu Ala Pro Arg
65                  70                  75                  80

Thr Trp Cys Arg Leu Leu Gln Val Ser Gly Gly Thr Trp Gly Met His
                 85                  90                  95

Leu Arg Asn
```

(2) INFORMATION FOR SEQ ID NO:6:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: varicella-zoster virus (VZV)

(ix) FEATURE:
        (A) NAME/KEY: peptide of VZV gene 63/70 polypeptide
        (B) LOCATION: 26 TO 123
        (D) OTHER INFORMATION: peptide homologous to the US1 gene
            polypeptide of herpes simplex virus type 1 OR MDV US1
            gene polypeptide (xi) SEQUENCE DESCRIPTION: SEQ ID NO: 6:

```
Lys Met Glu Tyr Gly Ser Ala Pro Gly Pro Leu Asn Gly Arg Asp Thr
                 5                  10                  15

Ser Arg Gly Pro Gly Ala Phe Cys Thr Pro Gly Trp Glu Ile His Pro
             20                  25                  30

Ala Arg Leu Val Glu Asp Ile Asn Arg Val Phe Leu Cys Ile Ala Gln
             35                  40                  45
```

```
Ser Ser Gly Arg Val Thr Arg Asp Ser Arg Leu Arg Arg Ile Cys
    50                  55                  60

Leu Asp Phe Tyr Leu Met Gly Arg Thr Arg Gln Arg Pro Thr Leu Ala
65                  70                  75                  80

Cys Trp Glu Glu Leu Leu Gln Leu Gln Pro Thr Gln Thr Gln Cys Leu
                    85                  90                  95

Arg Ala
```

(2) INFORMATION FOR SEQ ID NO:7:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: pseudorabies virus (PRV)

(ix) FEATURE:
        (A) NAME/KEY: peptide of PRV US1 polypeptide
        (B) LOCATION: 55 TO 153
        (D) OTHER INFORMATION: peptide homologous to the US1 gene
            polypeptide of herpes simplex virus type 1 OR MDV US1
            gene polypeptide (xi) SEQUENCE DESCRIPTION: SEQ ID NO: 7:

```
His Pro Glu Tyr Gly Pro Pro Asp Pro Glu Val Arg Val His
                5                   10                  15

Gly Ala Arg Gly Pro Gly Ala Phe Cys Ala Ala Pro Trp Arg Pro Asp
                20                  25                  30

Val Met Arg Leu Ala Gly Asp Val His Arg Leu Phe Arg Gly Leu Ala
                35                  40                  45

Val Ser Ser Ala His Tyr Thr Gly Asp Ser Arg Val Leu Arg Arg Ala
    50                  55                  60

Leu Phe Asp Phe Tyr Ala His Gly Thr Thr Arg Gln Arg Pro Ser Ala
65                  70                  75                  80

Pro Cys Trp Gln Ala Leu Leu Gln Leu Ser Pro Glu Gln Ser Ala Pro
                    85                  90                  95

Leu Arg Ser
```

(2) INFORMATION FOR SEQ ID NO:8:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: equine herpesvirus type 4 (EHV4)

(ix) FEATURE:
        (A) NAME/KEY: peptide of EHV4 gene 65 polypeptide
        (B) LOCATION: 51 -149
        (D) OTHER INFORMATION: peptide homologous to the US1 gene
            polypeptide of herpes simplex virus type 1 OR MDV US1
            gene polypeptide (xi) SEQUENCE DESCRIPTION: SEQ ID NO: 8:

His Pro Glu Tyr Gly Leu Pro Leu Ser Pro Arg Ser Leu Arg Pro Tyr
                5                  10                 15

Leu Ser Arg Gly Pro Gly Ala Phe Cys Ala Pro Pro Trp Arg Pro Asp
            20                 25                 30

Val Asn Arg Leu Ala Gly Asp Val Asn Arg Leu Phe Arg Gly Ile Ser
        35                 40                 45

Thr Ser Ser Ile His Val Thr Glu Asp Ser Arg Val Leu Arg Arg Val
    50                 55                 60

Leu Leu Asp Phe Tyr Ala Met Gly Tyr Thr His Ala Arg Pro Thr Leu
65                 70                 75                 80

Glu Cys Trp Gln Ala Leu Leu Gln Leu Met Pro Glu Gln Ser Leu Pro
                85                 90                 95

Leu Arg Ala (2) INFORMATION FOR SEQ ID NO:9:

(i) SEQUENCE CHARACTERISTICS:
        (A) LENGTH:  93 amino acids
        (B) TYPE:  amino acid
        (C) STRANDEDNESS:  single
        (D) TOPOLOGY:  linear (ii) MOLECULE TYPE:  peptide (iii) HYPOTHETICAL:  yes (v) FRAGMENT TYPE:  internal fragment (vi) ORIGINAL SOURCE:
        (A) ORGANISM:  MDV
        (B) STRAIN:  GA (ix) FEATURE:
        (A) NAME/KEY:  peptide of MDV gene US10 polypeptide
        (B) LOCATION:  47 TO 139
        (D) OTHER INFORMATION:  peptide homologous to the US10 gene
            polypeptide of herpes simplex virus type 1

(xi) SEQUENCE DESCRIPTION: SEQ ID NO:  9:

Ala (vi) ORIGINAL SOURCE:
            (A) ORGANISM: herpes simplex virus type 1 (HSV1)

(ix) FEATURE:
            (A) NAME/KEY: peptide of HSV1 gene US10 polypeptide
            (B) LOCATION: 192 TO 282
            (D) OTHER INFORMATION: peptide homologous to the US10 gene
                polypeptide of MDV (xi) SEQUENCE DESCRIPTION: SEQ ID NO: 10:

Phe Arg Thr Val Val Glu Val Ser Arg Met Cys Ala Ala Asn Val Arg
                 5                  10                  15

Asp Pro Pro Pro Ala Thr Gly Ala Met Leu Gly Arg His Ala Arg
             20                  25                  30

Leu Val His Thr Gln Trp Leu Arg Ala Asn Gln Glu Thr Ser Pro Leu
             35                  40                  45

Trp Pro Trp Arg Thr Ala Ala Ile Asn Phe Ile Thr Thr Met Ala Pro
         50                  55                  60

Arg Val Gln Thr His Arg His Met His Asp Leu Leu Met Ala Cys Ala
 65                  70                  75                  80

Phe Trp Cys Cys Leu Thr His Ala Ser Thr Cys
                 85                  90

(2) INFORMATION FOR SEQ ID NO:11:

(i) SEQUENCE CHARACTERISTICS:
            (A) LENGTH: 96 amino acids
            (B) TYPE: amino acid
            (C) STRANDEDNESS: single
            (D) TOPOLOGY: linear (ii) MOLECULE TYPE: peptide (v) FRAGMENT TYPE: internal fragment (vi) ORIGINAL SOURCE:
            (A) ORGANISM: varicella-zoster virus (VZV)

(ix) FEATURE:
            (A) NAME/KEY: peptide of VZV 64 OR 69 polypeptide
            (B) LOCATION: 41 TO 135
            (D) OTHER INFORMATION: peptide homologous to the US10 gene
                polypeptide of herpes simplex virus type 1 OR MDV US10
                gene polypeptide (xi) SEQUENCE DESCRIPTION: SEQ ID NO: 11:

Ala Ala Ala Leu Cys Ala Ile Ser Thr Glu Ala Tyr Glu Ala Phe Ile
                 5                  10                  15

His Ser Pro Ser Glu Arg Pro Cys Ala Ser Leu Trp Gly Arg Ala Lys
             20                  25                  30

Asp Ala Phe Gly Arg Met Cys Gly Glu Leu Ala Ala Asp Arg Gln Arg
             35                  40                  45

Pro Pro Ser Val Pro Pro Ile Arg Arg Ala Val Leu Ser Leu Leu Arg
     50                  55                  60

Glu Gln Cys Met Pro Asp Pro Gln Ser His Leu Glu Leu Ser Glu Arg
 65                  70                  75                  80

Leu Ile Leu Met Ala Tyr Trp Cys Cys Leu Gly His Ala Gly Leu Pro
                 85                  90                  95

(2) INFORMATION FOR SEQ ID NO:12:

(i) SEQUENCE CHARACTERISTICS:
            (A) LENGTH: 95 amino acids
            (B) TYPE: amino acid

```
            (C) STRANDEDNESS:  single
            (D) TOPOLOGY:  linear (ii) MOLECULE TYPE:  peptide (v) FRAGMENT TYPE:  internal fragment (vi) ORIGINAL SOURCE:
            (A) ORGANISM:  equine herpesvirus type 4 (EHV4)

(ix) FEATURE:
            (A) NAME/KEY:  peptide of

```
Gly Thr Gly Val Arg Gly Thr Gly Leu Ala Gly Thr
                85                  90
```

(2) INFORMATION FOR SEQ ID NO:14:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (v) FRAGMENT TYPE: N-terminal fragment (vi) ORIGINAL SOURCE:
        (A) ORGANISM: herpes simplex virus type 1 (HSV1)

(ix) FEATURE:
        (A) NAME/KEY: peptide of HSV1 gene US2 polypeptide
        (B) LOCATION: 1 TO 92
        (D) OTHER INFORMATION: peptide homologous to the US2 gene
            polypeptide of MDV (xi) SEQUENCE DESCRIPTION: SEQ ID NO: 14:

```
Met Gly Val Val Val Asn Val Met Thr Leu Leu Asp Gln Asn Asn
                5                  10                  15

Ala Leu Pro Arg Thr Ser Val Asp Ala Ser Pro Ala Leu Trp Ser Phe
            20                  25                  30

Leu Leu Arg Gln Cys Arg Ile Leu Ala Ser Glu Pro Leu Gly Thr Pro
        35                  40                  45

Val Val Val Arg Pro Ala Asn Leu Arg Arg Leu Ala Glu Pro Leu Met
    50                  55                  60

Asp Leu Pro Lys Pro Thr Arg Pro Ile Val Arg Thr Arg Ser Cys Arg
65                  70                  75                  80

Cys Pro Pro Asn Thr Thr Thr Gly Leu Phe Ala Glu
                85                  90
```

(2) INFORMATION FOR SEQ ID NO:15:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (v) FRAGMENT TYPE: N-terminal fragment (vi) ORIGINAL SOURCE:
        (A) ORGANISM: pseudorabies virus (PRV)

(ix) FEATURE:
        (A) NAME/KEY: peptide of PRV US2 polypeptide
        (B) LOCATION: 1 to 98
        (D) OTHER INFORMATION: peptide homologous to the US2 gene
            polypeptide of herpes simplex virus type 1 OR MDV US 2
            gene polypeptide (xi) SEQUENCE DESCRIPTION: SEQ ID NO: 15:

```
Met Gly Val Thr Ala Ile Thr Val Val Thr Leu Met Asp Gly Ser Gly
                5                  10                  15

Arg Ile Pro Ala Phe Val Gly Glu Ala His Pro Asp Leu Trp Lys Val
            20                  25                  30

Leu Thr Glu Trp Cys Tyr Ala Ser Leu Val Gln Gln Arg Arg Ala Ala
        35                  40                  45
```

Asp Glu Asp Thr Pro Arg Gln His Val Val Leu Arg Ser Ser Glu Ile
            50                  55                  60

Ala Pro Gly Ser Leu Ala Leu Leu Pro Arg Ala Thr Arg Pro Val Val
 65                  70                  75                  80

Arg Thr Arg Ser Asp Pro Thr Ala Pro Phe Tyr Ile Thr Thr Glu Thr
                 85                  90                  95

His Glu (2) INFORMATION FOR SEQ ID NO:16:

(i) SEQUENCE CHARACTERISTICS:
        (A) LENGTH:  100 amino acids
        (B) TYPE:  amino acid
        (C) STRANDEDNESS:  single
        (D) TOPOLOGY:  linear (ii) MOLECULE TYPE:  peptide (iii) HYPOTHETICAL:  yes (v) FRAGMENT TYPE:  internal fragment (vi) ORIGINAL SOURCE:
        (A) ORGANISM:  MDV
        (B) STRAIN:  GA (ix) FEATURE:
        (A) NAME/KEY:  peptide of MDV gene US3 polypeptide
        (B) LOCATION:  179 TO 278
        (D) OTHER INFORMATION:  peptide homologous to the US3 gene
            polypeptide of herpes simplex virus type 1

(xi) SEQUENCE DESCRIPTION: SEQ ID NO:  16:

Gly Pro Leu Pro Leu Asn Gln Ile Ile Thr Ile Glu Arg Gly Leu Leu
                 5                  10                  15

Gly Ala Leu Ala Tyr Ile His Glu Lys Gly Ile Ile His Arg Asp Val
             20                  25                  30

Lys Thr Glu Asn Ile Phe Leu Asp Lys Pro Glu Asn Val Val Leu Gly
         35                  40                  45

Asp Phe Gly Ala Ala Cys Lys Leu Asp Glu His Thr Asp Lys Pro Lys
 50                  55                  60

Cys Tyr Gly Trp Ser Gly Thr Leu Glu Thr Asn Ser Pro Glu Leu Leu
 65                  70                  75                  80

Ala Leu Asp Pro Tyr Cys Thr Lys Thr Asp Ile Trp Ser Ala Gly Leu
                 85                  90                  95

Val Leu Phe Glu
            100

(2) INFORMATION FOR SEQ ID NO:17:

(i) SEQUENCE CHARACTERISTICS:
        (A) LENGTH: 100 amino acids
        (B) TYPE:  amino acid
        (C) STRANDEDNESS:  single
        (D) TOPOLOGY:  linear (ii) MOLECULE TYPE:  peptide (v) FRAGMENT TYPE:  internal fragment (vi) ORIGINAL SOURCE:
        (A) ORGANISM:  herpes simplex virus type 1 (HSV1)

(ix) FEATURE:
        (A) NAME/KEY:  peptide of HSV1 serine/threonine-
            protein kinase
        (B) LOCATION:  275 TO 374

(D) OTHER INFORMATION: peptide homologous to the US3 gene
    polypeptide of MDV (xi) SEQUENCE DESCRIPTION: SEQ ID NO: 17:

Asn Pro Leu Gly Arg Pro Gln Ile Ala Ala Val Ser Arg Gln Leu Leu
                  5                  10                  15

Ser Ala Val Asp Tyr Ile His Arg Gln Gly Ile Ile His Arg Asp Ile
             20                  25                  30

Lys Thr Glu Asn Ile Phe Ile Asn Thr Pro Glu Asp Ile Cys Leu Gly
         35                  40                  45

Asp Phe Gly Ala Ala Cys Phe Val Gln Gly Ser Arg Ser Ser Pro Phe
     50                  55                  60

Pro Tyr Gly Ile Ala Gly Thr Ile Asp Thr Asn Ala Pro Glu Val Leu
65                  70                  75                  80

Ala Gly Asp Pro Tyr Thr Thr Thr Val Asp Ile Trp Ser Ala Gly Leu
                 85                  90                  95

Val Ile Phe Glu
            100

(2) INFORMATION FOR SEQ ID NO:18:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: varicella-zoster virus (VZV)

(ix) FEATURE:
        (A) NAME/KEY: peptide of VZV serine/threonine-protein kinase
        (B) LOCATION: 177 TO 274
        (D) OTHER INFORMATION: peptide homologous to
            serine/threonine-protein kinas polypeptide of MDV (xi) SEQUENCE DESCRIPTION: SEQ ID NO: 18:

Asn Leu Pro Ile Cys Asp Ile Leu Ala Ile Gln Arg Ser Val Leu Arg
                  5                  10                  15

Ala Leu Gln Tyr Leu His Asn Asn Ser Ile Ile His Arg Asp Ile Lys
             20                  25                  30

Ser Glu Asn Ile Phe Ile Asn His Pro Gly Asp Val Cys Val Gly Asp
         35                  40                  45

Phe Gly Ala Ala Cys Phe Pro Val Asp Ile Asn Ala Asn Arg Tyr Tyr
     50                  55                  60

Gly Trp Ala Gly Thr Ile Ala Thr Asn Ser Pro Glu Leu Leu Ala Arg
65                  70                  75                  80

Asp Pro Tyr Gly Pro Ala Val Asp Ile Trp Ser Ala Gly Ile Val Leu
                 85                  90                  95

Phe Glu (2) INFORMATION FOR SEQ ID NO:19:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE:  peptide (v) FRAGMENT TYPE:  internal fragment (vi) ORIGINAL SOURCE:
              (A) ORGANISM:  pseudorabies virus (PRV)

(ix) FEATURE:
              (A) NAME/KEY:  peptide of PRV serine/threonine-protein
                  kinase
              (B) LOCATION:  193 TO 289
              (D) OTHER INFORMATION:  peptide homologous to the
                  serine/threonine protein kinase of herpes simplex virus
                  type 1 OR the US3 gene polypeptide of MDV (xi) SEQUENCE DESCRIPTION: SEQ ID NO:  19:

Gly Pro Leu Asp Met Arg Asp Ala Gly Arg Val Ile Arg Ser Val Leu
                 5                  10                  15

Arg Gly Leu Ala Tyr Leu His Gly Met Arg Ile Met His Arg Asp Val
             20                  25                  30

Lys Ala Glu Asn Ile Phe Leu Glu Asp Val Asp Thr Val Cys Leu Gly
         35                  40                  45

Asp Leu Gly Ala Ala Arg Cys Asn Val Ala Ala Pro Asn Phe Tyr Gly
     50                  55                  60

Leu Ala Gly Thr Ile Glu Thr Asn Ala Pro Glu Val Leu Ala Arg Asp
 65                  70                  75                  80

Arg Tyr Asp Thr Lys Val Asp Val Trp Gly Ala Gly Val Val Leu Phe
                 85                  90                  95

Glu (2) INFORMATION FOR SEQ ID NO:20:

(i) SEQUENCE CHARACTERISTICS:
              (A) LENGTH:  98 amino acids
              (B) TYPE:  amino acid
              (C) STRANDEDNESS:  single
              (D) TOPOLOGY:  linear (ii) MOLECULE TYPE:  peptide (iii) HYPOTHETICAL:  yes (v) FRAGMENT TYPE:  internal fragment (vi) ORIGINAL SOURCE:
              (A) ORGANISM:  MDV
              (B) STRAIN:  GA (ix) FEATURE:
              (A) NAME/KEY: peptide of MDV gene US6 polypeptide
              (B) LOCATION:  114 TO 211
              (D) OTHER INFORMATION:  peptide homologous to the gD
                  polypeptide of herpes simplex virus type 1

(xi) SEQUENCE DESCRIPTION: SEQ ID NO:  20:

Tyr Asp Ala Leu Val Ala Trp Phe Val Leu Gly Arg Ala Cys Gly Arg
                 5                  10                  15

Pro Ile Tyr Leu Arg Glu Tyr Ala Asn Cys Ser Thr Asn Glu Pro Phe
             20                  25                  30

Gly Thr Cys Lys Leu Lys Ser Leu Gly Trp Trp Asp Arg Arg Tyr Ala
         35                  40                  45

Met Thr Ser Tyr Ile Asp Arg Asp Glu Leu Lys Leu Ile Ile Ala Ala
     50                  55                  60

Pro Ser Arg Glu Leu Ser Gly Leu Tyr Thr Arg Leu Ile Ile Ile Asn
 65                  70                  75                  80

```
Gly Glu Pro Ile Ser Ser Asp Ile Leu Leu Thr Val Lys Gly Thr Cys
                85                  90                  95

Ser Phe (2) INFORMATION FOR SEQ ID NO:21:

(i) SEQUENCE CHARACTERISTICS:
        (A) LENGTH:  99 amino acids
        (B) TYPE:    amino acid
        (C) STRANDEDNESS:  single
        (D) TOPOLOGY:  linear (ii) MOLECULE TYPE:  peptide (v) FRAGMENT TYPE:  internal fragment (vi) ORIGINAL SOURCE:
        (A) ORGANISM:  herpes simplex virus type 1 (HSV1)

(ix) FEATURE:
        (A) NAME/KEY:  peptide of HSV1 gD polypeptide
        (B) LOCATION:  118 TO 216
        (D) OTHER INFORMATION:  peptide homologous to the US6 gene
            polypeptide of MDV (xi) SEQUENCE DESCRIPTION: SEQ ID NO:  21:

Tyr Asn Leu Thr Ile Ala Trp Phe Arg Met Gly Gly Asn Cys Ala Ile
                 5                  10                  15

Pro Ile Thr Val Met Glu Tyr Thr Glu Cys Ser Tyr Asn Lys Ser Leu
                20                  25                  30

Gly Ala Cys Pro Ile Arg Thr Gln Pro Arg Trp Asn Tyr Tyr Asp Ser
                35                  40                  45

Phe Ser Ala Val Ser Glu Asp Asn Leu Gly Phe Leu Met His Ala Pro
     50                  55                  60

Ala Phe Glu Thr Ala Gly Thr Tyr Leu Arg Leu Val Lys Ile Asn Asp
 65                  70                  75                  80

Trp Thr Glu Ile Thr Gln Phe Ile Leu Glu His Arg Ala Lys Gly Ser
                85                  90                  95

Cys Lys Tyr (2) INFORMATION FOR SEQ ID NO:22:

(i) SEQUENCE CHARACTERISTICS:
        (A) LENGTH: 100 amino acids
        (B) TYPE:    amino acid
        (C) STRANDEDNESS:  single
        (D) TOPOLOGY:  linear (ii) MOLECULE TYPE:  peptide (v) FRAGMENT TYPE:  internal fragment (vi) ORIGINAL SOURCE:
        (A) ORGANISM:  pseudorabies virus (PRV)

(ix) FEATURE:
        (A) NAME/KEY:  peptide of PRV gp50 polypeptide
        (B) LOCATION:  92 TO 191
        (D) OTHER INFORMATION: peptide homologous to gD of herpes
            simplex virus type 1 OR US6 gene polypeptide of MDV (xi) SEQUENCE DESCRIPTION: SEQ ID NO:  22:

Tyr Arg Ala His Val Ala Trp Tyr Arg Ile Ala Asp Gly Cys Ala His
                 5                  10                  15

Leu Leu Tyr Phe Ile Glu Tyr Ala Asp Cys Asp Pro Arg Gln Val Phe
                20                  25                  30
```

```
Gly Arg Cys Arg Arg Arg Thr Thr Pro Met Trp Trp Thr Pro Ser Ala
            35                  40                  45

Asp Tyr Met Phe Pro Thr Glu Asp Glu Leu Gly Leu Leu Met Val Ala
         50                  55                  60

Pro Gly Arg Phe Asn Glu Gly Gln Tyr Arg Arg Leu Val Ser Val Asp
 65              70                  75                      80

Gly Val Asn Ile Leu Thr Asp Phe Met Val Ala Leu Pro Glu Gly Gln
                 85                  90                  95

Glu Cys Pro Phe
            100
```

(2) INFORMATION FOR SEQ ID NO:23:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: equine herpesvirus type 1 (EHV1)

(ix) FEATURE:
        (A) NAME/KEY: peptide of EHV1 gD polypeptide
        (B) LOCATION: 113 TO 211
        (D) OTHER INFORMATION: peptide homologous to gD of herpes
            simplex virus type 1 OR US6 gene polypeptide of MDV (xi) SEQUENCE DESCRIPTION: SEQ ID NO: 23:

```
Tyr Ser Ala Arg Leu Thr Trp Phe Lys Ile Met Pro Thr Cys Ala Thr
             5                  10                  15

Pro Ile His Asp Val Ser Tyr Met Lys Cys Asn Pro Lys Leu Ser Phe
            20                  25                  30

Ala Met Cys Asp Glu Arg Ser Asp Ile Leu Trp Gln Ala Ser Leu Ile
            35                  40                  45

Thr Met Ala Ala Glu Thr Asp Asp Glu Leu Gly Leu Val Leu Ala Ala
         50                  55                  60

Pro Ala His Ser Ala Ser Gly Leu Tyr Arg Arg Val Ile Glu Ile Asp
 65              70                  75                      80

Gly Arg Arg Ile Tyr Thr Asp Phe Ser Val Thr Ile Pro Ser Glu Arg
                 85                  90                  95

Cys Pro Ile
```

(2) INFORMATION FOR SEQ ID NO:24:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: bovine herpesvirus type 1 (BHV1)

(ix) FEATURE:
        (A) NAME/KEY: peptide of BHV1 gD polypeptide
        (B) LOCATION: 101 TO 199
        (D) OTHER INFORMATION: peptide homologous to gD of herpes simplex virus type 1 OR US6 gene polypeptide of MDV (xi) SEQUENCE DESCRIPTION: SEQ ID NO: 24:

Tyr Asn Ala Thr Val Ile Trp Tyr Lys Ile Glu Ser Gly Cys Ala Arg
                 5                  10                  15

Pro Leu Tyr Tyr Met Glu Tyr Thr Glu Cys Glu Pro Arg Lys His Phe
                20                  25                  30

Gly Tyr Cys Arg Tyr Arg Thr Pro Pro Phe Trp Asp Ser Phe Leu Ala
             35                  40                  45

Gly Phe Ala Tyr Pro Thr Asp Asp Glu Leu Gly Leu Ile Met Ala Ala
         50                  55                  60

Pro Ala Arg Leu Val Glu Gly Gln Tyr Arg Arg Ala Leu Tyr Ile Asp
65                   70                  75                   80

Gly Thr Val Ala Tyr Thr Asp Phe Met Val Trp Leu Pro Ala Gly Asp
                 85                  90                  95

Cys Trp Phe (2) INFORMATION FOR SEQ ID NO:25:

(i) SEQUENCE CHARACTERISTICS:
         (A) LENGTH: 97 amino acids
         (B) TYPE: amino acid
         (C) STRANDEDNESS: single
         (D) TOPOLOGY: linear (ii) MOLECULE TYPE: peptide (iii) HYPOTHETICAL: yes (v) FRAGMENT TYPE: internal fragment (vi) ORIGINAL SOURCE:
         (A) ORGANISM: MDV
         (B) STRAIN: GA (ix) FEATURE:
         (A) NAME/KEY: peptide of MDV gene US7 polypeptide
         (B) LOCATION: 47 TO 143
         (D) OTHER INFORMATION: peptide homologous to the gI
             polypeptide of herpes simplex virus type 1

(xi) SEQUENCE DESCRIPTION: SEQ ID NO: 25:

Val Arg Gly Gln Leu Leu Phe Leu Gly Asp Gln Thr Arg Thr Ser Ser
                 5                  10                  15

Tyr Thr Gly Thr Thr Glu Ile Leu Lys Trp Asp Glu Glu Tyr Lys Cys
                20                  25                  30

Tyr Ser Val Leu His Ala Thr Ser Tyr Met Asp Cys Pro Ala Ile Asp
             35                  40                  45

Ala Thr Val Phe Arg Gly Cys Arg Asp Ala Val Val Tyr Ala Gln Pro
     50                  55                  60

His Gly Arg Val Gln Pro Phe Pro Glu Lys Gly Thr Leu Leu Arg Ile
65                   70                  75                   80

Val Glu Pro Arg Val Ser Asp Thr Gly Ser Tyr Tyr Ile Arg Val Ser
                 85                  90                  95

Leu (2) INFORMATION FOR SEQ ID NO:26:

(i) SEQUENCE CHARACTERISTICS:
         (A) LENGTH: 99 amino acids
         (B) TYPE: amino acid
         (C) STRANDEDNESS: single
         (D) TOPOLOGY: linear (ii) MOLECULE TYPE:  peptide (v) FRAGMENT TYPE:  internal fragment (vi) ORIGINAL SOURCE:
            (A) ORGANISM:  herpes simplex virus type 1 (HSV1)

(ix) FEATURE:
            (A) NAME/KEY:  peptide of HSV1 gI polypeptide
            (B) LOCATION:  53 TO 151
            (D) OTHER INFORMATION:  peptide homologous to the US7 gene
                polypeptide of MDV (xi) SEQUENCE DESCRIPTION: SEQ ID NO:  26:

Ile Leu Gly Glu Leu Arg Phe Val Gly Asp Gln Val Pro His Thr Thr
                 5                  10                  15

Tyr Tyr Asp Gly Gly Val Glu Leu Trp His Tyr Pro Met Gly His Lys
            20                  25                  30

Cys Pro Arg Val Val His Val Val Thr Val Thr Ala Cys Pro Arg Arg
        35                  40                  45

Pro Ala Val Ala Phe Ala Leu Cys Arg Ala Thr Asp Ser Thr His Ser
    50                  55                  60

Pro Ala Tyr Pro Thr Leu Glu Leu Asn Leu Ala Gln Gln Pro Leu Leu
65                  70                  75                  80

Arg Val Gln Arg Ala Thr Arg Asp Tyr Ala Gly Val Tyr Val Leu Arg
                85                  90                  95

Val Trp Val (2) INFORMATION FOR SEQ ID NO:27:

(i) SEQUENCE CHARACTERISTICS:
            (A) LENGTH:  100 amino acids
            (B) TYPE:  amino acid
            (C) STRANDEDNESS:  single
            (D) TOPOLOGY:  linear (ii) MOLECULE TYPE:  peptide (v) FRAGMENT TYPE:  internal fragment (vi) ORIGINAL SOURCE:
            (A) ORGANISM:  varicella-zoster virus (VZV)

(ix) FEATURE:
            (A) NAME/KEY:  peptide of VZV gI polypeptide
            (B) LOCATION:  51 TO 150
            (D) OTHER INFORMATION: peptide homologous to gI of herpes
                simplex virus type 1 OR US7 gene polypeptide of MDV (xi) SEQUENCE DESCRIPTION: SEQ ID NO:  27:

Ile Lys Gly Gln Leu Val Phe Ile Gly Glu Gln Leu Pro Thr Gly Thr
                 5                  10                  15

Asn Tyr Ser Gly Thr Leu Glu Leu Leu Tyr Ala Asp Thr Val Ala Phe
            20                  25                  30

Cys Phe Arg Ser Val Gln Val Ile Arg Tyr Asp Gly Cys Pro Arg Ile
        35                  40                  45

Arg Thr Ser Ala Phe Ile Ser Cys Arg Tyr Lys His Ser Trp His Tyr
    50                  55                  60

Gly Asn Ser Thr Asp Arg Ile Ser Thr Glu Pro Asp Ala Gly Val Met
65                  70                  75                  80

Leu Lys Ile Thr Lys Pro Gly Ile Asn Asp Ala Gly Val Tyr Val Leu
                85                  90                  95

Leu Val Arg Leu

100

(2) INFORMATION FOR SEQ ID NO:28:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: pseudorabies virus (PRV)

(ix) FEATURE:
        (A) NAME/KEY: peptide of PRV gp53 polypeptide
        (B) LOCATION: 59 TO 152
        (D) OTHER INFORMATION: peptide homologous to gI of herpes
            simplex virus type 1 OR US7 gene polypeptide of MDV (xi) SEQUENCE DESCRIPTION: SEQ ID NO: 28:

Ile Asp Gly Thr Leu Leu Phe Leu Glu Gly Pro Ser Pro Ser Asn Tyr
              5                    10                15

Ser Gly Arg Val Glu Leu Leu Arg Leu Asp Pro Lys Arg Ala Cys Tyr
            20                  25                30

Thr Arg Glu Tyr Ala Ala Glu Tyr Asp Leu Cys Pro Arg Val His His
            35                  40                45

Glu Ala Phe Arg Gly Cys Leu Arg Lys Arg Glu Pro Leu Ala Arg Arg
     50                  55                60

Ala Ser Ala Ala Val Glu Ala Arg Arg Leu Leu Phe Val Ser Arg Pro
65                  70                75                80

Ala Pro Pro Asp Ala Gly Ser Tyr Val Leu Arg Val Arg Val
            85                  90

(2) INFORMATION FOR SEQ ID NO:29:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: equine herpesvirus type 1 (EHV1)

(ix) FEATURE:
        (A) NAME/KEY: peptide of EHV1 gI polypeptide
        (B) LOCATION: 51 TO 149
        (D) OTHER INFORMATION: peptide homologous to gI of herpes
            simplex virus type 1 OR US7 gene polypeptide of MDV (xi) SEQUENCE DESCRIPTION: SEQ ID NO: 29:

Leu Val Gly His Leu Leu Phe Leu Asp Gly Gln Arg Leu Pro Thr Thr
              5                    10                15

Asn Tyr Ser Gly Leu Ile Glu Leu Ile His Tyr Asn Tyr Ser Ser Val
            20                  25                30

Cys Tyr Thr Val Ile Gln Thr Ile Ser Tyr Glu Ser Cys Pro Arg Val
            35                  40                45

Ala Asn Asn Ala Phe Arg Ser Cys Leu His Lys Thr Ser Lys His Tyr
     50                  55                60

```
His Asp Tyr Phe Arg Val Asn Ala Ser Val Glu Thr Asn Val Leu Leu
 65                  70                  75                  80

Asn Ile Thr Lys Pro Gln Pro Thr Asp Ser Gly Ala Tyr Ile Leu Arg
                 85                  90                  95

Val Lys Leu
```

(2) INFORMATION FOR SEQ ID NO:30:

(i) SEQUENCE CHARACTERISTICS:
        (A) LENGTH:  95 amino acids
        (B) TYPE:  amino acid
        (C) STRANDEDNESS:  single
        (D) TOPOLOGY:  linear (ii) MOLECULE TYPE:  peptide (iii) HYPOTHETICAL:  yes (v) FRAGMENT TYPE:  internal fragment (vi) ORIGINAL SOURCE:
        (A) ORGANISM:  MDV
        (B) STRAIN:  GA (ix) FEATURE:
        (A) NAME/KEY:  peptide of MDV gene US8 polypeptide
        (B) LOCATION:  232 TO 326
        (D) OTHER INFORMATION:  peptide homologous to the gE
            polypeptide of herpes simplex virus type 1

(xi) SEQUENCE DESCRIPTION: SEQ ID NO: 30:

```
Cys Lys Phe Val Thr Ile Tyr Glu Pro Cys Ile Phe His Pro Lys Glu
                 5                  10                  15

Pro Glu Cys Ile Thr Thr Ala Glu Gln Ser Val Cys His Phe Ala Ser
             20                  25                  30

Asn Ile Asp Ile Leu Gln Ile Ala Ala Ala Arg Ser Glu Asn Cys Ser
         35                  40                  45

Thr Gly Tyr Arg Arg Cys Ile Tyr Asp Thr Ala Ile Asp Glu Ser Val
     50                  55                  60

Gln Ala Arg Leu Thr Phe Ile Glu Pro Gly Ile Pro Ser Phe Lys Met
65                  70                  75                  80

Lys Asp Val Gln Val Asp Asp Ala Gly Leu Tyr Val Val Val Ala
                 85                  90                  95
```

(2) INFORMATION FOR SEQ ID NO:31:

(i) SEQUENCE CHARACTERISTICS:
(A) LENGTH: 91 amino acids
(B) TYPE: amino acid
(C) STRANDEDNESS: single
(D) TOPOLOGY: linear (ii) MOLECULE TYPE: peptide (v) FRAGMENT TYPE: internal fragment (vi) ORIGINAL SOURCE:
(A) ORGANISM: herpes simplex virus type 1 (HSV1)

(ix) FEATURE:
(A) NAME/KEY: peptide of HSV1 gE polypeptide
(B) LOCATION: 271 to 361
(D) OTHER INFORMATION: peptide homologous to the US8 gene polypeptide of MDV (xi) SEQUENCE DESCRIPTION: SEQ ID NO: 31:

```
Cys Ala Glu Met Arg Ile Tyr Glu Ser Cys Leu Tyr His Pro Gln Leu
```

```
                   5                  10                  15
Pro Glu Cys Leu Ser Pro Ala Asp Ala Pro Cys Ala Ala Ser Thr Trp
                    20                  25                  30

Thr Ser Arg Leu Ala Val Arg Ser Tyr Ala Gly Cys Ser Arg Thr Asn
            35                  40                  45

Pro Pro Pro Arg Cys Ser Ala Glu Ala His Met Glu Pro Val Pro Gly
    50                  55                  60

Leu Ala Trp Gln Ala Ala Ser Val Asn Leu Glu Phe Arg Asp Ala Ser
65                  70                  75                  80

Pro Gln His Ser Gly Leu Tyr Leu Cys Val Val
                85                  90

(2) INFORMATION FOR SEQ ID NO:32:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: varicella-zoster virus (VZV)

(ix) FEATURE:
        (A) NAME/KEY: peptide of VZV gE polypeptide
        (B) LOCATION: 387 TO 480
        (D) OTHER INFORMATION: peptide homologous to gE of herpes
            simplex virus type 1 OR US8 gene polypeptide of MDV (xi) SEQUENCE DESCRIPTION: SEQ ID NO: 32:

Cys Gln Pro Met Arg Leu Tyr Ser Thr Cys Leu Tyr His Pro Asn Ala
                5                  10                  15

Pro Gln Cys Leu Ser His Met Asn Ser Gly Cys Thr Phe Thr Ser Pro
                    20                  25                  30

His Leu Ala Gln Arg Val Ala Ser Thr Val Tyr Gln Asn Cys Glu His
            35                  40                  45

Ala Asp Asn Tyr Thr Ala Tyr Cys Leu Gly Ile Ser His Met Glu Pro
    50                  55                  60

Ser Phe Gly Leu Ile Leu His Asp Gly Gly Thr Thr Leu Lys Phe Val
65                  70                  75                  80

Asp Thr Pro Glu Ser Leu Ser Gly Leu Tyr Val Phe Val Val
                85                  90

(2) INFORMATION FOR SEQ ID NO:33:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: pseudorabies virus (PRV)

(ix) FEATURE:
        (A) NAME/KEY: peptide of PRV gI polypeptide
        (B) LOCATION: 274 TO 356
        (D) OTHER INFORMATION: peptide homologous to gE of herpes
``` simplex virus type 1 OR US8 gene polypeptide of MDV (xi) SEQUENCE DESCRIPTION: SEQ ID NO: 33:

Cys Leu Leu Tyr Tyr Val Tyr Glu Pro Cys Ile Tyr His Pro Arg Ala
                 5                  10                 15

Pro Glu Cys Leu Arg Pro Val Asp Pro Ala Cys Ser Phe Thr Ser Pro
             20                  25                  30

Ala Arg Ala Ala Leu Val Ala Arg Arg Ala Tyr Ala Ser Cys Ser Pro
             35                  40                  45

Leu Leu Gly Asp Arg Trp Leu Thr Ala Cys Pro Phe Asp Ala Phe Gly
         50                  55                  60

Glu Glu Val His Thr Asn Ala Thr Ala Asp Glu Ser Gly Leu Tyr Val
65                   70                  75                  80

Leu Val Met (2) INFORMATION FOR SEQ ID NO:34:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (vi) ORIGINAL SOURCE:
        (A) ORGANISM: equine herpesvirus type 1 (EHV1)

(ix) FEATURE:
        (A) NAME/KEY: peptide of EHV1 gE polypeptide
        (B) LOCATION: 249 TO 343
        (D) OTHER INFORMATION: peptide homologous to gE of herpes
            simplex virus type 1 OR US8 gene polypeptide of MDV (xi) SEQUENCE DESCRIPTION: SEQ ID NO: 34:

Cys Asp Leu Phe Arg Val Phe Glu Thr Cys Ile Phe His Pro Thr Ala
                 5                  10                  15

Met Ala Cys Leu His Pro Glu Gln His Thr Cys Ser Phe Thr Ser Pro
             20                  25                  30

Ile Arg Ala Thr Lys Ile Leu His Arg Val Tyr Gly Asn Cys Ser Asp
             35                  40                  45

His Gly Asn Ser Trp Pro Ser Arg Cys His Ser Thr Leu Leu Gly Asn
         50                  55                  60

Arg Leu Tyr Phe Ile Gln Pro Ala Gln Asn Arg Val Asp Leu Leu Phe
65                   70                  75                  80

Lys Asp Thr Pro Ala Ser Ala Thr Gly Leu Tyr Val Phe Val Leu
                 85                  90                  95